US011084784B2

(12) United States Patent
Sharma et al.

(10) Patent No.: US 11,084,784 B2
(45) Date of Patent: Aug. 10, 2021

(54) ROR-GAMMA MODULATORS AND USES THEREOF

(71) Applicant: PIRAMAL ENTERPRISES LIMITED, Mumbai (IN)

(72) Inventors: Rajiv Sharma, Fremont, CA (US); Bichismita Sahu, Mumbai (IN); Sunil Vasantrao Mali, Nasik (IN); Deepak Singh, Mumbai (IN); Pramod Bhaskar Kumar, Mumbai (IN); Mahesh Dawange, Mumbai (IN); Hitesh Mistry, Mumbai (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 69 days.

(21) Appl. No.: 15/128,932

(22) PCT Filed: Mar. 25, 2015

(86) PCT No.: PCT/IB2015/052198
§ 371 (c)(1),
(2) Date: Sep. 23, 2016

(87) PCT Pub. No.: WO2015/145371
PCT Pub. Date: Oct. 1, 2015

(65) Prior Publication Data
US 2018/0215707 A1   Aug. 2, 2018

Related U.S. Application Data

(60) Provisional application No. 61/970,969, filed on Mar. 27, 2014.

(51) Int. Cl.
| C07C 317/32 | (2006.01) |
| C07D 311/22 | (2006.01) |
| C07D 335/06 | (2006.01) |
| C07D 265/36 | (2006.01) |
| C07D 207/27 | (2006.01) |
| C07D 295/26 | (2006.01) |
| C07C 233/29 | (2006.01) |
| C07C 237/22 | (2006.01) |
| A61K 31/18 | (2006.01) |
| A61K 31/351 | (2006.01) |
| C07C 217/88 | (2006.01) |
| C07C 317/24 | (2006.01) |
| C07C 311/08 | (2006.01) |
| C07C 255/46 | (2006.01) |

(Continued)

(52) U.S. Cl.
CPC .......... *C07C 317/32* (2013.01); *A61K 31/165* (2013.01); *A61K 31/18* (2013.01); *A61K 31/277* (2013.01); *A61K 31/351* (2013.01); *A61K 31/382* (2013.01); *A61K 31/402* (2013.01); *A61K 31/5375* (2013.01); *C07C 205/36* (2013.01); *C07C 211/45* (2013.01); *C07C 215/70* (2013.01); *C07C 217/48* (2013.01); *C07C 217/76* (2013.01); *C07C 217/88* (2013.01); *C07C 225/22* (2013.01); *C07C 229/42* (2013.01); *C07C 233/29* (2013.01); *C07C 233/54* (2013.01); *C07C 237/22* (2013.01); *C07C 237/52* (2013.01); *C07C 255/46* (2013.01); *C07C 255/50* (2013.01); *C07C 309/89* (2013.01); *C07C 311/08* (2013.01); *C07C 311/21* (2013.01); *C07C 311/37* (2013.01); *C07C 317/24* (2013.01); *C07C 317/44* (2013.01); *C07C 323/09* (2013.01); *C07C 381/10* (2013.01); *C07D 207/27* (2013.01); *C07D 211/14* (2013.01); *C07D 213/30* (2013.01); *C07D 231/12* (2013.01); *C07D 233/58* (2013.01); *C07D 257/04* (2013.01); *C07D 265/36* (2013.01); *C07D 295/088* (2013.01); *C07D 295/135* (2013.01); *C07D 295/192* (2013.01); *C07D 295/26* (2013.01); *C07D 305/08* (2013.01); *C07D 311/22* (2013.01); *C07D 317/72* (2013.01); *C07D 335/06* (2013.01); *C07F 5/025* (2013.01); *C07F 7/1804* (2013.01); *C07C 2601/02* (2017.05); *C07C 2601/04* (2017.05); *C07C 2601/08* (2017.05); *C07C 2601/14* (2017.05); *C07C 2602/10* (2017.05)

(58) Field of Classification Search
CPC ..................................................... C07C 317/32
USPC ..................................................... 514/230.5
See application file for complete search history.

(56) References Cited

U.S. PATENT DOCUMENTS 5,968,938 A    10/1999   Williams et al.

FOREIGN PATENT DOCUMENTS

| WO | WO-00/68223 | 11/2000 |
| WO | WO-2004/063147 | 7/2004 |

(Continued)

OTHER PUBLICATIONS

International Search Report and Written Opinion for International Application No. PCT/IB2015/052198, dated Aug. 24, 2015, 22 pages.

(Continued)

*Primary Examiner* — Taofiq A Solola
(74) *Attorney, Agent, or Firm* — Foley & Lardner LLP

(57)    ABSTRACT

The present invention relates to a compound of formula I, or an isotopic form, stereoisomer, a tautomer, a pharmaceutically acceptable salt, a solvate, a polymorph, a prodrug, N-oxide or S-oxide thereof; and processes for their preparation. The invention further relates to pharmaceutical compositions containing the compounds and their use in the treatment of diseases or disorders mediated by RORγ.

18 Claims, No Drawings

(51) Int. Cl.

| | |
|---|---|
| C07C 233/54 | (2006.01) |
| C07C 217/48 | (2006.01) |
| C07C 211/45 | (2006.01) |
| C07C 215/70 | (2006.01) |
| C07C 255/50 | (2006.01) |
| A61K 31/277 | (2006.01) |
| C07C 309/89 | (2006.01) |
| C07C 225/22 | (2006.01) |
| C07C 229/42 | (2006.01) |
| C07C 317/44 | (2006.01) |
| A61K 31/165 | (2006.01) |
| C07C 323/09 | (2006.01) |
| A61K 31/5375 | (2006.01) |
| C07C 311/37 | (2006.01) |
| C07F 5/02 | (2006.01) |
| A61K 31/402 | (2006.01) |
| C07D 317/72 | (2006.01) |
| C07C 217/76 | (2006.01) |
| C07C 205/36 | (2006.01) |
| A61K 31/382 | (2006.01) |
| C07F 7/18 | (2006.01) |
| C07C 237/52 | (2006.01) |
| C07C 311/21 | (2006.01) |
| C07C 381/10 | (2006.01) |
| C07D 211/14 | (2006.01) |
| C07D 213/30 | (2006.01) |
| C07D 231/12 | (2006.01) |
| C07D 233/58 | (2006.01) |
| C07D 257/04 | (2006.01) |
| C07D 295/088 | (2006.01) |
| C07D 295/135 | (2006.01) |
| C07D 295/192 | (2006.01) |
| C07D 305/08 | (2006.01) |

(56) References Cited

FOREIGN PATENT DOCUMENTS

| | | |
|---|---|---|
| WO | WO-2005/040100 | 5/2005 |
| WO | WO-2006/003495 | 1/2006 |
| WO | WO-2008/100459 | 8/2008 |
| WO | WO-2013/019635 | 2/2013 |
| WO | WO-2013/029338 | 3/2013 |
| WO | WO-2013/171729 | 11/2013 |
| WO | WO-2015/082533 | 6/2015 |

OTHER PUBLICATIONS

Sun, W. et al., "2-(4-methylsulfonylaminophenyl) propanamide TRPV1 antagonists: Structure-activity relationships in the B and C-regions", Bioorganic and Medicinal Chemistry, 2012, vol. 20, pp. 1310-1318.

CAS Registry No. 1316362-97-6, STN Entry Date Aug. 12, 2011, "Compound 4-(aminosulfonyl)-N-[1-[4-(1,1-dimethylethyl)phenyl]-2-methylpropyl]-benzeneacetamide".

CAS Registry No. 1288897-74-4, STN Entry Date May 2, 2011, "Compound N-(1-(4-(cyclopentyloxy)-3-methoxyphenyl)ethyl)-3-(3-methoxy-4-(2,2,2-trifluoroethoxy)phenyl)propanamide".

CAS Registry No. 1223732-85-1, STN Entry Date May 14, 2011, "Compound N-(3,4-dihydro-3-exo-2H-1,4-benzoxazin-6-yl)-4-(trifluoromethoxy)-benzeneacetamide".

CAS Registry No. 1325371-39-8, STN Entry Date Aug. 30, 2011, "Compound N-(4-ethylphenyl)-4-[(methylamino)sulfonyl]-benzenepropanamide".

CAS Registry No. 1396856-61-3, STN Entry Date Sep. 27, 2012, "Compound 4-[(1-methylethyl)thio]-N-(tetrahydro-2H-pyran-4-yl)-N-(2,2,2-trifluoroethyl)-benzeneacetamide".

CAS Registry No. 949740-07-2, STN Entry Date Oct. 9, 2007, "Compound N-[1-[4-(2-methylpropyl)phenyl]ethyl]-4-(2-oxo-1-pyrrolidinyl)-benzeneacetamide".

CAS Registry No. 1316084-62-4, STN Entry Date Aug. 11, 2011, "Compound N-[4-(cyclohexylamino)phenyl]-4-(1-piperidinylsulfonyl)-benzeneacetamide".

CAS Registry No. 1216638-52-6, STN Entry Date Apr. 4, 2010, "Compound 4-[(dimethylamino)sulfonyl]-N-(4-ethylphenyl)-benzeneethanesulfonamide".

CAS Registry No. 1240851-51-7, STN Entry Date Sep. 14, 2010, "Compound N-(2,3-dihydro-H-inden-5-yl)-4-(2-oxo-1-pyrrolidinyl)-benzeneacetamide".

CAS Registry No. 955536-99-9, STN Entry Date Nov. 22, 2007, "Compound N-(2-methyl-5-benzothiazolyl)-4-[(1-methyethyl)sulfonyl]-benzeneacetamide".

CAS Registry No. 1278169-63-3, STN Entry Date Apr. 10, 2011, "Compound 4-[(methylamino)sulfonyl]-N-(4-phenylcyclohexyl)-benzenepropanamide".

CAS Registry No. 1318973-84-0, STN Entry Date Aug. 17, 2011, "Compound 4-(aminosulfonyl)-N-[1-(4-cyclohexylphenyl)-2-methylpropyl]-benzeneacetamide".

CAS Registry No. 1286176-67-7, STN Entry Date Apr. 26, 2011, "Compound 4-(difluoromethoxy)-N-[2-[(2-ethylphenyl)amino]-2-oxoethyl]-N-methyl-benzeneacetamide".

CAS Registry No. 1240641-80-8, STN Entry Date Sep. 13, 2010, "Compound N-methyl-4-[3-(octahydro-2(H)-isoquinolinyl)-3-oxopropyl]-benzenesulfonamide".

ROR-GAMMA MODULATORS AND USES THEREOF

CROSS-REFERENCE TO RELATED APPLICATIONS

This application is a U.S. national stage application of International Patent Application No. PCT/IB2015/052198, filed on Mar. 25, 2015, which claims priority to U.S. Provisional Application No. 61/970,969, filed on Mar. 27, 2014, the contents of each of these applications is incorporated herein by reference in their entirety.

FIELD OF THE INVENTION

The present invention relates to the compounds of formula I (as described herein), processes for their preparation, pharmaceutical compositions containing them and their use as retinoid related orphan receptor gamma (RORγ) modulators, and methods of using said compounds in the treatment of diseases mediated by RORγ.

BACKGROUND OF THE INVENTION

Nuclear receptors (NRs) are ligand-regulated transcription factors that play diverse role in the expression of target genes associated with physiological processes such as cell differentiation, development, metabolism and immunity. All members of the nuclear receptors super family are multi domain proteins. Majority of the nuclear receptors contain the four functional domains, namely N-terminal "A/B domain", DNA-binding domain or "C domain", highly variable hinge or "D domain", and C-terminal ligand-binding domain (LBD) or "E domain". Several NRs contain a highly variable C-terminal F domain.

Retinoid-related orphan receptors (RORs) are the subfamily of nuclear receptors (NRs). The ROR subfamily consists of three isoforms, namely RORalpha (RORα), RORbeta (RORβ) and RORgamma (RORγ), which are also referred to as NR1F1, NR1F2 and NR1F3 respectively. The RORα, RORβ and RORγ function as ligand dependent transcription factors and recent research studies suggest that RORs may be potential therapeutic targets for treatment of various diseases. Each of the RORs is encoded by a distinct gene RORA, RORB and RORC and each ROR gene generates several isoforms, differing only in their N-terminal "A/B domain". For RORα (α1-4), four isoforms have been identified, and RORβ gene is expressed in only one isoform in humans, whereas for RORγ, two isoforms have been identified namely RORγ1 and RORγ2. The isoform "RORγ2" is commonly known as RORγt.

RORγ2 (RORγt) is exclusively detected in a few distinct cell types of the immune system, for instance, in thymus (*Journal of Experimental Pharmacology*, 2012, 4, 141-148; *Nuclear Receptor Signaling*, 2009, 7, 1-32) while RORγ1 is expressed in many tissues, including thymus, lung, liver, kidney, skeletal muscle, adipose tissue and skin. RORγt has been identified as a key regulator of Th17 cell differentiation (Nuclear Receptor Signalling, 2009, 7, 1-32; *International Immunopharmacology*, 2011, 11, 536-542). The Th17 (T helper 17) cells constitute a distinct subset of CD4+ helper T cells that are mainly characterized by abundant interleukin (IL)-17 production. They are developmentally distinct from Th1 and Th2 cells, which are the other two subsets of T helper cells. The Th17 cells are known to be involved in the host defence against bacteria and fungi and also in the pathogenesis of autoimmune diseases. Thus, it is reported that Th17 cells play a critical role in many inflammatory and autoimmune diseases (*Immunological Reviews*, 2008, 223, 87-113). In addition, studies have shown that Th17 cells have a key role in cancer and a variety of autoimmune diseases such as collagen-induced arthritis (CIA), inflammatory bowel disease (IBD) and graft versus host disease (GVHD) (*Blood and Marrow Transplantation*, 2012, 18, S56-61).

Asthma is a chronic inflammatory disorder of airways, in the pathogenesis of which Th17 cells/IL-17 play a key role. In asthmatic patients, both RORγt and IL-17A expression levels have been shown to be increased in sputum, lung, bronchioalveolar lavage (BAL) fluids and peripheral blood and these levels directly correlate with disease severity. In addition to IL-17A, a recent study have shown that another cytokine of the IL-17 family, IL-17F, may have a crucial role in allergic airway inflammation and hence, have key implications in airway diseases, such as asthma (*Respiratory Research*, 2010, 11:78, 1-11).

The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (*Journal of Experimental Medicine*, 2008, 205, 1517-1522; *Cellular and Molecular Immunology*, 2010, 7, 182-189). Also, during the disease process Th17 cells are activated and are responsible for recruiting other inflammatory cells types, particularly neutrophils, to mediate pathology in the target tissues.

It is reiterated here that RORγt has been shown to play a critical role in the differentiation of Th17 cells and IL-17 expression. RORγt deficiency results in diminished Th17 activity and severely reduced expression of IL-17. Several studies suggest that RORγt plays a vital role in various diseases or disorders (*Journal of Experimental Pharmacology*, 2012, 4, 141-148).

PCT Application Publications WO2012100732A1, WO2013029338A1, WO2013169588A1 and WO2013171729A2 disclose compounds as modulators of RORγ and use of the compounds for the treatment of diseases mediated by RORγ.

Considering that RORγ plays an important role in the pathogenesis of numerous diseases, compounds that modulate the activity of RORγ will have therapeutic potential in treating diseases mediated/implicated by RORγ. The inventors of the present invention have developed compounds that function as modulators of RORγ. Accordingly, the compounds of the present invention find use in the treatment of diseases mediated by RORγ.

SUMMARY OF THE INVENTION

In one aspect, the present invention relates to a compound of formula I (as described herein), or an isotopic form, a stereoisomer, a tautomer, a pharmaceutically acceptable salt, a solvate, a polymorph, a prodrug, S-oxide or an N-oxide thereof.

According to another aspect of the present invention, there are provided processes for the preparation of the compounds of formula I or pharmaceutically acceptable salts thereof.

According to a further aspect of the present invention, there are provided pharmaceutical compositions comprising a compound of formula I or a stereoisomer, a tautomer, a pharmaceutically acceptable salt or a pharmaceutically acceptable solvate thereof; and at least one pharmaceutically acceptable carrier or excipient.

According to a further aspect of the present invention, there is provided a compound of formula I or a stereoisomer, a tautomer, a pharmaceutically acceptable salt or a solvate thereof; for use as a retinoid related orphan receptor gamma (RORγ) modulator.

According to yet another aspect of the present invention, there is provided a compound of formula I or a stereoisomer, a tautomer, a pharmaceutically acceptable salt or a solvate thereof; for use in the treatment of a disease or a disorder mediated by RORγ.

According to a further aspect of the present invention, there is provided a method for the treatment of a disease or disorder mediated by RORγ; comprising administering to a subject in need thereof, a therapeutically effective amount of the compound of formula I or a stereoisomer, a tautomer, a pharmaceutically acceptable salt or a solvate thereof.

In a further aspect, the present invention relates to use of a compound of formula I or a stereoisomer, a tautomer, a pharmaceutically acceptable salt or a solvate thereof; in combination with at least one further therapeutically active agent; for the treatment of a disease or disorder mediated by RORγ.

According to yet another aspect of the present invention, there is provided use of a compound of formula I or a stereoisomer, a tautomer, a pharmaceutically acceptable salt or a solvate thereof; for the manufacture of a medicament for the treatment of a disease or a disorder mediated by RORγ.

One or more further aspects of the present inventions are discussed in detail herein below. These and other objectives and aspects of the present invention will be apparent to those skilled in the art from the following description.

DETAILED DESCRIPTION OF THE INVENTION

According to the first aspect, the present invention relates to a compound of formula I,

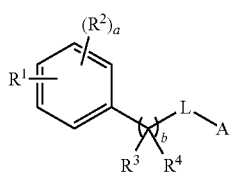

Formula I or an isotopic form, a stereoisomer, a tautomer, a pharmaceutically acceptable salt, a pharmaceutically acceptable solvate, a polymorph, a prodrug, S-oxide or N-oxide thereof; wherein:
$R^1$ is —$S(O)_mR^a$, —$S(O)_rNR^bR^c$, —$S(O)_r(NR^b)R^a$, —$NR^aR^b$, —$NR^bCOR^c$, —$NR^bS(O)_mR^a$, —O—$R^d$ or

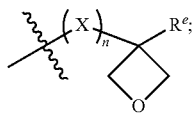

$R^a$ is $(C_1-C_8)$-alkyl, $(C_3-C_{12})$-cycloalkyl, $(C_6-C_{10})$-aryl or heterocyclyl;

$R^b$ and $R^c$ at each occurrence are independently selected from the group consisting of hydrogen, $(C_1-C_8)$-alkyl, $(C_3-C_{12})$-cycloalkyl, $(C_6-C_{10})$-aryl and heterocyclyl; or $R^b$ and $R^c$ can combine to form a saturated or unsaturated 5- or 6-membered ring, optionally containing 1 or 2 additional heteroatoms selected from the group consisting of N, S and O; wherein the ring can be unsubstituted or substituted with one or more groups independently selected from the group consisting of halogen, hydroxy, cyano, oxo, $(C_1-C_8)$-alkyl, $(C_1-C_8)$-alkoxy and halo$(C_1-C_8)$-alkyl;

$R^d$ is $(C_1-C_8)$-alkyl-O—$(C_1-C_8)$-alkyl or halo$(C_1-C_8)$-alkyl;

$R^e$ is hydrogen, $(C_1-C_8)$-alkyl, $(C_1-C_8)$-alkoxy, halo$(C_1-C_8)$-alkyl, $(C_2-C_8)$-alkenyl or $NR^{a1}R^{a2}$;

X is O, NH, $S(O)_2$ or S;

m is 0, 1 or 2;

n is 0 or 1;

r is 1 or 2;

$R^2$ at each occurrence is independently selected from the group consisting of hydrogen, halogen, hydroxy, cyano, $(C_1-C_8)$-alkyl, $(C_1-C_8)$-alkoxy, $(C_3-C_{12})$-cycloalkyl, halo$(C_1-C_8)$-alkyl, halo$(C_1-C_8)$-alkoxy, $NR^{a1}R^{a2}$, $COR^{a3}$, $COOR^{a3}$ and $CONR^{a1}R^{a2}$; or $R^1$ and $R^2$ when present on adjacent carbon atoms of the phenyl can combine to form a saturated 5- or 6-membered ring containing S or $SO_2$; which ring can be unsubstituted or substituted with one or more groups independently selected from the group consisting of halogen, cyano, oxo, $(C_1-C_8)$-alkyl, $(C_2-C_8)$-alkenyl, $(C_2-C_8)$-alkynyl, $(C_1-C_8)$-alkoxy and halo$(C_1-C_8)$-alkyl;

$R^3$ and $R^4$ are independently selected from the group consisting of hydrogen, halogen, hydroxy, cyano, $(C_1-C_8)$-alkyl, $(C_2-C_8)$-alkenyl, $(C_1-C_8)$-alkoxy and halo$(C_1-C_8)$alkyl;

a is 1 or 2;

b is 1 or 2;

L is —CO— or —$SO_2$—;

A is

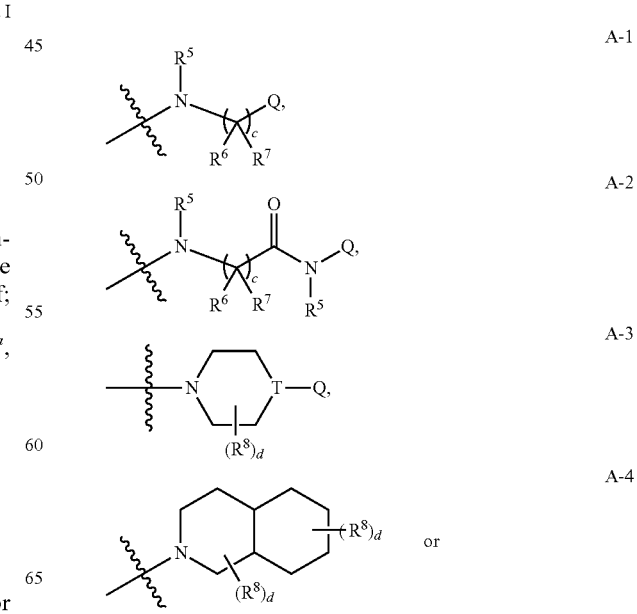

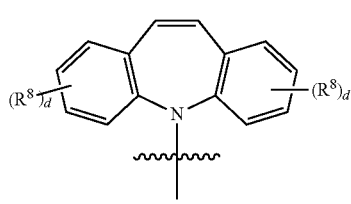
A-5

R⁵ is hydrogen, (C₁-C₈)-alkyl, halo(C₁-C₈)alkyl or (C₃-C₁₂)-cycloalkyl;

R⁶ and R⁷ are independently selected from the group consisting of hydrogen, halogen, hydroxy, cyano, (C₁-C₈)-alkyl, (C₂-C₈)-alkenyl, (C₁-C₈)-alkoxy, halo(C₁-C₈)alkyl, (C₃-C₁₂)-cycloalkyl, (C₆-C₁₀)-aryl, CONR$^{a1}$R$^{a2}$, COR$^{a3}$ and COOR$^{a3}$; or R⁶ and R⁷ can combine to form saturated or unsaturated 3-6 membered cyclic ring optionally containing 1 or 2 heteroatoms selected from the group consisting of O, N and S; wherein the ring can be unsubstituted or substituted with one or more groups independently selected from the group consisting of oxo, hydroxy, cyano, halogen, (C₁-C₈)-alkyl, halo(C₁-C₈)-alkyl, COR$^{a3}$, COOR$^{a3}$, CONR$^{a2}$R$^{a3}$, (C₁-C₈)-alkoxy and halo(C₁-C₈)-alkoxy;

R⁸ is hydrogen, halogen, hydroxy, cyano, (C₁-C₈)-alkyl, (C₂-C₈)-alkenyl, (C₁-C₈)-alkoxy, halo(C₁-C₈)alkyl, CONR$^{a1}$R$^{a2}$, COR$^{a3}$ or COOR$^{a3}$;

T is CR$^t$ or N;

R$^t$ is hydrogen, cyano, halogen, (C₁-C₈)-alkyl, (C₁-C₈)-alkoxy, (C₃-C₁₂)-cycloalkyl, halo(C₁-C₈)-alkyl or halo(C₁-C₈)-alkoxy;

c is 0, 1, 2 or 3;

d is 1 or 2;

Q is selected from the group consisting of,

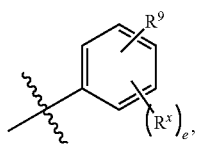
Q-1

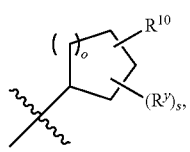
Q-2

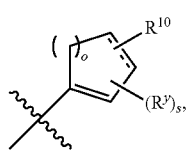
Q-3

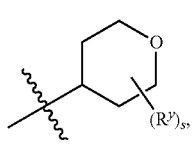
Q-4

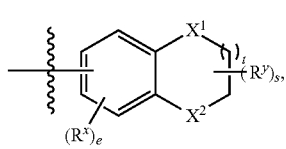
Q-5

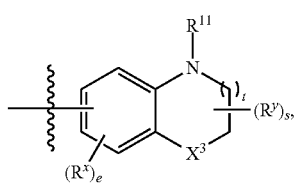
Q-6

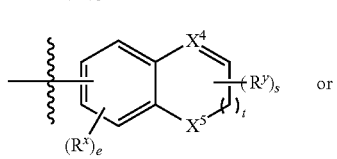
Q-7

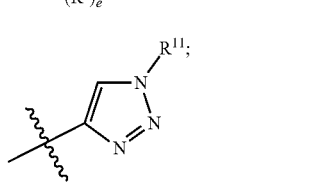
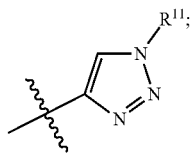
or

Q-8

R⁹ is (CR$^j$R$^j$)$_f$R$^b$, (CR$^j$R$^j$)$_f$OR$^k$, (CR$^j$R$^j$)$_f$N(R$^k$)₂, (CR$^j$R$^j$)$_f$CN, (CR$^j$R$^j$)$_f$-halogen, W—(C₃-C₁₂)-cycloalkyl, W—(C₅-C₁₀)-cycloalkenyl, W¹—(C₆-C₁₀)-aryl, W¹-heterocyclyl or W¹-heteroaryl;

R¹⁰ at each occurrence is independently selected from the group consisting of (CR$^j$R$^j$)$_f$OR$^k$, oxo, W—(C₃-C₁₂)-cycloalkyl, (C₆-C₁₀)-aryl, W¹—(C₆-C₁₀)-aryl and W¹-heteroaryl;

R$^k$ is hydrogen, (C₁-C₈)-alkyl, (C₃-C₁₂)-cycloalkyl, (C₅-C₁₀)-cycloalkenyl, —(C₁-C₈)-alkylene-(C₃-C₁₂)-cycloalkyl, —(C₁-C₈)-alkylene-(C₅-C₁₀)-cycloalkenyl, (C₆-C₁₀)-aryl, —(C₁-C₈)-alkylene-(C₆-C₁₀)-aryl, heteroaryl, heterocyclyl, —(C₁-C₈)-alkylene-heteroaryl or —(C₁-C₈)-alkylene-heterocyclyl;

R$^x$ and R$^y$ at each occurrence are independently selected from the group consisting of hydrogen, halogen, hydroxy, cyano, oxo, (C₁-C₈)-alkyl, (C₁-C₈)-alkoxy, (C₃-C₁₂)-cycloalkyl, halo(C₁-C₈)-alkyl, halo(C₁-C₈)-alkoxy, NR$^{a1}$R$^{a2}$, COR$^{a3}$, COOR$^{a3}$ and CONR$^{a1}$R$^{a2}$;

W is a bond, —O—, CO, NH, (CR$^j$R$^g$)$_f$, (CR$^j$R$^g$)$_f$—C≡C— or (C₅-C₁₀)-cycloalkenyl;

W¹ is (CR$^j$R$^j$)$_f$, (CR$^j$R$^g$)$_f$—C≡C— or (C₅-C₁₀)-cycloalkenyl;

R$^j$ is (C₁-C₈)alkyl, (C₁-C₈)alkoxy, halo(C₁-C₈)alkyl, COOR$^{a3}$ or heterocyclyl;

R$^f$ and R$^g$ are independently selected from the group consisting of hydrogen, halogen, cyano, hydroxy, (C₁-C₈)alkyl and halo(C₁-C₈)alkyl;

e is 1 or 2;

f is 1, 2, 3 or 4;

o is 0, 1, 2 or 3;

R¹¹ is hydrogen, (C₁-C₈)-alkyl, (C₃-C₁₂)-cycloalkyl, (C₅-C₁₀)-cycloalkenyl, (C₆-C₁₀)-aryl, (CR$^j$R$^g$)$_f$—(C₆-C₁₀)-aryl, (CR$^j$R$^g$)$_f$-heterocyclyl, COOR$^{a3}$ or COR$^{a3}$;

X¹ is CR¹²R¹³, O, S or S(O)₂;

X² is CR¹⁴R¹⁵ or C=R¹⁶;

X³ is O or S;

X⁴ is CR¹⁷ or N;

X⁵ is CR¹⁸R¹⁹ or S;

t is 0, 1 or 2;
s is 1 or 2;
$R^{12}$, $R^{13}$, $R^{14}$, $R^{15}$, $R^{17}$, $R^{18}$ and $R^{19}$ are independently selected from the group consisting of hydrogen, halogen, hydroxy, cyano, $(C_1-C_8)$-alkyl, $(C_2-C_8)$-alkenyl, $(C_2-C_8)$-alkynyl, $(C_1-C_8)$-alkoxy, $(C_3-C_{12})$-cycloalkyl, $(C_5-C_{10})$-cycloalkenyl, halo$(C_1-C_8)$-alkyl, $(C_6-C_{10})$-aryl, heteroaryl, heterocyclyl, $NR^{a1}R^{a2}$, $COR^{a3}$, $COOR^{a3}$, $CONR^{a1}R^{a2}$, $S(O)_q(C_1-C_8)$-alkyl and $S(O)_rNR^{a1}R^{a2}$;
$R^{16}$ is O, $(C_3-C_{12})$-cycloalkyl, $(C_5-C_{10})$-cycloalkenyl or heterocyclyl;
$R^{a1}$, $R^{a2}$ and $R^{a3}$ at each occurrence are independently selected from the group consisting of hydrogen, $(C_1-C_8)$-alkyl and $(C_3-C_{12})$-cycloalkyl;
q is 0, 1 or 2;
wherein:
each of the $(C_1-C_8)$-alkyl, $(C_1-C_8)$-alkylene, $(C_2-C_8)$-alkenyl and $(C_1-C_8)$-alkoxy can be unsubstituted or substituted with one or more groups independently selected from the group consisting of halogen, hydroxy, oxo, cyano, $(C_1-C_8)$-alkynyl, $(C_1-C_8)$-alkoxy, $(C_3-C_{12})$-cycloalkyl, $(C_6-C_{10})$-aryl, heterocyclyl, heteroaryl, halo$(C_1-C_8)$alkoxy, $C(O)R^h$, $OC(O)R^h$, $COOR^h$, $C(O)NR^hR^i$, O—$R^i$, $OC(O)NR^hR^i$, $NR^hR^i$, $NR^hC(O)R^i$, $NR^hC(O)NR^hR^i$, $S(O)_q(C_1-C_8)$-alkyl, $S(O)_rNR^hR^i$ and $NR^hS(O)_qR^i$;
each of the $(C_3-C_{12})$-cycloalkyl, $(C_5-C_{10})$-cycloalkenyl and $(C_6-C_{10})$-aryl can be unsubstituted or substituted with one or more groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, $C(O)R^h$, $COOR^h$, $C(O)NR^hR^i$, O—$R^i$, $OC(O)R^h$, $OC(O)NR^hR^i$, $NR^hR^i$, $NR^hC(O)R^i$, $NR^hC(O)NR^hR^i$, $S(O)_q(C_1-C_8)$-alkyl, $S(O)_rNR^hR^i$ and $NR^hS(O)_qR^i$;
heterocyclyl is a 3- to 10-membered ring containing 1, 2, 3 or 4 heteroatoms independently selected from the group consisting of N, S and O, wherein said heterocyclyl is unsubstituted or substituted with one or more groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, $C(O)R^h$, $COOR^h$, $C(O)NR^hR^i$, O—$R^i$, $OC(O)R^h$, $OC(O)NR^hR^i$, $NR^hR^i$, $NR^hC(O)R^i$, $NR^hC(O)NR^hR^i$, $S(O)_q(C_1-C_8)$-alkyl, $S(O)_rNR^hR^i$ and $NR^hS(O)_qR^i$;
heteroaryl is a 5- to 10-membered ring containing 1, 2, 3 or 4 heteroatoms independently selected from the group consisting of N, S and O, wherein said heteroaryl is unsubstituted or substituted with one or more groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, $C(O)R^h$, $COOR^h$, $C(O)NR^hR^i$, O—$R^i$, $OC(O)R^h$, $OC(O)NR^hR^i$, $NR^hR^i$, $NR^hC(O)R^i$, $NR^hC(O)NR^hR^i$, $S(O)_q(C_1-C_8)$-alkyl, $S(O)_rNR^hR^i$ and $NR^hS(O)_qR^i$; and
$R^h$ and $R^i$ are independently selected from the group consisting of hydrogen, $(C_1-C_8)$-alkyl, $(C_2-C_8)$-alkenyl, halo$(C_1-C_8)$alkyl, $(C_3-C_{12})$-cycloalkyl, $(C_6-C_{10})$-aryl, $(C_6-C_{10})$-aryl-$(C_1-C_8)$-alkyl, heteroaryl and heterocyclyl;
provided that,
(i) when $R^1$ is —$S(O)_rNR^bR^c$, wherein $R^b$ and $R^c$ can combine to form a saturated or unsaturated 5- or 6-membered ring, then Q is

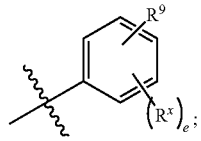

or (ii) when $R^1$ is $NR^bCOR^c$, wherein $R^b$ is hydrogen and $R^c$ is $(C_1-C_8)$-alkyl, then Q is

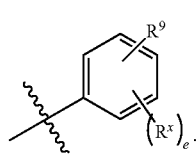

Definitions

Unless otherwise indicated, the following definitions are set forth to illustrate and define the meaning and scope of the various terms used to describe the invention herein and the appended claims. These definitions should not be interpreted in the literal sense as they are not general definitions and are relevant only for this application.

It will be understood that "substitution," "substituted" or "substituted with" means that one or more hydrogen(s) of the specified moiety are replaced with a suitable substituent and includes the implicit proviso that such substitution is in accordance with permitted valence of the substituted atom and the substituent, and results in a stable compound.

The terms "a", "an" and "the" refers to "one or more" when used in the subject specification, including the claims. Thus, for example, reference to "a compound" may include a plurality of such compounds, or reference to "a disease" or "a disorder" includes a plurality of diseases or disorders.

Also, use of "(s)" as part of a term, includes reference to the term singly or in plurality, e.g. the term compound(s) may indicate a single compound or more compounds.

It should also be noted that the term "or" is generally employed in its sense including "and/or" unless the content clearly dictates otherwise.

The term "independently" when used in the context of selection of substituents for a variable, it means that where more than one substituent is selected from a number of possible substituents, those substituents may be the same or different.

As used herein, the term "$(C_1-C_8)$-alkyl" or "alkyl", whether used alone or as part of a substituent group, refers to the radical of saturated aliphatic groups, including straight or branched-chain alkyl groups. A straight-chain or branched chain alkyl has eight or fewer carbon atoms in its backbone, for instance, $C_1-C_8$ for straight chain and $C_3-C_8$ for branched chain. As used herein, $(C_1-C_8)$-alkyl refers to an alkyl group having 1 to 8 (both inclusive) carbon atoms; can preferably refer to an alkyl group having 1 to 6 (both inclusive) carbon atoms i.e. $(C_1-C_6)$-alkyl; and more preferably, refers to an alkyl group having 1 to 4 (both inclusive) carbon atoms i.e. $(C_1-C_4)$-alkyl. Representative examples of alkyl include, but are not limited to, methyl, ethyl, n-propyl, n-butyl, n-pentyl, n-hexyl, n-heptyl, n-octyl, isopropyl, sec-butyl, isobutyl, tert-butyl, isopentyl, 2-methylbutyl and 3-methylbutyl.

Furthermore, unless stated otherwise, the alkyl group can be unsubstituted or substituted with one or more groups; preferably with 1-7 groups, more preferably with 1-3 groups independently selected from the group consisting of halogen, hydroxy, oxo, cyano, $(C_1-C_8)$-alkoxy, $(C_3-C_{12})$-cycloalkyl, $(C_6-C_{10})$-aryl, heterocyclyl, heteroaryl, halo$(C_1-C_8)$ alkoxy, $C(O)R^h$, $OC(O)R^h$, $COOR^h$, $C(O)NR^hR^i$, $O\!\!-\!\!R^i$, $OC(O)NR^hR^i$, $NR^hR^i$, $NR^hC(O)R^i$, $NR^hC(O)NR^hR^i$, $S(O)_q$ $(C_1-C_8)$-alkyl, $S(O)_rNR^hR^i$ and $NR^hS(O)_qR^i$; wherein $R^h$ and $R^i$ are independently selected from the group consisting of hydrogen, $(C_1-C_8)$-alkyl, $(C_2-C_8)$-alkenyl, halo$(C_1-C_8)$ alkyl, $(C_3-C_{12})$-cycloalkyl, $(C_6-C_{10})$-aryl, $(C_6-C_{10})$-aryl-$(C_1-C_8)$-alkyl, heteroaryl and heterocyclyl. Representative examples of substituted alkyls include, but are not limited to, benzyl, hydroxymethyl, hydroxyethyl, N-morpholinomethyl, N-indolomethyl, piperidinylmethyl and aminoethyl.

As used herein, the term "$(C_1-C_8)$-alkylene" or "alkylene", refers to the corresponding bivalent radical of $(C_1-C_8)$-alkyl group, including straight or branched-chain alkylene groups, and hence, the definition of (C1-C8)alkyl group apply. Representative examples of alkylene include, but are not limited to, methylene, ethylene, n-propylene, n-butylene, n-pentylene, n-hexylene, n-heptylene, n-octylene, and isopropylene. Furthermore, unless stated otherwise, the alkylene groups can be unsubstituted or substituted with one or more groups selected from the groups indicated above as the substituents for the corresponding alkyl group.

As used herein, the term "halogen" or "halo" refers to a fluorine, chlorine, bromine, or iodine atom.

As used herein, the term "halo$(C_1-C_8)$alkyl" or "haloalkyl", whether used alone or as part of a substituent group, refers to the alkyl group which is substituted with one or more halogens. A monohalo$(C_1-C_8)$alkyl radical, for example, can have a chlorine, bromine, iodine or fluorine atom. Dihalo- or polyhalo$(C_1-C_8)$alkyl radicals can have two or more of the same or different halogen atoms. Representative examples of halo$(C_1-C_8)$alkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl or the like groups.

As used herein, the term "$(C_2-C_8)$-alkenyl" or "alkenyl", whether used alone or as part of a substituent group, refers to a straight or branched chain hydrocarbon radical containing the indicated number of carbon atoms and at least one carbon-carbon double bond (two adjacent $sp^2$ carbon atoms). As used herein, $(C_2-C_8)$-alkenyl refers to an alkenyl group having 2 to 8 (both inclusive) carbon atoms; preferably, can refer to alkenyl group having 2 to 6 (both inclusive) carbon atoms i.e. $(C_2-C_6)$-alkenyl; and more preferably, alkenyl can refer to alkenyl group having 2 to 4 (both inclusive) carbon atoms i.e. $(C_2-C_4)$-alkenyl. Depending on the placement of double bond and substituents; if any, the geometry of the double bond may be entgegen (E), or zusammen (Z), cis or trans. Representative examples of alkenyl include, but are not limited to, vinyl, allyl and 2-propenyl. Furthermore, unless stated otherwise, the alkenyl groups can be unsubstituted or substituted with one or more groups. A substituted alkenyl refers to a $(C_1-C_8)$-alkenyl substituted with 1-7 groups, preferably with 1-3 groups selected from the groups indicated above as the substituents for the alkyl group.

As used herein, the term "$(C_1-C_8)$-alkoxy" or "alkoxy", whether used alone or as part of a substituent group, refers to a $(C_1-C_8)$-alkyl having an oxygen radical attached thereto.

The term "$(C_1-C_8)$-alkoxy" or "O—$(C_1-C_8)$-alkyl" or "alkoxy" wherever used in this specification have the same meaning. Representative examples of alkoxy groups include, but are not limited to, methoxy, ethoxy, propoxy, isopropoxy, n-butoxy, isobutoxy and t-butoxy. Furthermore, unless stated otherwise, the alkoxy groups can be unsubstituted or substituted with one or more groups. A substituted alkoxy refers to a $(C_1-C_8)$-alkoxy substituted with 1-7 groups, preferably with 1-3 groups selected from the groups indicated above as the substituents for the alkyl group.

As used herein, the term "halo$(C_1-C_8)$alkoxy" or "haloalkoxy", whether used alone or as part of a substituent group, refers to the alkoxy group which is substituted with one or more halogens. A monohalo$(C_1-C_8)$alkoxy radical, for example, can have a chlorine, bromine, iodine or fluorine atom. Dihalo- or polyhalo$(C_1-C_8)$alkoxy radicals can have two or more of the same or different halogen atoms. Representative examples of halo$(C_1-C_8)$alkoxy include, but are not limited to, chloromethoxy, dichloromethoxy, trichloromethoxy, dichloroethoxy, dichloropropoxy, fluoromethoxy, difluoromethoxy, trifluoromethoxy, pentafluoroethoxy, heptafluoropropoxy, difluorochloromethoxy, dichlorofluoromethoxy, difluoroethoxy, difluoropropoxy or the like groups.

As used herein, the term "$(C_3-C_{12})$-cycloalkyl" or "cycloalkyl", whether used alone or as part of a substituent group, refers to a saturated cyclic hydrocarbon radical including 1, 2 or 3 rings including a total of 3 to 12 carbon atoms forming the rings, which can be unsubstituted or substituted with one or more substituents. The term cycloalkyl includes bridged, fused and spiro ring systems. As used herein, $(C_3-C_{12})$-cycloalkyl refers to a cycloalkyl group having 3 to 12 (both inclusive) carbon atoms; preferably, can refer to cycloalkyl group having 3 to 10 (both inclusive) carbon atoms i.e. $(C_3-C_{10})$-cycloalkyl; and more preferably, can refer to cycloalkyl group having 3 to 7 (both inclusive) carbon atoms i.e. $(C_3-C_7)$-cycloalkyl. Representative examples of cycloalkyl include, but are not limited to, cyclopropyl, cyclobutyl, cyclopentyl, cyclohexyl, adamantyl, norbornyl, bicyclo[2.1.0]pentane, bicyclo[2.2.1]heptyl, and spiro[3.3]heptanes.

As used herein, the term "$(C_5-C_{10})$-cycloalkenyl" or "cycloalkenyl", whether used alone or as part of a substituent group, refers to a partially unsaturated monocyclic hydrocarbon radical containing a total of 5 to 10 carbon atoms forming the ring, which can be unsubstituted or substituted with one or more substituents. Representative examples of $(C_5-C_{10})$-cycloalkenyl include, but are not limited to, cyclopentenyl, cyclohexenyl, 1,2,3,3a-tetrahydropentalenyl and 1,2,3,4-tetrahydronaphthalenyl.

Furthermore, unless stated otherwise, "the cycloalkyl" or "the cycloalkenyl" group can be unsubstituted or substituted with one or more groups; preferably with 1-7 groups, more preferably with 1-3 groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$ alkoxy, $C(O)R^h$, $COOR^h$, $C(O)NR^hR^i$, $O\!\!-\!\!R^i$, $OC(O)R^h$, $OC(O)NR^hR^i$, $NR^hR^i$, $NR^hC(O)R^i$, $NR^hC(O)NR^hR^i$, $S(O)_q$ $(C_1-C_8)$-alkyl, $S(O)_rNR^hR^i$ and $NR^hS(O)_qR^i$; wherein $R^h$ and $R^i$ are as defined above.

The term "$(C_6-C_{10})$-aryl" or "aryl", whether used alone or as part of a substituent group, refers to monocyclic or bicyclic hydrocarbon groups having 6 to 10 ring carbon atoms in which the carbocyclic ring(s) present have a conjugated pi electron system, which may be optionally substituted by one or more groups. Representative examples of $(C_6-C_{10})$-aryl include, but are not limited to, phenyl or naphthyl.

Furthermore, unless stated otherwise, the aryl group can be unsubstituted or substituted with one or more groups. A substituted aryl refers to a $(C_6-C_{10})$-aryl substituted with one or more groups, preferably 1-7 groups and more preferably 1-3 groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, $C(O)R^h$, $COOR^h$, $C(O)NR^hR^i$, $O-R^i$, $OC(O)R^h$, $OC(O)NR^hR^i$, $NR^hR^i$, $NR^hC(O)R^i$, $NR^hC(O)NR^hR^i$, $S(O)_q(C_1-C_8)$-alkyl, $S(O)_rNR^hR^i$ and $NR^hS(O)_qR^i$; wherein $R^h$ and $R^i$ are as defined above.

As used herein, the term "$(C_6-C_{10})$-aryl-$(C_1-C_8)$-alkyl" or "ar-$(C_1-C_8)$-alkyl" refers to an alkyl group substituted with an $(C_6-C_{10})$-aryl group, wherein the terms alkyl and aryl are as defined above. Representative example of aralkyl group include $(CH_2)_p$-phenyl, wherein p is an integer from 1 to 6, such as benzyl wherein p is 1. The aryl of the $(C_6-C_{10})$-aralkyl group can be unsubstituted or substituted with groups selected from the groups indicated above as the substituents for the aryl group.

The term "heteroatom" as used herein, includes nitrogen (N), oxygen (O) and sulfur (S). Any heteroatom with unsatisfied valency is assumed to have a hydrogen atom to satisfy the valency.

As used herein, the term "heterocyclyl" or "heterocyclic", whether used alone or as part of a substituent group, refers to a 3- to 10-membered saturated, partially unsaturated, monocyclic or bicyclic ring system containing 1 to 4 identical or different heteroatoms independently selected from the group consisting of oxygen, nitrogen and sulfur. Saturated heterocyclic ring systems do not contain any double bond, whereas partially unsaturated heterocyclic ring systems, contain at least one double bond, but do not form an aromatic system containing a hetero atom. Representative examples of heterocyclyl include, but are not limited to, pyrrolyl, pyrrolidinyl, pyrazolyl, imidazolyl, pyranyl, tetrahydropyranyl, pyrazinyl, piperazinyl, oxetanyl, oxazolyl, oxadiazolyl, isoxazolyl, triazolyl, thiazolyl, tetrazolyl, furyl, thienyl, purinyl, pyridinyl, pyridazinyl, pyrimidinyl, piperidyl, benzoxazolyl, benzothiazolyl, benzofuranyl, purinyl, benzimidazolyl, benzoxazolyl, indolyl, indazolyl, isoindolyl, isothiazolyl, isoquinolyl, morpholinyl, thiomorpholinyl, thiomorpholinyl-1,1-dioxide, quinoxalinyl, quinolinyl and thiophenyl. The oxidized form of the ring nitrogen and sulfur atom contained in the heterocyclyl to provide the corresponding N-oxide, S-oxide or S,S-dioxide is also encompassed in the scope of the present invention.

Furthermore, unless stated otherwise, the heterocyclyl group can be unsubstituted or substituted with one or more groups, preferably with 1-7 groups, more preferably with 1-3 groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, $C(O)R^h$, $COOR^h$, $C(O)NR^hR^i$, $O-R^i$, $OC(O)R^h$, $OC(O)NR^hR^i$, $NR^hR^i$, $NR^hC(O)R^i$, $NR^hC(O)NR^hR^i$, $S(O)_q(C_1-C_8)$-alkyl, $S(O)_rNR^hR^i$ and $NR^hS(O)_qR^i$; wherein $R^h$ and $R^i$ are as defined above.

As used herein, the term "heteroaryl", whether used alone or as part of a substituent group, refers to 5- to 10-membered heterocyclyl having an aromatic ring containing one to four identical or different hetero atoms selected from the group consisting of nitrogen, sulphur and oxygen atom. Representative examples of heteroaryl include, but are not limited to, pyrrole, pyrazole, imidazole, pyrazine, furan, thiophene, oxazole, oxadiazole, thiazole, benzimidazole, benzoxazole, benzothiazole, benzofuran, indole, indazole, isoindole, isoquinoline, isooxazole, triazine, purine, pyridine, quinoline, oxadiazole, thiene, pyridazine, pyrimidine, isothiazole, quinoxaline (benzopyrazine), tetrazole, pyrido[2,3-b]pyrazine. The oxidized form of the ring nitrogen and sulfur atom contained in the heteroaryl to provide the corresponding N-oxide, S-oxide or S,S-dioxide is also encompassed in the scope of the present invention.

Furthermore, unless stated otherwise, the heteroaryl groups can be unsubstituted or substituted with one or more groups; preferably with 1-7 groups, more preferably with 1-3 groups selected from the groups indicated above as the substituents for the heterocyclyl group.

Within the context of this present invention and as used herein the term "isotopic forms" or "isotopically labeled forms" is a general term used for isotopic forms of the compound of formula I, wherein one or more atoms of the compound of formula I are replaced by their respective isotopes. All isotopes of any particular atom or element as specified are contemplated within the scope of the compounds of the present invention.

Examples of isotopes that may be incorporated into the compounds disclosed herein include, but are not limited to, isotopes of hydrogen such as $^2H$ (deuterium or D) and $^3H$ (tritium or T), carbon such as $^{11}C$, $^{13}C$ and $^{14}C$, nitrogen such as $^{13}N$ and $^{15}N$, oxygen such as $^{15}O$, $^{17}O$ and $^{18}O$, chlorine such as $^{36}Cl$, fluorine such as $^{18}F$ and sulphur such as $^{35}S$. Substitution with heavier isotopes, for example, replacing one or more key carbon-hydrogen bonds with carbon-deuterium bond, may show certain therapeutic advantages, resulting from longer metabolism cycles (e.g., increased in vivo half life or reduced dosage requirements), improved safety or greater effectiveness and hence, may be preferred in certain circumstances.

Representative examples of isotopic forms of a compound of formula I can include, without limitation, deuterated compound of formula I. The term "deuterated" as used herein, by itself or used to modify a compound or group, refers to replacement of one or more hydrogen atom(s), which is attached to carbon(s), with a deuterium atom. For example, the compounds of formula I can include in the definitions of one or more of its various variables, wherever applicable, deuterium, deuterated-alkyl, deuterated-alkoxy, deuterated-cycloalkyl, deuterated-aryl, deuterated-heterocyclyl, deuterated-heteroaryl and the like. The term "deuterated-alkyl" refers to $(C_1-C_8)$-alkyl group as defined herein, wherein at least one hydrogen atom bound to carbon is replaced by deuterium. That is, in a deuterated alkyl group, at least one carbon atom is bound to deuterium. In a deuterated alkyl group, it is possible for a carbon atom to be bound to more than one deuterium; it is also possible that more than one carbon atom in the alkyl group is bound to deuterium. Analogously, the term "deuterated" and the terms deuterated-heterocyclyl, deuterated-heteroaryl, deuterated-cycloalkyl, deuterated-aryl and deuterated-alkoxy each refer to the corresponding chemical moiety wherein at least one carbon is bound to deuterium.

The term "pharmaceutically acceptable solvate(s)" or "solvate(s)" as used herein refers to a compound formed by the interaction of a solute (in the present invention, a compound of formula I or a pharmaceutically acceptable salt thereof) and a solvent. Such solvents for the purpose of the invention may not interfere with the biological activity of the solute. Preferably, the solvent used is a pharmaceutically acceptable solvent. Examples of suitable pharmaceutically acceptable solvents include, without limitation, water, ethanol and acetic acid or a mixture thereof. Preferably, the solvent used is water and the solvates obtained are referred to as hydrates. Examples for suitable solvates are the mono- or di-hydrates or alcoholates of the compounds of the present invention.

Within the context of the present invention and as used herein, the term "stereoisomer" or "stereoisomeric form" is a general term used for all isomers of individual compounds (in the present invention, a compound of formula I) that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers).

The term "tautomer" refers to the coexistence of two or more compounds that differ from each other only in the position of one (or more) mobile atoms and in electron distribution, for example, keto-enol tautomers or amide-imidic acid tautomers.

As used herein, the term "pharmaceutically acceptable" means that the carrier, diluent, excipient, and/or salt must be compatible with the other ingredients of the formulation, and not deleterious to the recipient thereof.

The term "pharmaceutically acceptable salt(s)" as used herein includes a salt or salts of the active compound i.e. the compound of formula I, which retain the desired biological activity of the subject compound and exhibit minimal undesired toxicological effects; and are prepared using suitable acids or bases, depending on the particular substituents found on the compounds described herein.

Within the context of the present invention and as used herein the term "polymorph" or "polymorphic form" refers to crystals of the same compound that differs only in the arrangement and/or conformation of the molecule (in the present invention, a compound of formula I) in the crystal lattice.

Within the context of the present invention and as used herein, "N-oxide" refers to the oxide of the nitrogen atom of a nitrogen-containing heteroaryl or heterocycle. N-oxide can be formed in the presence of an oxidizing agent such as m-chloroperbenzoic acid or hydrogen peroxide. N-oxide refers to an amine oxide, also known as amine-N-oxide, and is a chemical compound that contains N→O bond.

Within the context of the present invention and as used herein "S-oxide" refers to the oxide of the sulfur atom (S-oxide) or dioxide of the sulfur atom (S,S-dioxide) of a sulfur-containing heteroaryl or heterocycle. S-oxide and S, S-dioxides can be formed in the presence of an oxidizing agent for example, peroxide such as m-chloroperbenzoic acid or oxone.

Within the context of the present invention and as used herein, "a prodrug" or "prodrugs" refers to any compound, which are derivatives of a parent compound (in the context of the present invention, a compound of formula I), which following administration, release(s) the parent compound in vivo via a chemical or physiological process, e.g., a prodrug on being brought to the physiological pH or through enzyme action is converted to the parent compound.

In the context of the present invention, the term "compound(s) of formula I" or "compounds of the present invention" are used interchangeably and unless indicated otherwise, includes all the isotopic forms, stereoisomeric and tautomeric forms and mixtures thereof in all ratios, and pharmaceutically acceptable salts, solvates, polymorphs, prodrugs, N-oxides and S-oxides thereof. The compound(s) of formula I can also be referred to herein as "the active compound" or "the active ingredient".

The term "RORγ" refers to all isoforms encoded by the RORc gene which include RORγ1 and RORγt (RORγ2).

The term "RORγ modulator" refers to an agent (in the context of the present invention, a compound of formula I) that modulates directly or indirectly the activity of RORγ. In other words, RORγ modulator is a compound which is capable of interacting, either directly or indirectly, with RORγ receptor and initiates the pharmacological or biochemical response. RORγ modulators include antagonist and inverse agonist of RORγ.

The term, "disease or disorder mediated by RORγ" refers to a disease or disorder in a subject caused due to the uncontrolled expression or dysfunction of the RORγ or Th-17 cells.

The diseases or disorders mediated by RORγ can be selected from autoimmune diseases, inflammatory diseases, metabolic diseases, and cancer.

The term, "therapeutically effective amount" as used herein means an amount of a compound of formula I or a pharmaceutically acceptable salt thereof; or a composition comprising a compound of formula I or a pharmaceutically acceptable salt thereof, effective in producing the desired therapeutic response in a particular patient (subject) suffering from a disease or disorder mediated by RORγ such as an autoimmune disease, an inflammatory disease or a metabolic disease. Particularly, the term "therapeutically effective amount" includes the amount of a compound (in the context of the present invention, the compound of Formula I or a pharmaceutically acceptable salt thereof), when administered, that induces a positive modification in the disease or disorder to be treated or is sufficient to prevent development of, or alleviate to some extent one or more of the symptoms of the disease or disorder being treated in a subject. In respect of the therapeutic amount of the compound, consideration is also given that the amount of the compound used for the treatment of a subject is low enough to avoid undue or severe side effects, within the scope of sound medical judgment. The therapeutically effective amount of the compound or composition will vary with the particular condition (in the context of the present invention, the disease or disorder that is mediated by RORγ) being treated, the age and physical condition of the subject, the severity of the condition being treated or prevented, the duration of the treatment, the nature of concurrent therapy, the specific compound or composition employed, the particular pharmaceutically acceptable carrier utilized and other related factors.

As used herein, the term "pharmaceutically acceptable carrier" refers to a material that is non-toxic, inert, solid, semi-solid or liquid filler, diluent, encapsulating material or formulation auxiliary or excipient of any type which is suitable for a subject, preferably a mammal, more preferably a human, and is suitable for delivering an active agent to the target site without affecting the activity of the agent.

The term "subject" as used herein refers to an animal, preferably a mammal, and most preferably a human. The term "mammal" used herein refers to warm-blooded vertebrate animals of the class 'mammalia', including humans, characterized by a covering of hair on the skin and, in the female, milk-producing mammary glands for nourishing the young. The term mammal includes animals such as cat, dog, rabbit, bear, fox, wolf, monkey, deer, mouse, pig and human. The term "subject" may be used interchangeably with the term patient. In the context of the present invention the phrase "a subject in need thereof" means a subject (patient) in need of the treatment for the disease or disorder that is mediated by RORγ. Alternatively, the phrase "a subject in need thereof" means a subject (patient) diagnosed having a disease or disorder that is mediated by RORγ.

As used herein, the terms "treatment" "treat" and "therapy" and the like mean to alleviate, slow the progression, attenuation, prophylaxis or as such treat the existing diseases or condition (e.g. autoimmune, inflammatory or metabolic diseases). Treatment also includes treating, preventing development of, or alleviating to some extent, one or more of the symptoms of the diseases or condition.

EMBODIMENTS

The invention encompasses all the compounds described by the formula I without limitation, however, for the purposes of further illustrations, preferred aspects and elements of the invention are discussed herein the form of the following embodiments.

In an embodiment, the present invention relates to a compound of formula I; wherein: $R^1$ is $—S(O)_mR^a$, $—S(O)_rNR^bR^c$, $—S(O)_r(NR^b)R^a$, $—NR^bCOR^c$, $—NR^bS(O)_mR^a$ or $—NR^bS(O)_rNR^bR^c$;

$R^a$, $R^b$, $R^c$, r and m are as defined in the first aspect of the invention;

provided that, (i) when $R^1$ is $—S(O)_rNR^bR^c$, wherein $R^b$ and $R^c$ can combine to form a saturated or unsaturated 5- or 6-membered ring, then Q is

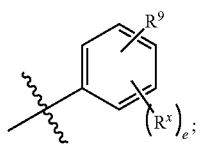

or (ii) when $R^1$ is $NR^bCOR^c$, wherein $R^b$ is hydrogen and $R^c$ is $(C_1-C_8)$-alkyl, then Q is

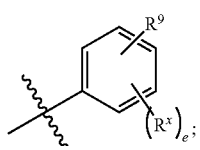

or an isotopic form, a stereoisomer, a tautomer, a pharmaceutically acceptable salt, a pharmaceutically acceptable solvate, a polymorph, a prodrug, N-oxide or S-oxide thereof.

In an embodiment, the present invention relates to a compound of formula I, wherein:
$R^1$ is $—O—R^d$ or

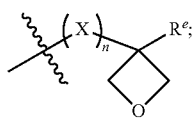

$R^d$, $R^e$, X and n are as defined in the first aspect of the invention;

or an isotopic form, a stereoisomer or a tautomer or a pharmaceutically acceptable salt, a pharmaceutically acceptable solvate, a polymorph, a prodrug, N-oxide or S-oxide thereof.

In an embodiment, the present invention relates to a compound of formula I, wherein: $R^1$ is $—S(O)_mR^a$, $—S(O)_rNR^bR^c$ or $—S(O)_r(NR^b)R^a$;

$R^a$, $R^b$, $R^c$, r and m are as defined in the first aspect of the invention;

provided that, when $R^1$ is $—S(O)_rNR^bR^c$, wherein $R^b$ and $R^c$ can combine to form a saturated or unsaturated 5- or 6-membered ring, then Q is

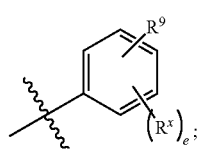

or an isotopic form, a stereoisomer, a tautomer, a pharmaceutically acceptable salt, a pharmaceutically acceptable solvate, a polymorph, a prodrug, N-oxide or S-oxide thereof.

In an embodiment, the present invention relates to a compound of formula I, wherein: $R^1$ is $—NR^bCOR^c$, $—NR^bS(O)_mR^a$ or $—NR^bS(O)_rNR^bR^c$;

$R^a$, $R^b$, $R^c$, m and r are as defined in first aspect of the invention;

provided that, when $R^1$ is $NR^bCOR^c$, wherein $R^b$ is hydrogen and $R^c$ is $(C_1-C_8)$-alkyl, then Q is

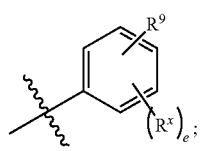

or an isotopic form, a stereoisomer, a tautomer, a pharmaceutically acceptable salt, a pharmaceutically acceptable solvate, a polymorph, a prodrug, N-oxide or S-oxide thereof.

In an embodiment, the present invention relates to a compound of formula I, wherein: L is $—CO—$;

or an isotopic form, a stereoisomer, a tautomer, a pharmaceutically acceptable salt, a pharmaceutically acceptable solvate, a polymorph, a prodrug, N-oxide or S-oxide thereof.

In an embodiment, the present invention relates to a compound of formula I, wherein: L is $—S(O)_2—$;

or an isotopic form, a stereoisomer, a tautomer, a pharmaceutically acceptable salt, a pharmaceutically acceptable solvate, a polymorph, a prodrug, N-oxide or S-oxide thereof.

In an embodiment, the present invention relates to a compound of formula I, wherein: A is

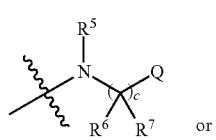

or

-continued

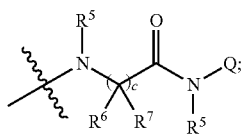
A-2 wherein $R^5$, $R^6$, $R^7$, c and Q are as defined in the first aspect of the invention;

or an isotopic form, a stereoisomer, a tautomer, a pharmaceutically acceptable salt, a pharmaceutically acceptable solvate, a polymorph, a prodrug, N-oxide or S-oxide thereof.

In an embodiment, the present invention relates to a compound of formula I, wherein: A is

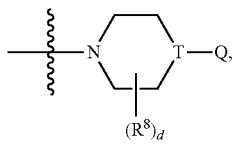
A-3

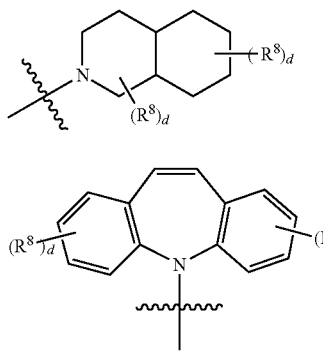
A-4

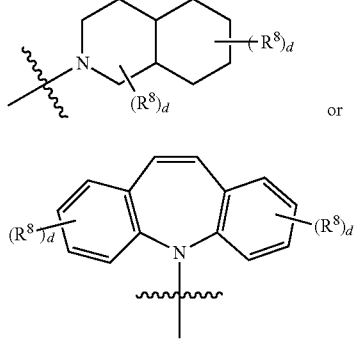
A-5 wherein $R^8$, T, Q and d are as defined in the first aspect of the invention;

or an isotopic form, a stereoisomer, a tautomer, a pharmaceutically acceptable salt, a pharmaceutically acceptable solvate, a polymorph, a prodrug, N-oxide or S-oxide thereof.

In another embodiment, the present invention relates to a compound of formula I, wherein: Q is

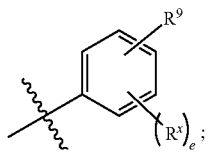
Q-1 wherein $R^9$, $R^x$ and e are as defined in the first aspect of the invention;

or an isotopic form, a stereoisomer, a tautomer, a pharmaceutically acceptable salt, a pharmaceutically acceptable solvate, a polymorph, a prodrug, N-oxide or S-oxide thereof.

In another embodiment, the present invention relates to a compound of formula I, wherein: Q is

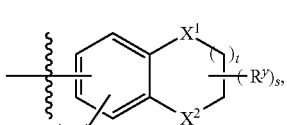
Q-2

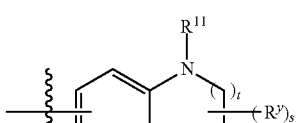
Q-3 or

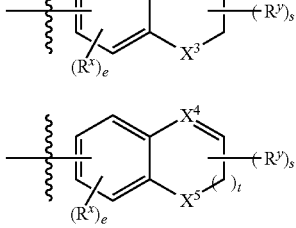
Q-4 wherein $R^{10}$, $R^y$, o and s are as defined in the first aspect of the invention;

or an isotopic form, a stereoisomer, a tautomer, a pharmaceutically acceptable salt, a pharmaceutically acceptable solvate, a polymorph, a prodrug, N-oxide or S-oxide thereof.

In another embodiment, the present invention relates to a compound of formula I, wherein: Q is

Q-5

Q-6 or

Q-7 wherein $R^x$, $R^{11}$, $X^1$, $X^2$, $X^3$, $X^4$, $X^5$, t, e and s are as defined in the first aspect of the invention; or an isotopic form, a stereoisomer, a tautomer, a pharmaceutically acceptable salt, a solvate, a polymorph, a prodrug, N-oxide or S-oxide thereof.

In another embodiment, the present invention relates to a compound of formula I, wherein: Q is

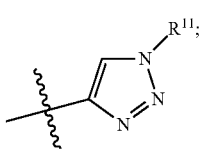
Q-8 wherein $R^{11}$ is as defined in the first aspect of the invention;

or an isotopic form, a stereoisomer, a tautomer, a pharmaceutically acceptable salt, a pharmaceutically acceptable solvate, a polymorph, a prodrug, N-oxide or S-oxide thereof.

In yet another embodiment, the present invention relates to a compound of formula I, wherein: A is

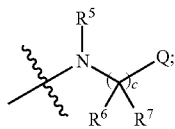

A-1 and

Q is

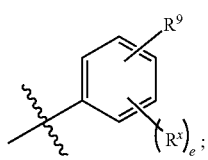

Q-1 wherein $R^5$, $R^6$, $R^7$, $R^9$, $R^x$, c and e are as defined in the first aspect of the invention;

or an isotopic form, a stereoisomer, a tautomer, a pharmaceutically acceptable salt, a pharmaceutically acceptable solvate, a polymorph, a prodrug, N-oxide or S-oxide thereof.

In yet another embodiment, the present invention relates to a compound of formula I, wherein: A is

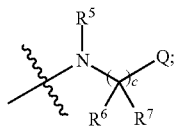

A-1 and

Q is

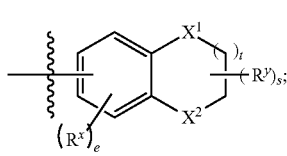

Q-5 wherein $R^5$, $R^6$, $R^7$, $R^x$, $R^y$, $X^1$, $X^2$, c, e, t and s are as defined in the first aspect of the invention;

or an isotopic form, a stereoisomer, a tautomer or a pharmaceutically acceptable salt, a pharmaceutically acceptable solvate, a polymorph, a prodrug, N-oxide or S-oxide thereof.

In another embodiment, the present invention relates to a compound of formula I, wherein:
$R^1$ is $-S(O)_mR^a$;
A is

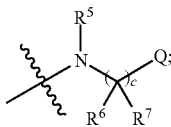

A-1 and

Q is

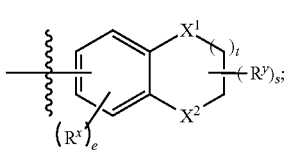

Q-5 wherein $X^1$ is $CR^{12}R^{13}$, $X^2$ is $CR^{14}R^{15}$; $R^{14}$ and $R^{15}$ are hydrogen; $R^a$, $R^5$, $R^6$, $R^7$, $R^{12}$, $R^{13}$, $R^x$, $R^y$, c, e, m, t and s are as defined in the first aspect of the invention;

or an isotopic form, a stereoisomer, a tautomer, a pharmaceutically acceptable salt, a pharmaceutically acceptable solvate, a polymorph, a prodrug, N-oxide or S-oxide thereof.

In another embodiment, the present invention relates to a compound of formula I, wherein:
$R^1$ is $-S(O)_mR^a$;
L is $-CO-$;
A is

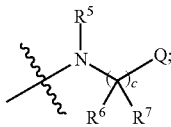

A-1 and

Q is

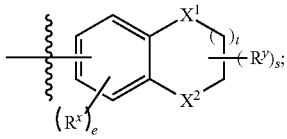

Q-5 wherein $X^1$ is $CR^{12}R^{13}$, $X^2$ is $CR^{14}R^{15}$; $R^{14}$ and $R^{15}$ are hydrogen; $R^a$, $R^5$, $R^6$, $R^7$, $R^{12}$, $R^{13}$, $R^x$, $R^y$, m, c, e, t and s are as defined in the first aspect of the invention;

or an isotopic form, a stereoisomer, a tautomer, a pharmaceutically acceptable salt, a solvate, a polymorph, a prodrug, N-oxide or S-oxide thereof.

Representative compounds of formula I encompassed in accordance with the present invention include:
2-(4-(Ethylsulfonyl)phenyl)-N-(4-(1,1,1,3,3,3-hexafluoro-2-methoxypropan-2-yl)phenyl) acetamide;

N-(1,1-Dioxido-4-oxothiochroman-6-yl)-2-(4-(ethylsulfonyl)phenyl)acetamide;
2-(4-(Ethylsulfonyl)phenyl)-N-(4-oxothiochroman-6-yl)acetamide;
N-(4-Cyclohexyl-2-(1,1,1,3,3,3-hexafluoro-2-hydroxypropan-2-yl)phenyl)-2-(4-(ethyl sulfonyl)phenyl)acetamide;
N-(4-(1-Cyanocyclopropyl)phenyl)-2-(4-(ethylsulfonyl)phenyl)acetamide;
2-(4-(Ethylsulfonyl)phenyl)-N-(4-(1,1,1,3,3,3-hexafluoro-2-(4-phenylbutoxy)propan-2-yl)phenyl)acetamide;
2-(4-(Ethylsulfonyl)phenyl)-N-(4-(1,1,1,3,3,3-hexafluoro-2-hydroxypropan-2-yl)-2-methylphenyl)acetamide;
2-(4-(Ethylsulfonyl)phenyl)-N-(3-(1,1,1,3,3,3-hexafluoro-2-hydroxypropan-2-yl)phenyl) acetamide;
2-(4-(Ethylsulfonyl)phenyl)-N-(4-(1,1,1-trifluoro-2-hydroxypropan-2-yl)phenyl) acetamide;
2-(4-(Ethylsulfonyl)phenyl)-N-(4-(2,2,2-trifluoro-1-hydroxyethyl)phenyl)acetamide;
N-(4-(2-(2-Cyclohexylethoxy)-1,1,1,3,3,3-hexafluoropropan-2-yl)phenyl)-2-(4-(ethyl sulfonyl)phenyl)acetamide;
2-(4-(Ethylsulfonyl)phenyl)-N-(4-(1,1,1,3,3,3-hexafluoro-2-(2-(piperidin-1-yl)ethoxy) propan-2-yl)phenyl)acetamide;
2-(4-(Ethylsulfonyl)phenyl)-N-(4-(1,1,1,3,3,3-hexafluoro-2-hydroxypropan-2-yl) phenyl)acetamide;
2-(4-(Ethylsulfonyl)phenyl)-1-(4-(4-(1,1,1,3,3,3-hexafluoro-2-hydroxypropan-2-yl) phenyl)piperazin-1-yl)ethanone;
2-(4-(Ethylsulfonyl)phenyl)-N-(5-oxo-5,6,7,8-tetrahydronaphthalen-2-yl)acetamide;
2-(4-(Ethylsulfonyl)phenyl)-N-(5,6,7,8-tetrahydronaphthalen-2-yl)acetamide;
N-(4-(2-Cyanopropan-2-yl)phenyl)-2-(4-(ethylsulfonyl)phenyl)acetamide;
2-(4-(Ethylsulfonyl)phenyl)-N-(3-(1,1,1,3,3,3-hexafluoro-2-hydroxypropan-2-yl)-5,6,7,8-tetrahydronaphthalen-2-yl)acetamide;
2-(4-(Ethylsulfonyl)phenyl)-N-(4-phenylcyclohexyl)acetamide;
N-(4-(1,1,1,3,3,3-Hexafluoro-2-hydroxypropan-2-yl)phenyl)-2-(4-(2-oxopyrrolidin-1-yl) phenyl)acetamide;
2-(4-Acetamidophenyl)-N-(4-(1,1,1,3,3,3-hexafluoro-2-hydroxypropan-2-yl)phenyl) acetamide;
N-(4-(2-((4-(1,1,1,3,3,3-Hexafluoro-2-hydroxypropan-2-yl) phenyl)amino)-2-oxoethyl) phenyl)-N-methylpivalamide;
N-(4-(Cyclohexyloxy)-3-(trifluoromethyl)phenyl)-2-(4-(ethylsulfonyl)phenyl) acetamide;
2-(4-(Ethylsulfonyl)phenyl)-N-(4'-oxo-2-(trifluoromethyl)-2',3',4',5'-tetrahydro-[1,1'-biphenyl]-4-yl)acetamide;
N-(4-Cyclohexylphenyl)-2-(4-(ethylsulfonyl)phenyl)acetamide;
2-(4-(Ethylsulfonyl)phenyl)-N-(4-(1,1,1,3,3,3-hexafluoro-2-hydroxypropan-2-yl)benzyl) acetamide;
N-(4-(1,1,1,3,3,3-Hexafluoro-2-hydroxypropan-2-yl)phenyl)-2-(4-(morpholinosulfonyl) phenyl)acetamide;
N-(5-Cyclohexylidene-5,6,7,8-tetrahydronaphthalen-2-yl)-2-(4-(ethylsulfonyl)phenyl) acetamide;
2-(4-(Ethylsulfonyl)phenyl)-N-(4-oxociroman-6-yl)acetamide;
N-(4-(1,1,1,3,3,3-Hexafluoro-2-hydroxypropan-2-yl)phenyl)-2-(thiochroman-6-yl) acetamide;
N-(4-Ethyl-3-oxo-3,4-dihydro-2H-benzo[b][1,4]oxazin-7-yl)-2-(4-(ethylsulfonyl) phenyl)acetamide;
2-(4-(Ethylsulfonyl)phenyl)-N-(4-(4-methoxybenzyl)-3-oxo-3,4-dihydro-2H-benzo [b][1,4]oxazin-7-yl)acetamide;
2-(4-(Ethylsulfonyl)phenyl)-N-(4-hydroxythiochroman-6-yl)acetamide;
2-(4-(Ethylsulfonyl)phenyl)-N-(4'-hydroxy-2-(trifluoromethyl)-2',3',4',5'-tetrahydro-[1,1'-biphenyl]-4-yl)acetamide;
N-(5-Cyclohexyl-5,6,7,8-tetrahydronaphthalen-2-yl)-2-(4-(ethylsulfonyl)phenyl) acetamide;
2-(4-(Ethylsulfonyl)phenyl)-N-(4-hydroxychroman-6-yl)acetamide;
N-(7,8-Dihydronaphthalen-2-yl)-2-(4-(ethylsulfonyl)phenyl)acetamide;
2-(4-(Ethylsulfonyl)phenyl)-N-(5-hydroxy-5,6,7,8-tetrahydronaphthalen-2-yl)acetamide;
2-(4-(Ethylsulfonyl)phenyl)-N-(4-(1-hydroxy-1-phenylethyl)phenyl) acetamide;
N-(4-Ethyl-4-hydroxychroman-6-yl)-2-(4-(ethylsulfonyl) phenyl)acetamide;
N-(5-(tert-Butyl)-5-hydroxy-5,6,7,8-tetrahydronaphthalen-2-yl)-2-(4-(ethylsulfonyl) phenyl)acetamide;
2-(4-(Ethylsulfonyl)phenyl)-N-(5-hydroxy-5-phenyl-5,6,7,8-tetrahydronaphthalen-2-yl) acetamide;
2-(4-(Ethylsulfonyl)phenyl)-N-(5-hydroxy-5-(4-methoxyphenyl)-5,6,7,8-tetrahydro naphthalen-2-yl)acetamide;
2-(4-(Ethylsulfonyl)phenyl)-N-(5-hydroxy-5-vinyl-5,6,7,8-tetrahydronaphthalen-2-yl) acetamide;
2-(4-(Ethylsulfonamido)phenyl)-N-(4-(1,1,1,3,3,3-hexafluoro-2-hydroxypropan-2-yl) phenyl)acetamide;
N-(4-(1,1,1,3,3,3-Hexafluoro-2-hydroxypropan-2-yl)phenyl)-2-(4-(4-(trifluoromethyl) phenylsulfonamido)phenyl)acetamide;
2-(4-(Ethylsulfonyl)phenyl)-N-(4-(perfluoropropan-2-yl) phenyl)acetamide;
N-(Cyclopropylmethyl)-2-(4-(ethylsulfonyl)phenyl)-N-(4-(1,1,1,3,3,3-hexafluoro-2-hydroxypropan-2-yl)phenyl) acetamide;
2-(4-(Ethylsulfonimidoyl)phenyl)-N-(3-(1,1,1,3,3,3-hexafluoro-2-hydroxypropan-2-yl)phenyl)acetamide
N-(4-(2-Cyano-1,1,1,3,3,3-hexafluoropropan-2-yl)phenyl)-2-(4-(ethylsulfonimidoyl) phenyl)acetamide;
2-(4-(Ethylsulfonimidoyl)phenyl)-N-(4-(1,1,1,3,3,3-hexafluoro-2-hydroxypropan-2-yl)-2-methylphenyl)acetamide;
N-(4-(2-Ethoxy-1,1,1,3,3,3-hexafluoropropan-2-yl)phenyl)-2-(4 (ethylsulfonimidoyl) phenyl)acetamide;
N-(4-(2-Ethoxy-1,1,1,3,3,3-hexafluoropropan-2-yl)phenyl)-2-(4-(ethylsulfonyl) phenyl)acetamide;
2-(4-(Ethylsulfonyl)phenyl)-N-(4-(1,1,1,3,3,3-hexafluoro-2-isopropoxypropan-2-yl)phenyl)acetamide;
2-(4-(Ethylsulfonyl)phenyl)-N-(4-(1,1,1,3,3,3-hexafluoro-2-propoxypropan-2-yl)phenyl)acetamide;
N-(4-(2-(Cyclopentylmethoxy)-1,1,1,3,3,3-hexafluoropropan-2-yl)phenyl)-2-(4-(ethyl sulfonyl)phenyl)acetamide;
2-(4-(Ethylsulfonyl)phenyl)-N-(4-(1,1,1,3,3,3-hexafluoro-2-(prop-2-yn-1-yloxy) propan-2-yl)phenyl)acetamide;
2-(4-(Ethylsulfonyl)phenyl)-N-(4-(1,1,1,3,3,3-hexafluoro-2-(pyridin-2-ylmethoxy) propan-2-yl)phenyl)acetamide;
2-(4-(Ethylsulfonyl)phenyl)-N-(4-(1,1,1,3,3,3-hexafluoro-2-(pyridin-2-ylmethoxy) propan-2-yl)phenyl)acetamide hydrochloride;
2-(4-(Ethylsulfonyl)phenyl)-N-(4-(1,1,1,3,3,3-hexafluoro-2-methoxypropan-$D_3$-2-yl)phenyl) acetamide;
2-(4-(Ethylsulfonyl)phenyl)-N-(4-(1,1,1,3,3,3-hexafluoro-2-(2-methoxyethoxy) propan-2-yl)phenyl)acetamide;
N-(4-(2-(Cyclopropylmethoxy)-1,1,1,3,3,3-hexafluoropropan-2-yl)phenyl)-2-(4-(ethylsulfonyl)phenyl)acetamide;
2-(4-(Ethylsulfonyl)phenyl)-N-(4-(1,1,1,3,3,3-hexafluoro-2-isobutoxypropan-2-yl)phenyl)acetamide;

Methyl 2-((2-(4-(2-(4-(ethylsulfonyl)phenyl)acetamido)phenyl)-1,1,1,3,3,3-hexafluoro propan-2-yl)oxy)acetate;
N-(4-(2-(Cyclobutylmethoxy)-1,1,1,3,3,3-hexafluoropropan-2-yl)phenyl)-2-(4-(ethylsulfonyl)phenyl)acetamide;
2-(4-(Ethylsulfonyl)phenyl)-N-(4-(1,1,1,3,3,3-hexafluoro-2-(1H-pyrazol-1-yl)propan-2-yl)phenyl)acetamide;
N-(4-(1,1,1,3,3,3-Hexafluoro-2-hydroxypropan-2-yl)phenyl)-2-(4-(methylsulfonyl) phenyl)acetamide;
2-(4-(N,N-Dimethylsulfamoyl)phenyl)-N-(4-(1,1,1,3,3,3-hexafluoro-2-(pyridin-2-ylmethoxy)propan-2-yl)phenyl)acetamide;
N-Ethyl-2-(4-(ethylsulfonyl)phenyl)-N-(4-(1,1,1,3,3,3-hexafluoro-2-hydroxypropan-2-yl)phenyl)acetamide;
2-(4-(Ethylsulfonyl)phenyl)-N-(4-(1,1,1,3,3,3-hexafluoro-2-hydroxypropan-2-yl)phenyl)-N-isopropylacetamide;
2-(4-(N,N-Dimethylsulfamoyl)phenyl)-N-ethyl-N-(4-(1,1,1,3,3,3-hexafluoro-2-hydroxypropan-2-yl)phenyl)acetamide;
2-(4-(Ethylsulfonyl)phenyl)-N-isobutyl-N-(4-(perfluoropropan-2-yl)phenyl) acetamide;
2-(4-(Ethylsulfonyl)phenyl)-N-(4-(1,1,1,3,3,3-hexafluoropropan-2-yl)phenyl) acetamide;
Methyl 2-(4-(2-(4-(ethylsulfonyl)phenyl)acetamido)phenyl)-3,3,3-trifluoro-2-hydroxypropanoate;
N-(4-(2-Amino-1,1,1,3,3,3-hexafluoropropan-2-yl)phenyl)-2-(4-(ethylsulfonyl) phenyl)acetamide;
2-(4-(Ethylsulfonyl)phenyl)-N-(4-(1,1,1,3,3,3-hexafluoro-2-(1H-imidazol-1-yl)propan-2-yl)phenyl)acetamide;
2-(4-(Ethylsulfonyl)phenyl)-N-(4-(1,1,1,3,3,3-hexafluoro-2-hydroxypropan-2-yl)cyclohexyl)acetamide;
2-(4-(Ethylsulfonyl)phenyl)-N-(4-(1,1,1,3,3,3-hexafluoro-2-(1H-tetrazol-5-yl)propan-2-yl)phenyl)acetamide;
2-(4-(Ethylsulfonyl)phenyl)-N-(4-(1,1,1,3,3,3-hexafluoro-2-(2-morpholinoethoxy) propan-2-yl)phenyl)acetamide;
2-(1,1-Dioxidothiochroman-6-yl)-N-(4-(1,1,1,3,3,3-hexafluoro-2-hydroxypropan-2-yl)phenyl)acetamide;
N-(4-(1,1,1,3,3,3-Hexafluoro-2-hydroxypropan-2-yl)phenyl)-2-(4-(oxetan-3-ylsulfonyl)phenyl)acetamide;
N-(4-(Ethylsulfonyl)benzyl)-4-(1,1,1,3,3,3-hexafluoro-2-hydroxypropan-2-yl)benzamide;
2-(4-(Ethylsulfonyl)phenyl)-N-(4-(1,1,1,3,3,3-hexafluoro-2-(oxetan-3-yloxy)propan-2-yl) phenyl)acetamide;
2-(4-(Ethylsulfonyl)phenyl)-N-(4-(1,1,1,3,3,3-hexafluoro-2-morpholinopropan-2-yl)phenyl)acetamide;
2-(4-(Ethylsulfonyl)phenyl)-N-(4-(1,1,1,3,3,3-hexafluoro-2-(3-methylpiperidin-1-yl)propan-2-yl)phenyl)acetamide;
2-(4-(Ethylsulfonyl)phenyl)-N-(4-(1,1,1,3,3,3-hexafluoro-2-(4-(4-methoxyphenyl) piperazin-1-yl)propan-2-yl)phenyl)acetamide;
2-(4-(Ethylsulfonyl)phenyl)-N-(4-(1,1,1,3,3,3-hexafluoro-2-(4-(4-fluorophenyl) piperazin-1-yl)propan-2-yl)phenyl)acetamide;
N-(4-(2-Cyano-1,1,1,3,3,3-hexafluoropropan-2-yl)phenyl)-2-(4-(ethylsulfonyl)phenyl) acetamide;
2-(4-(Ethylsulfonyl)phenyl)-N-(4-(1,1,1,3,3,3-hexafluoro-2-methylpropan-2-yl)phenyl)acetamide;
2-(4-(Ethylsulfonyl)phenyl)-N-(4-(2,2,2-trifluoro-1-hydroxy-1-phenylethyl)phenyl) acetamide;
2-(4-(Ethylsulfonyl)phenyl)-N-(4-(2,2,2-trifluoro-1-hydroxy-1-(2-(trifluoromethoxy) phenyl)ethyl)phenyl)acetamide;
2-(4-(Ethylsulfonyl)phenyl)-N-(4-(2,2,2-trifluoro-1-hydroxy-1-(4-methoxyphenyl) ethyl)phenyl)acetamide;
N-(4-(1-Ethoxy-2,2,2-trifluoro-1-phenylethyl)phenyl)-2-(4-(ethylsulfonyl) phenyl)acetamide;
2-(4-(Ethylsulfonyl)phenyl)-N-(4-(2,2,2-trifluoro-1-isobutoxy-1-phenylethyl)phenyl) acetamide;
2-(4-(Ethylsulfonyl)phenyl)-N-(4-(2,2,2-trifluoro-1-methoxy-1-phenylethyl)phenyl) acetamide;
2-(4-(Ethylsulfonyl)phenyl)-N-(4-(1,2,2,2-tetrafluoro-1-phenylethyl) phenyl)acetamide;
N-(4-(1-Cyano-2,2,2-trifluoro-1-phenylethyl)phenyl)-2-(4-(ethylsulfonyl) phenyl)acetamide;
2-(4-(Ethylsulfonyl)phenyl)-N-(4-(2,2,2-trifluoro-1-morpholino-1-phenylethyl) phenyl)acetamide;
2-(4-(Ethylsulfonyl)phenyl)-N-(4-(2,2,2-trifluoro-1-phenyl-1-(pyrrolidin-1-yl)ethyl)phenyl)acetamide;
2-(4-(Oxetan-3-ylsulfonyl)phenyl)-N-(4-(2,2,2-trifluoro-1-hydroxy-1-(2-methoxyphenyl)ethyl)phenyl)acetamide;
2-(4-(Ethylsulfonyl)phenyl)-N-(4-(2,2,2-trifluoro-1-hydroxy-1-(1-methyl-1H-imidazol-4-yl)ethyl)phenyl)acetamide;

or a stereoisomer, a tautomer or a pharmaceutically acceptable salt thereof.

The compounds of the present invention include all isotopic forms, stereoisomeric and tautomeric forms and mixtures thereof in all ratios and their pharmaceutically acceptable salts, pharmaceutically acceptable solvates, prodrugs, N-oxides, S-oxides and polymorphs.

According to another aspect of the present invention, there are provided processes for the preparation of the compound(s) of formula I.

Thus, the compound(s) of formula I can be prepared by various methods including using methods well known to a person skilled in the art. Examples of processes for the preparation of a compound of formula I are described below and illustrated in the following scheme, but are not limited thereto. It will be appreciated by persons skilled in the art that within certain of the processes described herein, the order of the synthetic steps employed can be varied and will depend inter alia on factors such as the nature of functional groups present in a particular substrate and the protecting group strategy (if any) to be adopted. Clearly, such factors will also influence the choice of reagents such as bases, solvents, coupling agents to be used in the reaction steps.

The reagents, reactants and intermediates used in the following processes are either commercially available or can be prepared according to standard procedures known in the art, for instance those reported in the literature references.

In the following schemes and the description of the processes for the synthesis of the compounds of formula I, the starting compounds and the intermediates used for the synthesis of the compounds of the present invention, are designated as compounds B-1, B-2, B-3, B-4 and B-5 for ease of reference. Unless stated otherwise, throughout the description of the process, the corresponding substituent groups in the various formulae representing starting compounds and intermediates have the same meanings as that for the compounds of formula I as indicated in the first aspect and/or one or more embodiments described above.

Scheme 1

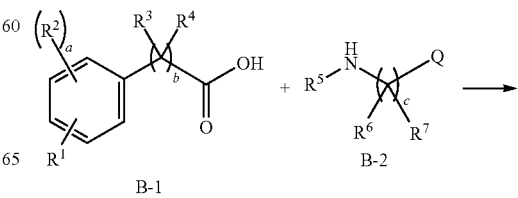

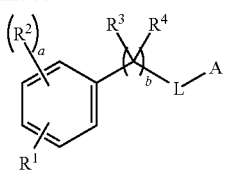

Formula I

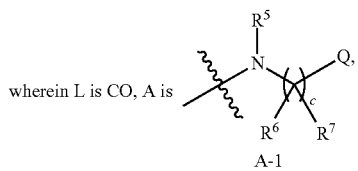

wherein L is CO, A is

A-1

Scheme 1 depicts a general reaction scheme for the preparation of the compound of formula I (wherein, L is —CO—, A is

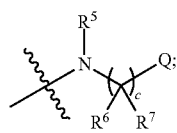

A-1

$R^1$, $R^2$, $R^3$, $R^4$, $R^5$, $R^6$, $R^7$, Q, a, b, c are as defined in the first aspect of the present invention).

In the process as depicted in the above scheme 1, an appropriate amine represented by the compound of formula B-2, is coupled with an appropriately substituted acetic acid represented by the compound of formula B-1, using a suitable coupling reagent, such as 1-ethyl-3-(3-dimethylaminopropyl)carbodiimide (EDC.HCl), 2-(7-aza-1H-benzotriazole-1-yl)-1,1,3,3-tetramethyluronium hexafluorophosphate (HATU), hydroxybenzotriazole (HOBt), oxalyl chloride and the like; in presence of a suitable solvent such as N,N-dimethylformamide (DMF), dichloromethane (DCM), tetrahydrofuran (THF) and the like optionally in the presence of a base such as N,N-diisopropylethylamine (DIEA), triethylamine (TEA) and the like; to obtain the compound of formula I.

Scheme 2

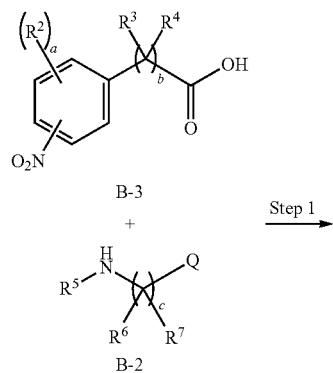

B-3
+

B-2

Step 1

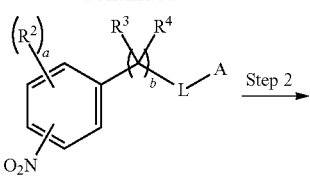 Step 2

B-4 wherein L is CO, A is

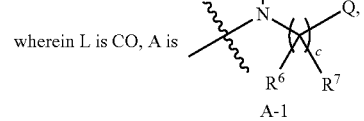

A-1

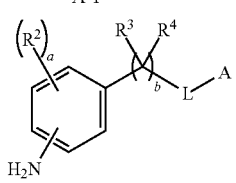

B-5

Step 3

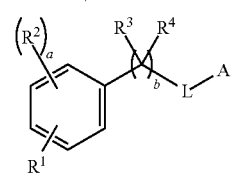

Formula I wherein $R^1$ is $NHSO_2R^\alpha$, L is CO, A is

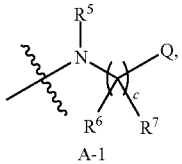

A-1

Scheme 2 depicts a general reaction scheme for the preparation of the compound of formula I (wherein, L is —CO—, A is

A-1

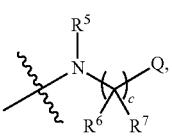

$R^1$ is $NHSO_2R^\alpha$; and $R^2$, $R^3$, $R^4$, $R^5$, $R^6$, $R^7$, $R^\alpha$, Q, a, b and c are as defined in the first aspect of the present invention).

Step-1:

An appropriate amine represented by the compound of formula B-2, is coupled with an appropriately substituted phenylacetic acid represented by the compound of formula B-3 using a suitable coupling reagent, such as EDC.HCl, HATU, HOBt, oxalyl chloride and the like; in the presence of a suitable solvent such as DMF, DCM, THF and the like; optionally in the presence of a base such as DIEA, TEA and the like; to obtain the compound of formula B-4 (wherein, L is CO, A is

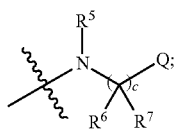

A-1

$R^2$, $R^3$, $R^4$, $R^5$, $R^6$, $R^7$, A, a, b and c are as defined in the first aspect of the present invention).

Step 2:

The compound of formula B-4 obtained in the step 1 is reacted with iron powder and ammonium chloride in the presence of a mixture of solvents such as ethanol:water:THF at a temperature ranging from 60° C. to 80° C. for 5-6 hours to obtain the compound of formula B-5 (wherein, L is CO, A is

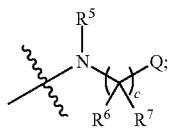

A-1

$R^2$, $R^3$, $R^4$, $R^5$, $R^6$, $R^7$, A, a, b and c are as defined in the first aspect of the present invention).

Step 3:

The compound of formula B-5 obtained in the step 2 is reacted with the reagent A,

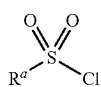

Reagent A in presence of an organic base such as pyridine and a suitable solvent such as DCM and the like; at a temperature ranging from 20° C. to 30° C. for 10-14 hours to obtain the compound of formula I (wherein, L is CO, A is

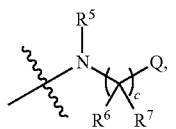

A-1

$R^1$ is $NHSO_2R^a$; $R^2$, $R^3$, $R^4$, $R^5$, $R^6$, $R^7$, $R^a$, Q, a, b, c are as defined in the first aspect of the present invention).

The compounds of formula I can be converted into their pharmaceutically acceptable salts.

The present invention also includes within its scope the pharmaceutically acceptable salts of the compounds of formula I.

The term "pharmaceutically acceptable salts" as used herein refers to organic and inorganic salts of a compound of the present invention (the compounds of formula I), depending on the particular group (acidic or basic group) present in the said compounds. When compounds of the present invention contain relatively acidic groups, base addition salts can be obtained by contacting the compounds of formula I with a sufficient amount of an appropriate base, either neat or in a suitable inert solvent. Examples of pharmaceutically acceptable base addition salts include sodium, potassium, calcium, magnesium, ammonium salts; or an organic base salt. Examples of pharmaceutically acceptable organic base addition salts include those derived from organic bases such as lysine, arginine, guanidine, diethanolamine, choline, tromethamine and the like.

When compounds of the present invention contain relatively basic groups, acid addition salts can be obtained by contacting the compound of formula I with a sufficient amount of an appropriate acid, either neat or in a suitable inert solvent. Examples of pharmaceutically acceptable acid addition salts include those derived from inorganic acids such as hydrochloric, hydrobromic, nitric, carbonic, monohydrogencarbonic, phosphoric, monohydrogenphosphoric, dihydrogenphosphoric, sulfuric, mono-hydrogensulfuric or hydroiodic acids and the like, as well as the salts derived from organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, glucuronic or galacturonic acids and the like. Certain specific compounds of the present invention contain both basic and acidic functionalities that allow the compounds to be converted into either base or acid addition salts.

The compound of formula I can be regenerated from their corresponding salts by contacting the said salt with an appropriate base or acid depending on the type of salt and isolating the parent compound in the conventional manner. The corresponding salts of the compounds differ from their parent compounds with respect to certain physical properties, for example solubility.

The present invention also encompasses within its scope the solvates of the compounds of formula I.

Certain compounds of the present invention can exist in unsolvated forms as well as solvated forms, including hydrated forms. Certain compounds of the present invention can exist in multiple crystalline or amorphous forms. In general, all physical forms are suitable for the uses contemplated by the present invention and are intended to be within the scope of the present invention.

Various polymorphs of the compounds of formula I can be prepared by crystallization of the compounds under different conditions. The different conditions are, for example, using different solvents or their mixtures for crystallization; crystallization at different temperatures; various modes of cooling, ranging from very fast to very slow cooling during crystallizations. Polymorphs can also be obtained by heating or melting the compound followed by gradual or fast cooling. The presence of polymorphs can be determined by infra-red (IR) spectroscopy, solid probe nuclear magnetic resonance (NMR) spectroscopy, differential scanning calorimetry, powder X-ray diffraction or such other techniques.

Those skilled in the art will recognize that stereocenters exist in the compounds of formula I. Accordingly, the present invention includes all possible stereoisomers and geometric isomers of the compound of formula I and includes not only racemic compounds but also the optically active isomers as well. When a compound of formula I is desired as a single enantiomer, it may be obtained either by resolution of the final product or by stereospecific synthesis from either isomerically pure starting material or an appropriate intermediate. Resolution of the final product, an intermediate or a starting material may be effected by any suitable method known in the art, for example, *Chiral reagents for asymmetric synthesis* by Leo A. Paquette; John Wiley & Sons Ltd (2003).

Additionally, in situations wherein tautomers of the compound of formula I are possible, the present invention is intended to include all tautomeric forms of the compounds.

The present invention also encompasses within its scope prodrugs of the compound(s) of formula I. Preferably, prodrugs are those compounds that are converted intracellularly, more preferably, where the cellular converting location is the site of therapeutic action. For instance, preferred produgs are pharmaceutically acceptable ester derivatives convertible by solvolysis under physiological conditions to the parent carboxylic acid. Examples of pharmaceutically acceptable esters include lower alkyl esters, cycloalkyl esters, lower alkenyl esters, benzyl esters, mono- or di-substituted lower alkyl esters such as the pivaloyloxymethyl ester and the like esters which are conventionally known in the art. (An introduction to Medicinal Chemistry, Graham L. Patrick, Second Edition, Oxford University Press, pg 239-248; Prodrugs: Challenges and Rewards, Part 1 and Part 2, AAPS Press, Edited by Valentino J. Stella, Renald T. Borchardt, Michael J. Hagemon, Reza Oliyai, Hans Maag, Jefferson W. Tilley).

In another further aspect, the present invention relates to pharmaceutical compositions that contain a therapeutically effective amount of at least one compound of formula I or its pharmaceutically acceptable salt in addition to a customary pharmaceutically acceptable carrier or excipient. The present invention also relates to a process for the production of the pharmaceutical composition, which includes bringing at least one compound of formula I, into a suitable administration form using a pharmaceutically acceptable excipient or a carrier and, if appropriate, further suitable a pharmaceutically acceptable carriers, additives or auxiliaries. The pharmaceutical compositions containing the compounds of Formula I according to the invention are prepared in a manner known to one skilled in the art.

The pharmaceutical compositions can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermally, in the form of patches, or in other ways, for example in the form of aerosols or nasal sprays.

For the production of oral dosages form of the compounds of Formula I such as the pills, tablets, coated tablets and hard gelatin capsules, it is possible to use, for example, lactose, corn starch or derivatives thereof, gum *arabica*, magnesia or glucose, etc. Pharmaceutically acceptable carriers that can be used for soft gelatin capsules and suppositories are, for example, fats, waxes, natural or hardened oils, etc. Suitable pharmaceutically acceptable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the said solvents.

The pharmaceutical compositions can contain from about 1% to 99%, for example, about 5% to 70%, or from about 10% to about 30% by weight of the compound of formula I or its pharmaceutically acceptable salt. The amount of the compound of formula I or its pharmaceutically acceptable salt in the pharmaceutical compositions normally is from about 5 mg to 500 mg or may be lower than or higher than the lower and the upper limit respectively. The dose of the compound of formula I, which is to be administered, can cover a wide range depending on the type of disease or disorder to be treated. The dose to be administered daily is to be selected to have the desired effect. A suitable dosage can be from about 0.01 mg/kg to 100 mg/kg of the compound of formula I or its pharmaceutically acceptable salt depending on the body weight of the recipient (subject) per day, for example, from about 0.1 mg/kg to 50 mg/kg/day of a compound of formula I or a pharmaceutically acceptable salt of the compound. If required, higher or lower daily doses can also be administered.

The selected dosage level will depend upon a variety of factors including the activity of a compound of the present invention, or its salt employed, the route of administration, the time of administration, the rate of excretion of the particular compound being administered, the duration of the treatment, other concurrently administered drugs, compounds and/or materials, the age, sex, weight, condition, general health and prior medical history of the patient (subject) being treated, and like factors well known in the medical arts.

In addition to the compound of formula I or its pharmaceutically acceptable salt and the pharmaceutically acceptable excipient or carrier substances, the pharmaceutical compositions of the present invention can contain additives such as, for example, fillers, antioxidants, dispersants, emulsifiers, defoamers, flavors, preservatives, solubilizers or colorants. They can also contain more than one compound of formula I or their pharmaceutically acceptable salts. Furthermore, in addition to at least one compound of formula I or its pharmaceutically acceptable salt, the pharmaceutical compositions can also contain one or more other therapeutically or prophylactically active agents.

In one aspect, the present invention relates to a method for the treatment of a disease or a disorder mediated by RORγ, comprising administering to a subject in need thereof; a therapeutically effective amount of a compound of formula I or a stereoisomer, a tautomer or a pharmaceutically acceptable salt thereof.

In another aspect, the present invention provides use of a compound of formula I or a stereoisomer, a tautomer or a pharmaceutically acceptable salt thereof; for the treatment of a disease or a disorder mediated by RORγ.

In yet another aspect, the present invention provides use of a compound of formula I or a stereoisomer, a tautomer or a pharmaceutically acceptable salt thereof; for the manufacture of a medicament for the treatment of a disease or a disorder mediated by RORγ.

In an embodiment, the disease or disorder mediated by RORγ is an autoimmune disease/disorder, an inflammatory disorder or a metabolic diseases/disorder.

In yet another embodiment, the disease or disorder mediated by RORγ is cancer.

In yet another embodiment, the disease or disorder mediated by RORγ is an autoimmune disease or disorder.

In yet another embodiment, the disease or disorder mediated by RORγ is an inflammatory disorder.

In yet another embodiment, the disease or disorder mediated by RORγ is a metabolic disease or disorder.

According to another embodiment, the disease or disorders mediated by RORγ is selected from respiratory diseases such as asthma, chronic obstructive pulmonary disease (COPD) and bronchitis; allergic diseases such as allergic rhinitis and atopic dermatitis; arthritis; multiple sclerosis; psoriasis; cystic fibrosis; lung allograph rejection, Crohn's disease, inflammatory bowel diseases (IBD); irritable bowel syndrome (IBS); colitis and ulcerative colitis.

In an embodiment of the present invention, the disease or disorders mediated by RORγ is an autoimmune diseases/disorder or an inflammatory disease/disorder; which can be selected from the group consisting of: inflammatory bowel disease, rheumatoid arthritis, juvenile rheumatoid arthritis, psoriatic arthritis, osteoarthritis, refractory rheumatoid arthritis, chronic non-rheumatoid arthritis, ankylosing spondylitis, osteoporosis/bone resorption, chronic graft-versus-host disease, acute graft-versus-host disease, multiple sclerosis, systemic lupus erythematosus, Celiac Sprue, idiopathic thrombocytopenic thrombotic purpura, myasthenia gravis, Sjogren's syndrome, scleroderma, asthma, bronchitis, epidermal hyperplasia, Crohn's disease, atherosclerosis, septic shock syndrome, coronary heart disease, vasculitis, ulcerative colitis, psoriasis, adult respiratory distress syndrome, myolitis, polymyolitis, dermatomyolitis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, and delayed type hypersensitivity in skin disorders.

In an embodiment, autoimmune disease that can be treated by the compound of present invention is selected from alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barre syndrome, idiopathic thrombocytopenic purpura, myasthenia gravis, some forms of myocarditis, multiple sclerosis, pemphigus/pemphigoid, pernicious anemia, polyarteritis *nodosa*, polymyositis, primary biliary cirrhosis, psoriasis, rheumatoid arthritis, scleroderma/systemic sclerosis, Sjogren's syndrome, systemic lupus erythematosus, Pernicious anemia (Addison's disease), some forms of thyroiditis (Hashimoto's thyroiditis or chronic lymphocytic thyroiditis), some forms of uveitis, vitiligo and granulomatosis with polyangiitis (Wegener's granulomatosis).

According to another embodiment, the inflammatory disorders are selected from the group consisting of arthritis, asthma, atherosclerosis, celiac disease, chronic prostatitis, colitis, Crohn's disease, dermatitis, diverticulitis, glomerulonephritis, hepatitis, hypersensitivities, inflammatory bowel diseases (IBD), interstitial cystitis, irritable bowel syndrome (IBS), lupus erythematous, nephritis, Parkinson's disease, pelvic inflammatory disease, reperfusion injury, rheumatoid arthritis, sarcoidosis, transplant rejection, ulcerative colitis and vasculitis.

According to another embodiment, the cancers include, but are not limited to, thyroid carcinoma, cardiac sarcoma, lung carcinoma, gastrointestinal carcinoma, genitourinary tract carcinoma, liver carcinoma, mantle cell lymphoma, bone sarcoma, sarcoma of the nervous system, gynaecological carcinoma, haematological cancer, adrenal gland neuroblastoma, skin cancer, astrocytic cancer, breast cancer, colorectal cancer, endometrial cancer, head and neck cancer and oral cancer.

In yet another embodiment, the arthritis that can be treated by the compound of present invention includes rheumatoid arthritis, juvenile rheumatoid arthritis, osteoarthritis, gouty arthritis, pseudogout arthritis, lupus arthritis, septic arthritis and spondyloarthropathies (ankylosing spondylitis, reactive arthritis (Reiter's syndrome), psoriatic arthritis and enteropathic arthritis).

The present invention also encompasses within its scope use of a compound of formula I or a stereoisomer, a tautomer or a pharmaceutically acceptable salt thereof; in combination, with other therapeutically active agents; wherein the compound of formula I and the further therapeutic agent are administered either simultaneously or sequentially.

The therapeutically active agents used in combination with one or more compounds of formula I or its pharmaceutically acceptable salt can be selected from $β_2$-adrenoreceptor agonists (for example, but not limited to, bambuterol, formoterol, levosalbutamol, salmeterol and salbutamol), S1P1 agonist (for example, but not limited to, fingolimod, siponimod (phase III, Novartis) and RPC-1063 (phase III, Receptos)), $H_1$ receptor antagonist, antiinflammatory agents (e.g. corticosteroids (for example, fluticasone) and non-steroidal antiinflammatory agent, NSAID (for example, but not limited to, diclofenac, indomethacin, sulindac, mefenamic acid, piroxicam, ibuprofen, naproxen, ketoprofen, phenylbutazone, aspirin, diflunisal, nimesulide, celecoxib, valdecoxib, etorcoxib and meloxicam)), anticholinergic agents (for example, but not limited to, ipratropium, tiotropium and oxitropium), anti-diabetic agents (for example, but not limited to alogliptin, anagliptin, sitagliptin, saxagliptin, vildagliptin, denagliptin, Dutogliptin, Teneligliptin, Trelagliptin (SYR-472, phase III), gemigliptin (LC15-0444, phase III), omarigliptin (MK-3102, phase III), pioglitazone, rosiglitazone, balaglitazone (DRF-2593, phase III), lobeglitazone (CKD-501, phase III), saroglitazar, farglitazar (GI-262570, Phase III), ragaglitazar (DRF-2725, phase III)), TNF-α inhibitor (for example, but not limited to, etanercept, infliximab, adalimumab, certolizumab and golimumab), COX-1/COX-2 inhibitor (such as celecoxib and rofecoxib), LTD4 receptor antagonist (for example, but not limited to, montelukast, zafirlukast, tipelukast and pranlukast), phosphodiesterase type IV (PDE-IV) inhibitor (for example, but not limited to, rolipram, ibudilast, luteolin, cilomilast and roflumilast), insulin-like growth factor type I (IGF-1) inhibitor, kinase inhibitor (for example, imatinib, gefitinib, erlotinib, sorafenib, dasatinib, sunitinib, nilotinib, lapatinib, pazopanib, vandetanib, vemurafenib and crizotinib) and mTOR inhibitor (such as, rapamycin, sirolimus, temsirolimus, everolimus, deforolimus, cyclosporin and tacrolimus).

It is understood that modifications that do not substantially affect the activity of the various aspects of this invention are included. Accordingly, the following examples are intended to illustrate but not to limit the present invention.

The following abbreviations or terms are used herein:
$CDCl_3$: Deuterated chloroform
DCM: Dichloromethane
DMF: N,N-Dimethylformamide
DMSO: Dimethylsulfoxide
DIEA: N,N-Diisopropylethylamine
HATU: 2-(7-Aza-1H-benzotriazole-1-yl)-1,1,3,3-tetramethyluronium hexafluorophosphate)
HOBt: Hydroxybenzotriazole
EDC.HCl: 1-Ethyl-3-(3-dimethylaminopropyl)carbodiimide
HCl: Hydrochloric acid
LiOH: Lithium hydroxide
$K_2CO_3$ Potassium carbonate
$NaHCO_3$: Sodium bicarbonate
$Na_2SO_4$ Sodium sulphate
NaOH: Sodium hydroxide
$NH_4Cl$: Ammonium chloride
TBAF: Tetra-n-butylammonium fluoride
TEA: Triethylamine THF: Tetrahydrofuran
TLC: Thin Layer Chromatography
g: Gram
kg: Kilogram
mg: Milligram
mL: Millilitre
L: Microlitre
M: Micromolar
mmol: Millimolar
M: Molar
mol: Mole
ng: Nanogram
nM: Nanomolar
° C.: Degree Centigrade
RT: Room temperature (20° C. to 35° C.)

PREPARATION OF INTERMEDIATES

Intermediate 1: 4-(1,1,1,3,3,3-Hexafluoro-2-methoxypropan2-yl)aniline (I-1)

To the stirred solution of 2-(4-aminophenyl)-1,1,1,3,3,3-hexafluoropropan-2-ol (1.0 g, 3.86 mmol) in dry tetrahydrofuran (THF) under inert atmosphere, triphenylphosphine (3.04 g, 11.58 mmol) was added and stirred for 20 minutes. (E)-Diisopropyl diazene-1,2-dicarboxylate (0.936 g, 4.63 mmol) and methanol (0.23 mL, 5.79 mmol) were added to the reaction mixture at 0-5° C. The reaction mixture was refluxed for 4-5 hours. After completion of the reaction, the reaction mixture was diluted with methylene chloride and purified using column chromatography (silica gel, hexane and ethyl acetate).

Intermediate 2: 2-(4-(2-Oxopyrrolidin-1-yl)phenyl)acetic Acid (I-2)

Step 1: Methyl 2-(4-(2-oxopyrrolidin-1-yl)phenyl)acetate

4-Bromobutanoyl chloride (3.37 g, 18.18 mmol) and triethylamine (TEA) (7.55 mL, 54.5 mmol) were stirred in dichloroethane (DCE) (30 mL) and 4-bromobutanoyl chloride (3.37 g, 18.18 mmol) in DCE (5 mL) was added drop wise at 0° C. The reaction mixture was stirred at RT and refluxed for 16 hours. The solvent in the reaction mixture was evaporated and diluted the reaction mixture with dichloromethane (DCM) (30 mL). The organic layer was washed with water (10 mL) and brine (10 mL), dried over sodium sulphate, concentrated and purified by flash column chromatography (silica gel, hexane and ethyl acetate) to obtain the title compound.
Yield: 0.2 g (10%); $^1$H NMR (CDCl$_3$, 300 MHz): δ ppm 1.98-2.02 (m, 2H), 2.53 (t, J=6.0 Hz, 2H), 3.60 (s, 2H), 3.69 (s, 3H), 3.76 (t, J=6.0 Hz, 2H), 7.23 (d, J=9.0 Hz, 2H), 7.94 (d, J=9.0 Hz, 2H); Mass (ESI): m/z 234.1 [M+H]$^+$.

Step 2: 2-(4-(2-Oxopyrrolidin-1-yl)phenyl)acetic Acid

To a stirred solution of methyl 2-(4-(2-oxopyrrolidin-1-yl)phenyl) acetate (200 mg, 0.86 mmol) in THF (5 mL) was added aqueous lithium hydroxide (LiOH) solution (1 M, 5 mL) and the reaction mixture was stirred at RT for 3 hours. The reaction mixture was acidified, extracted with ethyl acetate (15 mL), dried over sodium sulphate to obtain the title compound (150 mg, 78%).

Intermediate 3: 2-(4-Acetamidophenyl)acetic Acid (I-3)

To a stirred solution of 2-(4-aminophenyl) acetic acid (2.0 g, 13.23 mmol) and TEA (3.66 mL, 26.5 mmol) in DCM (20 mL) at RT was added acetic anhydride (1.251 mL, 13.23 mmol) drop wise and stirred for 16 hours at RT. The reaction mixture was acidified, diluted with DCM (30 mL) and the organic layer was washed with water (10 mL) and brine (10 mL), dried over sodium sulphate, concentrated to obtain the title compound (1.2 g, 46%).

Intermediate 4: 2-(4-(N-Methylpivalamido)phenyl)acetic Acid (I-4)

Step 1: Methyl 2-(4-(methylamino)phenyl)acetate

Methyl 2-(4-aminophenyl)acetate (1.0 g, 6.05 mmol) was refluxed in trimethoxymethane (6.42 g, 60.5 mmol) for 6 hours. The solvent was evaporated and re-dissolved in methanol (10 mL) and added sodium borohyride (0.275 g, 7.26 mmol) at 0° C. The reaction mixture was stirred at RT for 3 hours. The solvent in the reaction mixture was distilled off; the residue was acidified with dilute HCl and extracted with ethyl acetate. Reaction mixture was quenched with water (10 mL) and extracted with ethyl acetate (20 mL). The combined organic layer was washed with water (10 mL) and brine (10 mL), dried over sodium sulphate, concentrated and purified by flash column chromatography (silica gel, hexane and ethyl acetate) to obtain the title compound.
Yield: 0.42 g (38%); $^1$H NMR (CDCl$_3$, 300 MHz): δ ppm 2.80 (s, 3H), 3.52 (s, 2H), 3.68 (s, 3H), 6.59 (d, J=9.0 Hz, 2H), 7.11 (d, J=8.4 Hz, 2H); Mass (ESI): m/z 180.1 [M+H]$^+$.

Step 2: Methyl 2-(4-(N-methylpivalamido)phenyl)acetate

To a stirred solution of methyl 2-(4-(methylamino)phenyl)acetate (0.4 g, 2.23 mmol) and TEA (0.45 g, 4.46 mmol) in DCM (8 mL) was added pivaloyl chloride (0.29 g, 2.45 mmol) in DCM (2 mL) drop wise at 0° C. The reaction mixture was stirred for 16 hours at RT. The reaction mixture was concentrated and the residue obtained was dissolved in ethyl acetate (25 mL). The organic solution was washed with water (10 mL) and brine (10 mL), dried over Na$_2$SO$_4$, concentrated and purified by flash column chromatography (silica gel, hexane and ethyl acetate) to obtain the title compound.
Yield: 0.11 g (18.6%). $^1$H NMR (CDCl$_3$, 300 MHz): δ ppm 1.32 (s, 9H), 3.20 (s, 3H), 3.68 (s, 3H), 3.73 (s, 2H), 7.18 (d, J=8.1 Hz, 2H), 7.30 (d, J=9.0 Hz, 2H); Mass (ESI): m/z 264.1 [M+H]$^+$.

Step 3: 2-(4-(N-Methylpivalamido)phenyl)acetic Acid

To a stirred solution of methyl 2-(4-(N-methylpivalamido)phenyl)acetate (0.10 g, 0.38 mmol) in THF (4 mL) was added LiOH (0.01 g, 0.46 mmol) in water (1 mL) and stirred the reaction mixture at RT for 12 hours. The reaction mixture was acidified with dilute HCl and extracted with ethyl acetate (10 mL). The organic layer was washed with brine (5 mL), dried over sodium sulphate and concentrated to obtain the title compound. Yield: 0.060 g (51%).

Intermediate 5: 4-(Cyclohexyloxy)-3-(trifluoromethyl)aniline (I-5)

Step 1: 1-(Cyclohexyloxy)-4-nitro-2-(trifluoromethyl)benzene

Cyclohexanol (0.371 g, 3.70 mmol) and cesium carbonate (1.81 g, 5.55 mmol) were stirred in dry N,N-dimethylformamide (DMF) (4 mL) under nitrogen atmosphere. To this added 1-bromo-4-nitro-2-(trifluoromethyl)benzene (0.5 g, 1.852 mmol) and the reaction mixture was heated to 60° C. for 16 hours. The reaction mixture was quenched with water (5 mL) and extracted with ethyl acetate (20 mL). The organic layer was washed with water (2×10 mL) and brine (10 mL), dried over sodium sulphate and concentrated to obtain the title compound.
Yield: 200 mg (20.0%).

Step 2: 4-(Cyclohexyloxy)-3-(trifluoromethyl)aniline

To a solution of 1-(cyclohexyloxy)-4-nitro-2-(trifluoromethyl)benzene (0.100 g, 0.35 mmol) in ethanol:water (2:1, 3 mL) was added ammonium chloride (0.01 g, 0.25 mmol) and iron powder (0.060 g, 1.05 mmol) and the reaction mixture was heated to 80° C. for 30 minutes. The reaction mixture was cooled to RT and filtered through celite. The filtrate was concentrated and dissolved in ethyl acetate (15 mL). The organic layer was washed with brine (10 mL), dried over sodium sulphate and concentrated to obtain the title compound.
Yield: 0.045 g (50%).

Intermediate 6: 2-(4-(Aminomethyl)phenyl)-1,1,1,3,3,3-hexafluoropropan-2-ol (I-6)

Step 1: 1,1,1,3,3,3-Hexafluoro-2-(4-iodophenyl)propan-2-ol

To the stirred solution of 2-(4-aminophenyl)-1,1,1,3,3,3-hexafluoropropan-2-ol (2.0 g, 7.72 mmol) in water (5 mL) was added HCl (3.86 mL, 23.15 mmol) at 0° C. To this, sodium nitrite (0.639 g, 9.26 mmol) in water was added drop wise at 0° C. and stirred for 1 hour. Potassium iodide (1.922 g, 11.58 mmol) was added and the reaction mixture was stirred at ambient temperature. After completion of the reaction, the aqueous layer was extracted with DCM. The DCM layer was dried over sodium sulphate and evaporated. The crude material obtained was purified by flash column chromatography (silica gel, hexane and ethyl acetate).
$^1$H NMR (DMSO-d$_6$, 300 MHz): δ ppm 8.87 (s, 1H), 7.92 (d, J=8.7 Hz, 2H), 7.46 (d, J=8.1 Hz, 2H).

Step 2: 4-(1,1,1,3,3,3-Hexafluoro-2-hydroxypropan-2-yl)benzonitrile

To a solution of 1,1,1,3,3,3-hexafluoro-2-(4-iodophenyl)propan-2-ol (1.5 g, 4.05 mmol), zinc cyanide (1.190 g, 10.13 mmol) in DMF (5 mL) purged with argon was added palladium tetrakis phosphine (0.117 g, 0.405 mmol) and heated to 80° C. for 16 hours. After completion of the reaction, the reaction mixture was quenched with water and extracted with ethyl acetate. The organic layer was dried over sodium sulphate and evaporated the solvent to obtain the crude material. The crude material obtained was purified by column chromatography (silica gel, hexane and ethyl acetate) to obtain the pure title compound.
$^1$H NMR (DMSO-d$_6$, 300 MHz): δ ppm 9.17 (s, 1H), 8.03 (d, J=8.4 Hz, 2H), 7.88 (d, J=8.1 Hz, 2H); Mass (ESI): m/z 270 [M+H]$^+$.

Step 3: 2-(4-(Aminomethyl)phenyl)-1,1,1,3,3,3-hexafluoropropan-2-ol

To a solution of 4-(1,1,1,3,3,3-hexafluoro-2-hydroxypropan-2-yl)benzonitrile (305 mg, 1.133 mmol) in THF (10 mL) under argon atmosphere was added lithium aluminium hydride (LAH) (1.7 mL, 1.700 mmol) at 0° C. and the reaction mixture was stirred for 16 hours. After completion of the reaction, the reaction mixture was quenched with ammonium chloride and extracted with ethyl acetate. The organic layer was dried over sodium sulphate and evaporated to obtain the crude material. The crude material obtained was purified by column chromatography (silica gel, hexane and ethyl acetate).
$^1$H NMR (DMSO-d$_6$, 300 MHz): δ ppm 8.64 (s, 1H), 7.6 (d, J=7.8 Hz, 2H), 7.46 (d, J=8.1 Hz, 2H), 3.73 (s, 2H); Mass (ESI): m/z 257 [M$^+$-NH$_2$].

Intermediate 7: 6-Aminothiochroman-4-one 1,1-dioxide (I-7)

Step 1: 3-((4-Nitrophenyl)thio)propanoic Acid

To a stirred solution of 4-nitrobenzenethiol (15 g, 97 mmol) in 10% aqueous KOH (50 mL), was suspended in 3-bromopropanoic acid (16.27 g, 106 mmol) and the solution was refluxed for 5 hours. After cooling, the reaction mixture was extracted with ethyl acetate and the aqueous layer was separated and adjusted pH to 1 using HCl (6N). The precipitate obtained was filtered, washed with water and dried.
$^1$H NMR (DMSO-d$_6$, 300 MHz): δ ppm 12.47 (s, 1H), 8.14 (d, J=9 Hz, 2H), 7.52 (d, J=9 Hz, 2H), 3.33 (t, J=6.9 Hz, 2H), 2.64 (t, J=6.9 Hz, 2H).

Step 2: 6-Nitrothiochroman-4-one

The solution of 3-((4-nitrophenyl)thio)propanoic acid (1.5 g, 6.60 mmol) in thionyl chloride (14.45 mL, 198 mmol) was refluxed for 4 hours. Excess thionyl chloride was removed and the residue was dissolved in anhydrous DCM (15 mL). To this aluminium chloride (1.320 g, 9.90 mmol) was added and the reaction mixture was stirred at RT for 4 hours. After completion of the reaction, the reaction mixture was quenched carefully with water and the organic layer was collected. To the aqueous layer was added DCM and separated out the organic layer. The combined organic layer was dried over sodium sulphate and evaporated. The residue obtained was dissolved in ethyl acetate and precipitated with hexane. The precipitate obtained was filtered to obtain 6-nitrothiochroman-4-one.
$^1$H NMR (DMSO-d$_6$, 300 MHz): δ ppm 8.61 (d, J=2.1 Hz, 1H), 8.24 (d, J=9 Hz, 1H), 7.67 (d, J=9 Hz, 1H), 3.47 (t, J=5.7 Hz, 2H), 3.00 (t, J=6.6 Hz, 2H); Mass (ESI): m/z 210 [M+H]$^+$.

Step 3: 6-Nitrothiochroman-4-one 1,1-dioxide

To the stirred solution of 6-nitrothiochroman-4-one (1 g, 4.78 mmol) in DCM (15 mL) was added m-chloroperbenzoic acid (m-CPBA) (7.50 g, 23.90 mmol) at 0° C. and the reaction mixture was stirred for 2 hours. After completion of the reaction, the reaction mixture was quenched with water and neutralized with NaOH (10%) solution. The organic layer was collected and the aqueous layer was extracted with ethyl acetate. The combined organic layer was dried over sodium sulphate and evaporated to dryness. The residue obtained was purified by column chromatography (silica gel, hexane and ethyl acetate).

$^1$H NMR (DMSO-$d_6$, 300 MHz): δ ppm 8.67 (d, J=8.7 Hz, 1H), 8.57 (s, 1H), 8.25 (d, J=8.4 Hz, 1H), 4.17 (t, J=6.3 Hz, 2H), 3.36-3.33 (m, 2H); Mass (ESI): m/z 265[M+Na]$^+$.

Step 4: 6-Aminothiochroman-4-one 1,1-dioxide

To the compound of 6-nitrothiochroman-4-one 1,1-dioxide (250 mg, 1.036 mmol) was added iron powder (405 mg, 7.25 mmol), ammonium chloride (166 mg, 3.11 mmol), ethanol (15 mL), water (5 mL) and the resulting mixture was heated at 80° C. for 2 hours. After completion of the reaction, the reaction mixture was filtered through celite bed and the residue was washed with ethanol. The filtrate was evaporated to remove the solvent and added water. The aqueous layer was extracted with ethyl acetate. The organic layer was dried over sodium sulphate and the solvent was evaporated to obtain crude material. The crude material obtained was purified by column chromatography (silica gel, hexane and ethyl acetate).

$^1$H NMR (DMSO-$d_6$, 300 MHz): δ ppm 7.56 (d, J=8.4 Hz, 1H), 7.08 (d, J=1.8 Hz, 1H), 6.92 (d, J=8.4 Hz, 1H), 6.30 (s, 2H), 3.81 (t, J=6.0 Hz, 2H), 3.15 (t, J=6 Hz, 2H); Mass (ESI): m/z 212 [M+H]$^+$.

Intermediate 8: 6-Aminothiochroman-4-one (I-8)

To the compound of 6-nitrothiochroman-4-one (1.5 g, 7.17 mmol) was added iron powder (4 g, 71.7 mmol), ammonium chloride (1.534 g, 28.7 mmol), ethanol (15 mL), water (5.00 mL) and the reaction mixture was heated at 80° C. for 2 hours. After completion of the reaction, the reaction mixture was filtered through celite and the residue was washed with ethanol. The filtrate was evaporated, added water and extracted with ethyl acetate. The organic layer was dried over sodium sulphate and evaporated to obtain the crude material. The crude material obtained was purified by column chromatography (silica gel, hexane and ethyl acetate).

$^1$H NMR (DMSO-d6, 300 MHz): δ ppm 7.21 (d, J=2.4 Hz, 1H), 7.01 (d, J=8.4 Hz, 1H), 6.92 (dd, J=8.4 Hz, 2.4 Hz, 1H), 5.24 (s, 2H), 3.19 (t, J=5.7 Hz, 2H), 2.81 (t, J=6.6 Hz, 2H); Mass (ESI): m/z 180 [M+H]$^+$.

Intermediate 9:
2-(4-(Morpholinosulfonyl)phenyl)acetic Acid (I-9)

Step 1: Ethyl 2-(4-(chlorosulfonyl)phenyl)acetate

To the compound of ethyl 2-phenylacetate (8.0 g, 48.7 mmol), chlorosulphonic acid (16.31 mL, 244 mmol) was added drop wise at 40° C. and the reaction mixture was stirred at RT for 30 minutes. The reaction mixture was poured into ice and extracted with DCM. The organic layer was washed with brine, dried over sodium sulphate and evaporated to obtain the crude product. The crude product obtained was purified by column chromatography (silica gel, hexane and ethyl acetate).

Step 2: Ethyl
2-(4-(morpholinosulfonyl)phenyl)acetate

To a solution of ethyl 2-(4-(chlorosulfonyl)phenyl)acetate (690 mg, 2.63 mmol) in tetrahydrofuran (5 mL) was added TEA (732 µL, 5.25 mmol) and morpholine (252 mg, 2.89 mmol) at 0° C. and the reaction mixture was stirred for 30 minutes. After completion of the reaction, the reaction mixture was quenched with water and extracted with ethyl acetate. The organic layer was dried over sodium sulphate and evaporated to obtain crude product. The crude material was purified by column chromatography (silica gel, hexane and ethyl acetate).

$^1$H NMR (DMSO-$d_6$, 300 MHz): δ ppm 7.69 (d, J=7.8 Hz, 2H), 7.56 (d, J=7.8 Hz, 2H), 4.12 (q, J=7.2 Hz, 2H), 3.85 (d, J=6.3 Hz, 2H), 3.60 (bs, 4H), 2.92 (bs, 4H), 1.20 (t, J=6.9 Hz, 3H); Mass (ESI): m/z 314 [M+H]$^+$.

Step 3: 2-(4-(Morpholinosulfonyl)phenyl)acetic Acid

To a solution of ethyl 2-(4-(morpholinosulfonyl)phenyl) acetate (700 mg, 2.234 mmol) in methanol (5 mL) was added sodium hydroxide (22.34 mg, 22.34 mmol) and the reaction mixture was stirred at RT for 1.5 hours. After completion of the reaction, the reaction mixture is evaporated to remove methanol, diluted with water and extracted with ethyl acetate. The aqueous layer was acidified with 1N HCl and extracted with DCM. The combined organic layer was washed with brine, dried over sodium sulphate and evaporated to obtain crude material. The material obtained was crystallized by DCM/hexane.

$^1$H NMR (DMSO-$d_6$, 300 MHz): δ ppm 12.52 (s, 1H), 7.68 (d, J=7.8 Hz, 2H), 7.55 (d, J=7.8 Hz, 2H), 3.97 (s, 2H), 3.60 (bs, 4H), 2.92 (bs, 4H); Mass (ESI): m/z 308 [M+Na]$^+$.

Intermediate 10: 2-(2-Amino-5-cyclohexylphenyl)-1,1,1,3,3,3-hexafluoropropan-2-ol (I-10)

In a sealed tube added 4-cyclohexylaniline (0.25 g, 1.426 mmol), hexafluoroacetone trihydrate (0.359 mL, 2.85 mmol) and heated at 110° C. for 16 hours. After completion of the reaction, the reaction mixture was quenched with water and extracted with ethyl acetate. The organic layer was dried over sodium sulphate and evaporated to obtain the title compound.

Intermediate 11: 1-(4-Aminophenyl) cyclopropanecarbonitrile (I-11)

Step 1: 1-(4-Nitrophenyl)cyclopropanecarbonitrile

To a solution of 2-(4-nitrophenyl)acetonitrile (1.0 g, 6.17 mmol), 1,2-dibromoethane (2.55 g, 13.57 mmol), tetrabutylammonium (1.988 g, 6.17 mmol) in acetonitrile (10 mL), 50% sodium hydroxide solution (2 mL) was slowly added under nitrogen atmosphere at room temperature. The reaction mixture was stirred at 40° C. for one hour. After completion of the reaction, the reaction mixture was added with DCM and water. The aqueous layer was extracted with DCM. The combined organic layer was dried over sodium sulphate and evaporated. The crude material was purified by column chromatography (silica gel, hexane and ethyl acetate).

$^1$H NMR (DMSO-$d_6$, 300 MHz): δ ppm 8.24 (d, J=9 Hz, 2H), 7.59 (d, J=8.7 Hz, 2H), 1.95-1.91 (m, 2H), 1.71-1.66 (m, 2H).

Step 2: 1-(4-Aminophenyl) cyclopropanecarbonitrile

To a solution of 1-(4-nitrophenyl)cyclopropanecarbonitrile (500 mg, 2.66 mmol) in ethanol (15 mL) and water (5 mL) was added iron (1484 mg, 26.6 mmol), ammonium chloride (1421 mg, 26.6 mmol) and the reaction mixture was heated at 80° C. for 2 hours. After completion of the reaction, the reaction mixture was filtered through celite bed and the residue was washed with ethanol. The filtrate was evaporated to remove the solvent, added water and extracted with ethyl acetate. The organic layer was dried over sodium sulphate and evaporated to obtain crude material. The crude material was purified by column chromatography (silica gel, hexane and ethyl acetate).

$^1$H NMR (DMSO-$d_6$, 300 MHz): δ ppm 6.99 (d, J=8.1 Hz, 2H), 6.53 (d, J=7.8 Hz, 2H), 5.17 (s, 2H), 1.54 (s, 2H), 1.23 (s, 2H); Mass (ESI): m/z 159 [M+H]$^+$.

Intermediate 12:4'-Amino-2'-(trifluoromethyl)-5,6-dihydro-[1,1'-biphenyl]-4(3H)-one (I-12)

Step 1: 4,4,5,5-Tetramethyl-2-(4-nitro-2-(trifluoromethyl)phenyl)-1,3,2-dioxaborolane To a solution of 1-bromo-4-nitro-2-(trifluoromethyl)benzene (5.0 g, 18.52 mmol) and 4,4,4',4',5,5,5',5'-octamethyl-2,2'-bi(1,3,2-dioxaborolane) (4.70 g, 18.52 mmol) in dioxane (50 mL), nitrogen was purged for 15 minutes and added potassium acetate (2.73 g, 27.8 mmol), [1,1-bis(diphenylphosphino)ferrocene]dichloro palladium (I) complex with DCM (0.756 g, 0.926 mmol). The reaction mixture was refluxed for 16 hours and cooled the reaction mixture to RT. The reaction mixture was filtered through celite, filtrate was concentrated and purified by column chromatography (silica gel, hexane and ethyl acetate) to obtain the title compound.

Yield: 3.2 g (54%); $^1$H NMR (CDCl$_3$, 300 MHz): δ ppm 1.27 (s, 12H), 7.97 (d, J=9.0 Hz, 1H), 8.28 (dd, J$_1$ & J$_2$=3.0 Hz, 1H), 8.58 (d, J=3.0 Hz, 1H); Mass (ESI): m/z 316.1 [M−H]$^+$.

Step 2: 8-(4-Nitro-2-(trifluoromethyl)phenyl)-1,4-dioxaspiro[4.5]dec-7-ene

To a stirred solution of 4,4,5,5-tetramethyl-2-(4-nitro-2-(trifluoromethyl)phenyl)-1,3,2-dioxaborolane (2.200 g, 6.94 mmol), 1,4-dioxaspiro[4.5]dec-7-en-8-yl trifluoromethanesulfonate (2.000 g, 6.94 mmol), potassium phosphate (2.209 g, 10.41 mmol) in THF (15 mL), nitrogen gas was purged for 15 minutes and added tetrakis(triphenylphosphine)palladium(0) (0.059 g, 0.347 mmol). The reaction mixture was refluxed for 16 hours and cooled to RT. The reaction mixture was filtered through celite, filtrate was concentrated and purified by column chromatography (silica gel, hexane and ethyl acetate) to obtain the title compound.

Yield: 1.30 g (59%); $^1$H NMR (CDCl$_3$, 300 MHz): δ ppm 1.90 (t, J=6.0 Hz, 2H), 2.45-2.48 (m, 4H), 4.03 (s, 4H), 5.56 (br s, 1H), 7.48 (d, J=9.0 Hz, 1H), 8.32 (dd, J$_1$ & J$_2$=3.0 Hz, 1H), 8.52 (d, J=3.0 Hz, 1H); Mass (ESI): m/z 327.1 [M−H]$^+$.

Step 3: 4'-Nitro-2'-(trifluoromethyl)-5,6-dihydro-[1,1'-biphenyl]-4(3H)-one

To a stirred solution of 8-(4-nitro-2-(trifluoromethyl)phenyl)-1,4-dioxaspiro[4.5]dec-7-ene (1.0 g, 3.04 mmol) in DCM (10 mL), TFA (10 mL) was added drop wise at 0° C. and the reaction mixture was stirred at RT for 16 hours. The solvent in the reaction mixture was distilled out and added ethyl acetate (20 mL). The solution was washed with saturated NaHCO$_3$ solution (10 mL) and brine (10 mL), dried over sodium sulphate and concentrated to obtain the title compound.

Yield: 0.55 g (63%).

Step 4: 4'-Amino-2'-(trifluoromethyl)-5,6-dihydro-[1,1'-biphenyl]-4(3H)-one

To a stirred solution of 4'-nitro2'-(trifluoromethyl)-5,6-dihydro-[1,1'-biphenyl]-4(3H)-one (300 mg, 1.052 mmol) in ethnol:water (3 mL, 2:1) was added ammonium chloride (39.8 mg, 0.736 mmol), iron (58.7 mg, 1.052 mmol) and the reaction mixture was stirred at 80° C. for 30 minutes. The reaction mixture was filtered, the filtrate was concentrated and extracted with ethyl acetate (10 mL). The organic layer was washed with brine (10 mL), dried over sodium sulphate and concentrated to obtain the title compound.

Yield: 140 mg (52%); $^1$H NMR (CDCl$_3$, 300 MHz): δ ppm 2.65-2.75 (m, 4H), 3.08 (br s, 2H), 5.79 (br s, 1H), 7.48 (d, J=9.0 Hz, 1H), 8.38 (dd, J$_1$ & J$_2$=3.0 Hz, 1H), 8.57 (d, J=3.0 Hz, 1H); Mass (ESI): m/z 258.1 [M+3H]$^+$.

Intermediate 13: 5-Cyclohexylidene-5,6,7,8-tetrahydronaphthalen-2-amine (I-13)

To a mixture of THF (30 mL) and Zinc powder (3.24 g, 49.6 mmol) under inert atmosphere was added TiCl$_4$ (3.28 mL, 29.8 mmol) slowly at 0° C. and the reaction mixture was refluxed for one hour. The reaction mixture was cooled to room temperature, 6-amino-3,4-dihydronaphthalen-1(2H)-one (1.6 g, 9.93 mmol), cyclohexanone (1.029 mL, 9.93 mmol) in THF (5 mL) were added and stirred at room temperature. Saturated solution of sodium carbonate was added to the reaction mixture and stirred for 30 minutes. The reaction mixture was extracted with DCM, dried over sodium sulphate and concentrated to obtain the crude product. The crude product obtained was further purified by column chromatography (silica gel, hexane and ethyl acetate).

$^1$H NMR (DMSO-$d_6$, 300 MHz): δ ppm 1.65-1.59 (m, 8H), 2.41-2.22 (m, 8H), 4.93 (s, 2H), 6.34-6.32 (m, 2H), 6.82-6.80 (s, 1H); Mass (ESI): m/z 228 [M+H]$^+$.

Intermediate 14: 6-Aminochroman-4-one (I-14)

Step 1: 6-Nitrochroman-4-one

To a solution of chroman-4-one (5.0 g, 33.7 mmol) in concentrated H$_2$SO$_4$ (50 mL), a solution of potassium nitrate (3.75 g, 37.1 mmol) in 30 mL concentrated H$_2$SO$_4$ was added portion-wise at 0° C. The solution was stirred for 3 hours at 0° C. After completion of the reaction, the solution was poured slowly onto a water-ice mixture. The precipitate obtained was filtered, washed with water and air-dried, to obtain a crude mixture which contains 6-nitro-4-chromanone as the major isomer and 5-nitro-4-chromanone as a minor isomer. The crude mixture was recrystallized using ethyl acetate/hexane to obtain the pure compound.

$^1$H NMR (DMSO-$d_6$, 300 MHz): δ ppm 8.80 (d, J=2.7 Hz, 1H), 8.36 (dd, J=2.7 & 9.3 Hz, 1H), 7.14 (d, J=9.3 Hz, 1H), 4.70 (t, J=6.6 & 6.6 Hz, 2H), 2.94 (t, J=6.6 & 6.6 Hz, 2H); Mass (ESI): m/z 194 [M+H]$^+$.

Step 2: 6-Aminochroman-4-one

To a solution of 6-nitrochroman-4-one (4.0 g, 20.71 mmol) in ethanol was added 10% Pd/C (~400 mg) and stirred at room temperature under 45 psi pressure for 4 hours using Parr shaker. After completion of the reaction, the reaction mixture was filtered through celite, concentrated and purified by flash column chromatography to obtain the title compound.

$^1$H NMR (DMSO-d$_6$, 300 MHz): δ ppm 6.92 (d, J=2.7 Hz, 1H), 6.84 (dd, J=2.7 & 6.0 Hz, 1H), 6.75 (dd, J=2.4 & 6.3 Hz, 1H), 4.93 (bs, 2H), 4.38 (t, J=2.4 &4.2 Hz, 2H), 2.68 (t, J=2.4 & 4.2 Hz, 2H); Mass (ESI): m/z 164 [M+H]$^+$.

Intermediate 15: 7-Amino-4-ethyl-2H-benzo[b][1,4]oxazin-3(4H)-one (I-15)

Step 1: 7-Nitro-2H-benzo[b][1,4]oxazin-3(4H)-one

Methyl 2-bromoacetate (11.91 g, 78 mmol), 2-amino-5-nitrophenol (10 g, 64.9 mmol) and potassium carbonate (22.42 g, 162 mmol) in DMF (30 mL) was stirred at 90° C. for 24 hours. The reaction mixture was allowed to cool and diluted with water. The precipitate obtained was filtered and dried to obtain the title compound.

$^1$H NMR (DMSO-d$_6$, 300 MHz): δ ppm 11.35 (bs, 1H), 7.91 (dd, J=2.4 & 8.7 Hz, 1H), 7.75 (d, J=2.4 Hz, 1H), 7.06 (d, J=8.7 Hz, 1H), 4.71 (s, 2H); Mass (ESI): m/z 195 [M+H]$^+$.

Step 2: 4-Ethyl-7-nitro-2H-benzo[b][1,4]oxazin-3(4H)-one

To a stirred suspension of cesium carbonate (2.52 g, 7.73 mmol) and 7-nitro-2H-benzo[b][1,4]oxazin-3(4H)-one (1 g, 5.15 mmol) in DMF (5 mL), ethyl iodide (0.499 mL, 6.18 mmol) was added and the reaction mixture was stirred at room temperature for 7 hours. The reaction mixture was concentrated and the residue was stirred with water. The precipitate obtained was filtered and dried to obtain the title compound.

$^1$H NMR (DMSO-d$_6$, 300 MHz): δ ppm 7.99 (dd, J=2.4 & 9.0 Hz, 1H), 7.87 (d, J=2.4 Hz, 1H), 7.11 (d, J=9.0 Hz, 1H), 4.70 (s, 2H), 4.09 (q, J=7.2 & 6.9 Hz, 2H), 1.34 (t, J=7.2 & 7.2 Hz, 3H); Mass (ESI): m/z 223 [M+H]$^+$.

Step 3: 7-Amino-4-ethyl-2H-benzo[b][1,4]oxazin-3(4H)-one

This compound was prepared analogous to the process described in the step 2 of the intermediate 14. $^1$H NMR (DMSO-d$_6$, 300 MHz): δ ppm 6.87 (d, J=8.4 Hz, 1H), 6.27 (s, 1H), 6.24 (d, J=5.7 Hz, 1H), 5.01 (s, 2H), 4.46 (s, 2H), 3.85 (q, J=6.9 & 6.9 Hz, 2H), 1.11 (t, J=6.9 & 6.9 Hz, 3H); Mass (ESI): m/z 193 [M+H]$^+$.

Preparation of the Representative Compounds of Formula I

Example 1

2-(4-(Ethylsulfonyl)phenyl)-N-(4-(1,1,1,3,3,3-hexafluoro-2-methoxypropan-2-yl)phenyl) acetamide To the stirred solution of 2-(4-(ethylsulfonyl)phenyl)acetic acid (0.079 g, 0.348 mmol) in dry DMF was added HATU (0.265 g, 0.696 mmol) under inert atmosphere and stirred for 20 minutes. To the reaction mixture were added 4-(1,1,1,3,3,3-Hexafluoro-2-methoxypropan2-yl)aniline (Intermediate I-1, 0.348 mmol) and diisopropylethylamine (0.090 g, 0.696 mmol). After completion of the reaction, the reaction mixture was quenched with water and extracted with dichloromethane. The organic layer was washed with brine and dried over anhydrous Na$_2$SO$_4$. The crude product was purified by column chromatography (silica gel, hexane and ethyl acetate) to obtain the title compound.

$^1$H NMR (DMSO-d$_6$, 300 MHz): δ ppm 10.56 (s, 1H), 7.85 (d, J=8.1 Hz, 4H), 7.61 (d, J=8.1 Hz, 2H), 7.50 (d, J=8.4 Hz, 2H), 3.82 (s, 2H), 3.40 (s, 3H), 3.27 (q, J=7.5 Hz, 2H), 1.10 (t, J=7.5 Hz, 3H); Mass (ESI): m/z 484.7 [M+H]$^+$.

Example 2

N-(1,1-Dioxido-4-oxothiochroman-6-yl)-2-(4-(ethylsulfonyl)phenyl)acetamide

This compound was prepared by the reaction of 2-(4-(ethylsulfonyl)phenyl)acetic acid (70.2 mg, 0.308 mmol) and 6-aminothiochroman-4-one 1,1-dioxide (Intermediate I-7, 65 mg, 0.308 mmol) using HATU (234 mg, 0.615 mmol) and DIEA (0.161 mL, 0.923 mmol) in DMF (3 mL) as per the process described in the preparation of the compound of example 1.

$^1$H NMR (DMSO-d$_6$, 300 MHz): δ ppm 10.87 (s, 1H), 8.27 (s, 1H), 8.11 (d, J=5.1 Hz, 1H), 7.94 (d, J=5.1 Hz, 1H), 7.86 (d, J=4.8 Hz, 2H), 7.62 (d, J=5.1 Hz, 2H), 3.96 (t, J=3.6 Hz, 2H), 3.88 (s, 2H), 3.3-3.23 (m, 4H), 1.11 (t, J=4.2 Hz, 3H); Mass (ESI): m/z 422 [M+H]$^+$.

Example 3

2-(4-(Ethylsulfonyl)phenyl)-N-(4-oxothiochroman-6-yl)acetamide

This compound was prepared by the reaction of 2-(4-(ethylsulfonyl)phenyl)acetic acid (191 mg, 0.837 mmol) with 6-aminothiochroman-4-one (Intermediate I-8, 150 mg, 0.837 mmol) using HATU (636 mg, 1.674 mmol), DIEA (0.438 mL, 2.51 mmol) in dry THF as per the process described for the preparation of the compound of example 1.

$^1$H NMR (DMSO-d$_6$, 300 MHz): δ ppm 10.41 (s, 1H), 7.85 (d, J=8.1 Hz, 2H), 7.74 (dd, J=8.7 Hz, 2.4 Hz, 1H), 7.60 (d, J=8.4 Hz, 2H), 7.32 (d, J=8.4 Hz, 2H), 3.82 (s, 2H), 3.30-3.23 (m, 4H), 2.89-2.72 (m, 2H), 1.1 (t, J=7.2 Hz, 3H); Mass (ESI): m/z 390 [M+H]$^+$.

Example 4

N-(4-Cyclohexyl-2-(1,1,1,3,3,3-hexafluoro-2-hydroxypropan-2-yl)phenyl)-2-(4-(ethyl sulfonyl)phenyl)acetamide This compound was prepared by the reaction of 2-(4-(ethylsulfonyl)phenyl)acetic acid (167 mg, 0.733 mmol) with 2-(2-amino-5-cyclohexylphenyl)-1,1,1,3,3,3-hexafluoropropan-2-ol (Intermediate I-10, 0.249 g, 0.733 mmol) using HATU (557 mg, 1.465 mmol), DIEA (0.384 mL, 2.198 mmol) in DMF (6 mL) as per the process described for the preparation of the compound of example 1.

$^1$H NMR (DMSO-d$_6$, 500 MHz): δ ppm 9.67 (s, 1H), 8.00 (s, 1H), 7.86 (d, J=8 Hz, 2H), 7.6 (d, J=6.7 Hz, 2H), 7.36 (d, J=8.0 Hz, 1H), 7.26 (s, 1H), 3.83 (s, 2H), 3.29 (q, J=7.0 Hz, 2H), 1.76-1.67 (m, 5H), 1.34-1.30 (m, 7H), 1.11 (t, J=7 Hz, 3H); Mass (ESI): m/z 552 [M+H]$^+$.

Example 5

N-(4-(1-Cyanocyclopropyl)phenyl)-2-(4-(ethylsulfonyl)phenyl)acetamide

This compound was prepared by the reaction of 2-(4-(ethylsulfonyl)phenyl)acetic acid (100 mg, 0.438 mmol)

with 1-(4-aminophenyl)cyclopropanecarbonitrile (Intermediate I-11, 62.4 mg, 0.394 mmol) using the HATU (333 mg, 0.876 mmol), DIEA (230 μL, 1.314 mmol) in DMF (6 mL) as per the process described in the preparation of the compound of example 1.

$^1$H NMR (DMSO-d$_6$, 300 MHz): δ ppm 10.34 (s, 1H), 7.84 (d, J=8.1 Hz, 2H), 7.60 (d, J=7.8 Hz, 4H), 7.27 (d, J=8.4 Hz, 2H), 3.78 (s, 2H), 3.33 (q, J=7.5 Hz, 2H), 1.68 (bs, 2H), 1.43 (bs, 2H), 1.10 (t, J=7.2 Hz, 3H); Mass (ESI): m/z 369 [M+H]$^+$.

Example 6

2-(4-(Ethylsulfonyl)phenyl)-N-(4-(1,1,1,3,3,3-hexafluoro-2-(4-phenylbutoxy)propan-2-yl) phenyl) acetamide This compound was prepared by the reaction of 2-(4-(ethylsulfonyl)phenyl)acetic acid (0.2 g, 0.87 mmol) with 4-(1,1,1,3,3,3-hexafluoro-2-(4-phenylbutoxy)propan-2-yl) aniline (0.17 g, 0.438 mmol) using HATU (0.33 g, 0.876 mmol) and DIEA (0.11 g, 0.876 mmol) as described for the preparation of the compound of example 1.

$^1$H NMR (DMSO-d$_6$, 300 MHz): δ ppm 10.56 (s, 1H), 7.85 (d, J=8.1 Hz, 2H), 7.78 (d, J=8.7 Hz, 2H), 7.61 (d, J=8.1 Hz, 2H), 7.48 (d, J=8.4 Hz, 2H), 7.27 (d, J=7.2 Hz, 2H), 7.19 (d, J=7.2 Hz, 3H), 3.82 (s, 2H), 3.50 (s, 2H), 3.28 (q, J=7.5, 2H), 2.58 (s, 2H), 1.66 (s, 4H), 1.10 (t, J=7.2 Hz, 3H); Mass (ESI): m/z 602.2 [M+H]$^+$.

Example 7

2-(4-(Ethylsulfonyl)phenyl)-N-(4-(1,1,1,3,3,3-hexafluoro-2-hydroxypropan-2-yl)-2-methyl phenyl) acetamide This compound was prepared by the reaction of 2-(4-(ethylsulfonyl)phenyl)acetic acid (0.1 g, 0.438 mmol) with 2-(4-amino-3-methylphenyl)-1,1,1,3,3,3-hexafluoropropan-2-ol (0.12 g, 0.438 mmol) using HATU (0.33 g, 0.876 mmol) and DIEA (0.11 g, 0.876 mmol) as per the process described for the preparation of the compound of example 1.

$^1$H NMR (DMSO-d$_6$, 300 MHz): δ ppm 9.71 (s, 1H), 8.64 (s, 1H), 7.86 (d, J=9.0 Hz, 2H), 7.64 (m, 3H), 7.49 (m, 2H), 3.86 (s, 2H), 3.33 (q, J=7.5 Hz, 2H), 2.24 (s, 3H), 1.11 (t, J=7.5 Hz, 3H); Mass (ESI): m/z 484.5 [M+H]$^+$.

Example 8

2-(4-(Ethylsulfonyl)phenyl)-N-(3-(1,1,1,3,3,3-hexafluoro-2-hydroxypropan-2-yl)phenyl)acetamide This compound was prepared by the reaction of 2-(4-(ethylsulfonyl)phenyl)acetic acid (0.100 g, 0.438 mmol) with 2-(4-amino-3-methylphenyl)-1,1,1,3,3,3-hexafluoropropan-2-ol (0.12 g, 0.438 mmol) using HATU (0.33 g, 0.876 mmol) and DIEA (0.11 g, 0.876 mmol) as per the process described for the preparation of the compound of example 1.

$^1$H NMR (DMSO-d$_6$, 300 MHz): δ ppm 10.48 (s, 1H), 8.71 (s, 1H), 8.03 (s, 1H), 7.85 (d, J=8.1 Hz, 2H), 7.78 (d, J=7.8 Hz, 1H), 7.61 (d, J=8.1 Hz, 2H), 7.47 (m, 1H), 7.36 (d, J=7.5 Hz, 1H), 3.81 (s, 2H), 3.23 (q, J=7.2 Hz, 2H), 1.09 (t, J=7.5 Hz, 3H); Mass (ESI): m/z 470.3 [M+H]$^+$.

Example 9

2-(4-(Ethylsulfonyl)phenyl)-N-(4-(1,1,1-trifluoro-2-hydroxypropan-2-yl)phenyl)acetamide This compound was prepared by the reaction of 2-(4-(ethylsulfonyl)phenyl)acetic acid (0.100 g, 0.438 mmol) with 2-(4-aminophenyl)-1,1,1-trifluoropropan-2-ol (0.09 g, 0.438 mmol) using HATU (0.33 g, 0.876 mmol) and DIEA (0.11 g, 0.876 mmol) as per the process described for the preparation of the compound of example 1.

$^1$H NMR (DMSO-d$_6$, 300 MHz): δ ppm 10.33 (s, 1H), 7.84 (d, J=8.4 Hz, 2H), 7.60 (d, J=9.6 Hz, 4H), 7.50 (d, J=8.7 Hz, 2H), 6.50 (s, 1H), 3.78 (s, 2H), 3.32 (q, J=7.5 Hz, 2H), 1.63 (s, 3H), 1.10 (t, J=7.2 Hz, 3H); Mass (ESI): m/z 416.4 [M+H]$^+$.

Example 10

2-(4-(Ethylsulfonyl)phenyl)-N-(4-(2,2,2-trifluoro-1-hydroxyethyl)phenyl)acetamide The title compound was prepared by the reaction of 2-(4-(ethylsulfonyl)phenyl)acetic acid (0.100 g, 0.438 mmol) with 1-(4-aminophenyl)-2,2,2-trifluoroethanol (0.084 g, 0.438 mmol) using HATU (0.33 g, 0.876 mmol) and DIEA (0.11 g, 0.876 mmol) as per the process described for the preparation of the compound of example 1.

$^1$H NMR (DMSO-d$_6$, 300 MHz): δ ppm 10.34 (s, 1H), 8.16 (s, 1H), 7.84 (d, J=8.1 Hz, 4H), 7.60 (d, J=7.5 Hz, 4H), 7.40 (d, J=8.1 Hz, 2H), 6.76 (d, J=5.4 Hz, 1H), 5.06 (m, 1H), 3.79 (s, 2H), 3.32 (q, J=9.0 Hz, 2H), 1.10 (t, J=7.2 Hz, 3H); Mass (ESI): m/z 402.2 [M+H]$^+$.

Example 11

N-(4-(2-(2-Cyclohexylethoxy)-1,1,1,3,3,3-hexafluoropropan-2-yl)phenyl)-2-(4-(ethylsulfonyl) phenyl) acetamide The title compound was prepared by the reaction of 2-(4-(ethylsulfonyl)phenyl)acetic acid (0.100 g, 0.438 mmol) with 4-(2-(2-cyclohexylethoxy)-1,1,1,3,3,3-hexafluoropropan-2-yl)aniline (0.162 g, 0.438 mmol) using HATU (0.33 g, 0.876 mmol) and DIEA (0.11 g, 0.876 mmol) as per the process analogous to the preparation of the compound of example 1.

$^1$H NMR (DMSO-d$_6$, 300 MHz): δ ppm 10.56 (s, 1H), 7.84 (d, J=7.5 Hz, 2H), 7.78 (d, J=8.4 Hz, 2H), 7.61 (d, J=7.8 Hz, 2H), 3.82 (s, 2H), 3.50 (m, 2H), 3.27 (q, J=6.0 Hz, 2H), 1.64 (m, 7H), 1.38 (m, 1H), 1.13 (m, 6H); Mass (ESI): m/z 580.4 [M+H]$^+$.

Example 12

2-(4-(Ethylsulfonyl)phenyl)-N-(4-(1,1,1,3,3,3-hexafluoro-2-(2-(piperidin-1-yl)ethoxy) propan-2-yl) phenyl)acetamide The title compound was prepared by the reaction of 2-(4-(ethylsulfonyl)phenyl)acetic acid (0.100 g, 0.438 mmol) with 4-(1,1,1,3,3,3-hexafluoro-2-(2-(piperidin-1-yl) ethoxy)propan-2-yl)aniline (0.16 g, 0.438 mmol) using HATU (0.33 g, 0.876 mmol) and DIEA (0.11 g, 0.876 mmol) as per the process described for the preparation of the compound of example 1.

$^1$H NMR (DMSO-$d_6$, 300 MHz): δ ppm 10.56 (s, 1H), 7.85 (dd, J=8.7, 7.8 Hz, 4H), 7.65 (m, 4H), 3.82 (s, 2H), 3.55 (m, 2H), 3.25 (q, J=7.2 Hz, 2H), 2.56 (m, 2H), 2.34 (m, 4H), 1.50 (m, 4H), 1.38 (m, 2H), 1.08 (t, J=7.5 Hz, 3H); Mass (ESI): m/z 580.3 [M+H]$^+$.

Example 13

2-(4-(Ethylsulfonyl)phenyl)-N-(4-(1,1,1,3,3,3-hexafluoro-2-hydroxypropan-2-yl)phenyl) acetamide The title compound was prepared by the reaction of 2-(4-(ethylsulfonyl)phenyl)acetic acid (0.200 g, 0.876 mmol) with 2-(4-aminophenyl)-1,1,1,3,3,3-hexafluoropropan-2-ol (0.227 g, 0.876 mmol) using HATU (0.66 g, 1.75 mmol) and DIEA (0.22 g, 1.75 mmol) as per the process described for the preparation of the compound of example 1.

$^1$H NMR (DMSO-$d_6$, 300 MHz): δ ppm 10.49 (s, 1H), 8.62 (s, 1H), 7.85 (d, J=7.8 Hz, 2H), 7.72 (d, J=8.4 Hz, 2H), 7.61 (d, J=8.1 Hz, 4H), 3.82 (s, 2H), 3.23 (q, J=7.5 Hz, 2H), 1.11 (t, J=7.2 Hz, 3H); Mass (ESI): m/z 470.0 [M+H]$^+$.

Example 14

2-(4-(Ethylsulfonyl)phenyl)-1-(4-(4-(1,1,1,3,3,3-hexafluoro-2-hydroxypropan-2-yl)phenyl) piperazin-1-yl)ethanone The title compound was prepared by the reaction of 2-(4-(ethylsulfonyl)phenyl)acetic acid (0.200 g, 0.876 mmol) with 1,1,1,3,3,3-hexafluoro-2-(4-(piperazin-1-yl)phenyl)propan-2-ol (0.287 g, 0.876 mmol) using HATU (0.66 g, 1.75 mmol) and DIEA (0.22 g, 1.75 mmol) as per the process described for the preparation of the compound of example 1.

$^1$H NMR (DMSO-$d_6$, 300 MHz): δ ppm 8.43 (s, 1H), 7.82 (d, J=7.8 Hz, 2H), 7.52 (d, J=8.7 Hz, 4H), 7.04 (d, J=9.0 Hz, 2H), 3.92 (s, 2H), 3.62 (m, 4H), 3.25 (q, J=7.5 Hz, 2H), 3.20 (m, 4H), 1.11 (t, J=7.2 Hz, 3H).

Example 15

2-(4-(Ethylsulfonyl)phenyl)-N-(5-oxo-5,6,7,8-tetrahydronaphthalen-2-yl)acetamide The title compound was prepared by the reaction of 2-(4-(ethylsulfonyl)phenyl)acetic acid (1.0 g, 4.38 mmol) with 6-amino-3,4-dihydronaphthalen-1(2H)-one (0.70 g, 4.38 mmol) in the presence HATU (3.33 g, 8.76 mmol), DIEA (1.13 g, 8.76 mmol) as per the process described for the preparation of the compound of example 1.

$^1$H NMR (DMSO-$d_6$, 300 MHz): δ ppm 10.54 (s, 1H), 7.83 (m, 3H), 7.61 (m, 3H), 7.49 (d, J=8.7 Hz, 1H), 3.83 (s, 2H), 3.38 (q, J=7.5 Hz, 2H), 2.87-2.85 (m, 2H), 2.55-2.53 (m, 2H), 2.01-1.98 (m, 2H); 1.08 (t, J=7.5 Hz, 3H); Mass (ESI): m/z 372.1 [M+H]$^+$.

Example 16

2-(4-(Ethylsulfonyl)phenyl)-N-(5,6,7,8-tetrahydronaphthalen-2-yl)acetamide

The title compound was prepared by the reaction of 2-(4-(ethylsulfonyl)phenyl)acetic acid (0.124 g, 0.543 mmol) with 5,6,7,8-tetrahydronaphthalen-2-amine (0.080 g, 0.544 mmol) using HATU (0.413 g, 1.08 mmol) and DIEA (0.140 g, 1.0 mmol) as per the process described for preparation of the compound of example 1.

$^1$H NMR (DMSO-$d_6$, 300 MHz): δ ppm 10.08 (s, 1H), 7.84 (d, J=8.4 Hz, 2H), 7.59 (d, J=8.1 Hz, 2H), 7.30 (m, 2H), 6.96 (d, J=8.1 Hz, 1H), 3.74 (s, 2H), 3.25 (q, J=7.2 Hz, 2H), 2.72 (m, 4H), 1.69 (m, 4H), 1.08 (t, J=7.5 Hz, 3H); Mass (ESI): m/z 359.8 [M+H]$^+$.

Example 17

N-(4-(2-Cyanopropan-2-yl)phenyl)-2-(4-(ethylsulfonyl)phenyl)acetamide

The title compound was prepared by the reaction of 2-(4-(ethylsulfonyl)phenyl)acetic acid (0.1 g, 0.43 mmol) with 2-(4-aminophenyl)-2-methylpropanenitrile (0.070 g, 0.438 mmol) using oxalyl chloride (0.067 g, 0.826 mmol) and TEA (0.067 g, 0.52 mmol) as per the process described for the preparation of the compound of example 1.

$^1$H NMR (DMSO-$d_6$, 500 MHz): δ ppm 10.36 (s, 1H), 7.85 (d, J=8.0 Hz, 2H), 7.62 (dd, J=8.0, 13.5 Hz, 4H), 7.45 (d, J=8.5 Hz, 2H), 3.80 (s, 2H), 3.28 (q, J=7.5 Hz, 2H), 1.65 (s, 6H); 1.10 (t, J=7.5 Hz, 3H); Mass (ESI): m/z 393.7 [M+Na]$^+$.

Example 18

2-(4-(Ethylsulfonyl)phenyl)-N-(3-(1,1,1,3,3,3-hexafluoro-2-hydroxypropan-2-yl)-5,6,7,8-tetrahydronaphthalen-2-yl)acetamide The title compound was prepared analogous to the process described in example 1 by the reaction of 2-(3-amino-5,6,7,8-tetrahydronaphthalen-2-yl)-1,1,1,3,3,3-hexafluoropropan-2-ol with 2-(4-(ethylsulfonyl)phenyl)acetic acid.

$^1$H NMR (DMSO-$d_6$, 300 MHz): δ ppm 9.98 (bs, 1H), 7.84 (d, J=8.1 Hz, 3H), 7.57 (d, J=8.1 Hz, 2H), 7.10 (s, 1H), 3.73 (s, 2H), 3.32-3.22 (m, 3H), 2.72 (bs, 4H), 1.66 (bs, 4H), 1.10 (t, J=7.5 Hz, 3H); Mass (ESI): m/z 524 [M+H]$^+$.

Example 19

2-(4-(Ethylsulfonyl)phenyl)-N-(4-phenylcyclohexyl) acetamide

To a stirred solution of 4-phenylcyclohexanamine (100 mg, 0.571 mmol) and 2-(4-(ethylsulfonyl)phenyl)acetic acid (130 mg, 0.571 mmol) in dry DCM (5 mL) were added EDC.HCl (131 mg, 0.685 mmol) and HOBt (77 mg, 0.571 mmol) and the reaction mixture was stirred for 16 hours at RT. The reaction mixture was quenched with water (10 mL), extracted with ethyl acetate (20 mL). The organic layer was washed with water (10 mL), brine (10 mL), dried over sodium sulphate, concentrated and purified by flash column chromatography (silica gel, hexane and ethyl acetate) to obtain the title compound.

Yield: 110 mg (50%); $^1$H NMR (DMSO-$d_6$, 300 MHz): δ ppm 1.08 (t, J=6.0 Hz, 3H), 1.22-1.36 (m, 2H), 1.43-1.56 (m, 2H), 1.75-1.89 (m, 4H), 3.28 (q, J=3.0 Hz, 2H), 3.52 (s, 2H), 7.14-7.25 (m, 5H), 7.51 (d, J=9.0 Hz, 2H), 7.80 (d, J=9.0 Hz, 2H), 8.12 (d, J=9.0 Hz, 1H); Mass (ESI): m/z 386.1 [M+H]$^+$.

Example 20

N-(4-(1,1,1,3,3,3-Hexafluoro-2-hydroxypropan-2-yl) phenyl)-2-(4-(2-oxopyrrolidin-1-yl) phenyl)acetamide This compound was prepared by the reaction of 2-(4-(2-oxopyrrolidin-1-yl)phenyl)acetic acid (I-2) with 2-(4-aminophenyl)-1,1,1,3,3,3-hexafluoropropan-2-ol (220 mg, 0.860 mmol) using EDC (200 mg, 1.03 mmol), HOBt (130 mg, 0.86 mmol) in dry DCM (5 mL) as per the process described for the preparation of the compound of example 19.

$^1$H NMR (DMSO-d$_6$, 300 MHz): δ ppm 1.68-1.73 (m, 2H), 2.32 (t, J=7.5 Hz, 2H), 3.38-3.44 (m, 2H), 3.58 (s, 2H), 7.23 (d, J=8.1 Hz, 2H), 7.52 (d, J=9.0 Hz, 2H), 7.58 (d, J=9.0 Hz, 2H), 7.71 (d, J=9.0 Hz, 2H), 8.60 (s, 1H), 10.35 (s, 1H); Mass (ESI): m/z 461.6 [M+H]$^+$.

Example 21

2-(4-Acetamidophenyl)-N-(4-(1,1,1,3,3,3-hexafluoro-2-hydroxypropan-2-yl)phenyl) acetamide This compound was prepared by the reaction of 2-(4-acetamidophenyl)acetic acid (I-3, 0.10 g, 0.52 mmol) with 2-(4-aminophenyl)-1,1,1,3,3,3-hexafluoropropan-2-ol (0.13 g, 0.52 mmol) using EDC.HCl (0.12 g, 0.62 mmol), HOBt (0.08 g, 0.52 mmol) in dry DCM (5 mL) as per the process described for the preparation of the compound of example 19.

Yield: 0.080 g (35%); $^1$H NMR (DMSO-d$_6$, 300 MHz): δ ppm 2.01 (s, 3H), 3.58 (s, 2H), 7.23 (d, J=8.4 Hz, 2H), 7.51 (d, J=9.0 Hz, 2H), 7.59 (d, J=9.0 Hz, 2H), 7.71 (d, J=9.0 Hz, 2H), 8.60 (s, 1H), 9.90 (s, 1H), 10.35 (s, 1H); Mass (ESI): m/z 435.3 [M+H]$^+$.

Example 22

N-(4-(2-((4-(1,1,1,3,3,3-Hexafluoro-2-hydroxypropan-2-yl)phenyl)amino)-2-oxoethyl) phenyl)-N-methylpivalamide This compound was prepared by the reaction of 2-(4-(N-methylpivalamido)phenyl)acetic acid (I-4, 0.05 g, 0.20 mmol) with 2-(4-aminophenyl)-1,1,1,3,3,3-hexafluoropropan-2-ol (0.05 g, 0.20 mmol) using EDC (0.05 g, 0.24 mmol), HOBt (0.03 g, 0.20 mmol) in dry DCM (4 mL) as per the process described for the preparation of the compound of example 19. Yield: 0.02 g (20%); $^1$H NMR (DMSO-d$_6$, 300 MHz): δ ppm 1.21 (d, 9H), 3.07 (s, 3H), 3.70 (s, 2H), 7.26 (d, J=9.0 Hz, 2H), 7.37 (d, J=9.0 Hz, 2H), 7.60 (d, J=9.0 Hz, 2H), 7.72 (d, J=9.0 Hz, 2H), 8.61 (s, 1H), 10.43 (s, 1H). Mass (ESI): m/z 491.3 [M+H]$^+$.

Example 23

N-(4-(Cyclohexyloxy)-3-(trifluoromethyl)phenyl)-2-(4-(ethylsulfonyl)phenyl)acetamide This compound was prepared by the reaction of 4-(cyclohexyloxy)-3-(trifluoromethyl)aniline (I-5, 40 mg, 0.15 mmol) with 2-(4-(ethylsulfonyl) phenyl) acetic acid (30 mg, 0.15 mmol) using EDC.HCl (30 mg, 0.18 mmol), 1H-benzo[d][1,2,3]triazol-1-ol (77 mg, 0.15 mmol) in DCM (4 mL) as per the process described for the preparation of the compound of example 19.

Yield: 24 mg (35.0%); $^1$H NMR (DMSO-d$_6$, 300 MHz): δ ppm 1.08 (t, J=6.0 Hz, 3H), 1.23-1.48 (m, 6H), 1.65-1.82 (m, 4H), 3.23-3.28 (m, 2H), 3.77 (s, 2H), 4.48-4.52 (m, 1H), 7.25 (d, J=9.0 Hz, 1H), 7.58 (d, J=9.0 Hz, 2H), 7.68-7.71 (m, 1H), 7.83 (d, J=9.0 Hz, 2H), 7.91 (s, 1H), 10.35 (s, 1H); Mass (ESI): m/z 470.5 [M+H]$^+$.

Example 24

2-(4-(Ethylsulfonyl)phenyl)-N-(4'-oxo-2-(trifluoromethyl)-2',3',4',5'-tetrahydro-[1,1'-biphenyl]-4-yl) acetamide This compound was prepared by the reaction of 4'-amino-2'-(trifluoromethyl)-5,6-dihydro-[1,1'-biphenyl]-4(3H)-one (I-12, 80 mg, 0.313 mmol) with 2-(4-(ethylsulfonyl)phenyl) acetic acid (71.5 mg, 0.313 mmol) using EDC.HCl (71.8 mg, 0.376 mmol), HOBt (42.4 mg, 0.313 mmol) in DCM (4 mL) as per the process described for the preparation of the compound of example 19.

Yield: 71 mg (50%); $^1$H NMR (DMSO-d$_6$, 300 MHz): δ ppm 1.07 (t, J=6.0 Hz, 3H), 2.48-2.61 (m, 4H), 2.96 (br s, 2H), 3.26 (q, J=6.0 Hz, 2H), 3.82 (s, 2H), 5.59 (br s, 1H), 7.34 (d, J=9.0 Hz, 1H), 7.59 (d, J=9.0 Hz, 2H), 7.76 (d, J=9.0 Hz, 1H), 7.83 (d, J=9.0 Hz, 2H), 8.04 (s, 1H), 10.59 (s, 1H); Mass (ESI): m/z 466.1 [M+H]$^+$.

Example 25

N-(4-Cyclohexylphenyl)-2-(4-(ethylsulfonyl)phenyl) acetamide

The title compound was prepared by the reaction of 2-(4-(ethylsulfonyl)phenyl)acetic acid (130 mg, 0.571 mmol) and 4-phenylcyclohexanamine (100 mg, 0.571 mmol) in presence of EDC.HCl (131 mg, 0.685 mmol) and HOBt (77 mg, 0.571 mmol) analogous to the process described for the preparation of the compound of example 19.

$^1$H NMR (DMSO-d$_6$, 300 MHz): δ ppm 1.08 (t, J=6.0 Hz, 3H), 1.22-1.37 (m, 5H), 1.66-1.74 (m, 5H), 2.40-2.42 (m, 1H), 3.22-3.27 (m, 2H), 3.76 (s, 2H), 7.12 (d, J=9.0 Hz, 2H), 7.47 (d, J=9.0 Hz, 2H), 7.58 (d, J=9.0 Hz, 2H), 7.83 (d, J=9.0 Hz, 2H), 10.17 (s, 1H); Mass (ESI): m/z 386.2 [M+H]$^+$.

Example 26

2-(4-(Ethylsulfonyl)phenyl)-N-(4-(1,1,3,3,3-hexafluoro-2-hydroxypropan-2-yl)benzyl) acetamide To a solution of 2-(4-(ethylsulfonyl)phenyl)acetic acid (36.8 mg, 0.161 mmol), EDC.HCl (42.1 mg, 0.220 mmol), HOBt (29.2 mg, 0.190 mmol) in tetrahydrofuran (5 mL) was added DIEA (0.051 mL, 0.293 mmol) and stirred for half an hour. To the reaction mixture 2-(4-(aminomethyl)phenyl)-1,1,1,3,3,3-hexafluoropropan-2-ol (I-6, 40 mg, 0.146 mmol) was added and stirred for 16 hours. After completion of the reaction, the reaction mixture was evaporated to remove the solvent, added water and extracted with ethyl acetate. The organic layer was dried over sodium sulphate and evaporated to obtain crude mass. The crude mass obtained was purified by column chromatography (silica gel, hexane and ethyl acetate).

$^1$H NMR (DMSO-d$_6$, 300 MHz): δ ppm 8.73-8.68 (m, 2H), 7.82 (d, J=8.1 Hz, 2H), 7.61 (d, J=7.8 Hz, 2H), 7.55 (d, J=8.1 Hz, 2H), 7.36 (d, J=8.4 Hz, 2H), 4.31 (d, J=5.7 Hz, 2H), 3.63 (s, 2H), 3.27-3.22 (m, 2H), 1.09 (t, J=7.2 Hz, 3H); Mass (ESI): m/z 484 [M+H]$^+$.

Example 27

N-(4-(1,1,1,3,3,3-Hexafluoro-2-hydroxypropan-2-yl) phenyl)-2-(4-(morpholinosulfonyl) phenyl)acetamide This compound was prepared by the reaction of 2-(4-(morpholinosulfonyl)phenyl)acetic acid (I-9, 75 mg, 0.263 mmol) with 2-(4-aminophenyl)-1,1,1,3,3,3-hexafluoropropan-2-ol (68.1 mg, 0.263 mmol) using EDC.HCl (76 mg, 0.394 mmol), HOBt (60.4 mg, 0.394 mmol) and DIEA (0.092 mL, 0.526 mmol) in DCM (5 mL) as per the process described for the preparation of the compound of example 26.

$^1$H NMR (DMSO-d$_6$, 300 MHz): δ ppm 10.50 (s, 1H), 8.63 (s, 1H), 7.73-7.69 (m, 4H), 7.61 (d, J=6.9 Hz, 4H), 3.82 (s, 2H), 3.61 (bs, 4H), 2.84 (bs, 4H); Mass (ESI): m/z 527 [M+H]$^+$.

Example 28

N-(5-Cyclohexylidene-5,6,7,8-tetrahydronaphthalen-2-yl)-2-(4-(ethylsulfonyl)phenyl) acetamide This compound was prepared by the reaction of 5-cyclohexylidene-5,6,7,8-tetrahydronaphthalen-2-amine (I-13, 0.2 g, 0.880 mmol) with 2-(4-(ethylsulfonyl)phenyl)acetic acid (0.201 g, 0.880 mmol) using EDC.HCl (0.205 g, 1.320 mmol), HOBt (0.202 g, 1.320 mmol), DIEA (0.154 mL, 0.880 mmol) in anhydrous THF as per the process described for the preparation of the compound of example 26.

$^1$H NMR (DMSO-d$_6$, 300 MHz): δ ppm 1.67-1.54 (m, 8H), 2.39-2.22 (m, 8H), 3.28 (t, 2H), 3.76 (s, 2H), 7.07-7.04 (d, J=8.4 Hz, 1H), 7.33-7.30 (d, J=8.4 Hz, 1H), 7.39 (s, 1H), 7.60-7.58 (d, J=8.4 Hz, 2H), 7.84-7.82 (d, J=8.1 Hz, 2H), 10.19 (s, 1H); Mass (ESI): m/z 438 [M+H]$^+$.

Example 29

2-(4-(Ethylsulfonyl)phenyl)-N-(4-oxochroman-6-yl) acetamide

This compound was prepared by the reaction of 2-(4-(ethylsulfonyl)phenyl)acetic acid (1.119 g, 4.90 mmol) with 6-aminochroman-4-one (I-14, 0.8 g, 4.90 mmol) using EDC.HCl (1.410 g, 7.35 mmol), HOBt (1.126 g, 7.35 mmol) and DIEA (2.141 mL, 12.26 mmol) in dry THF (20 mL) as per the process described for the preparation of the compound of example 26.

$^1$H NMR (DMSO-d$_6$, 300 MHz): δ ppm 10.31 (bs, 1H), 8.02 (d, J=2.4 Hz, 1H), 7.84 (d, J=8.1 Hz, 2H), 7.71 (dd, J=2.4 & 8.7 Hz, 1H), 7.60 (d, J=8.1 Hz, 2H), 7.01 (d, J=9.0 Hz, 1H), 4.50 (t, J=6.3 & 6.3 Hz, 2H), 3.76 (s, 2H), 3.30 (q, J=7.5 & 7.2 Hz, 2H), 2.78 (t, J=6.6 & 6.3 Hz, 2H), 1.10 (t, J=7.2 & 7.2 Hz, 3H); Mass (ESI): m/z 374 [M+H]$^+$.

Example 30

N-(4-(1,1,1,3,3,3-Hexafluoro-2-hydroxypropan-2-yl) phenyl)-2-(thiochroman-6-yl) acetamide The title compound was prepared by the reaction of 2-(4-aminophenyl)-1,1,1,3,3,3-hexafluoropropan-2-ol (0.062 g, 0.240 mmol) with 2-(thiochroman-6-yl)acetic acid (0.05 g, 0.240 mmol) using EDC.HCl (0.69 g, 0.36 mmol), HOBt (0.55 g, 0.360 mmol) and DIPEA (0.210 mL, 1.2 mmol) as per the process described for the preparation of the compound of example 26.

$^1$H NMR (DMSO-d$_6$, 300 MHz): δ ppm 1.99-1.97 (s, 2H), 2.75-2.71 (t, 2H), 2.99 (t, 2H), 3.57 (s, 2H), 7.00-6.95 (m, 3H), 7.60-7.57 (d, J=8.7 Hz, 2H), 7.72-7.69 (d, J=9 Hz, 2H) 8.609 (s, 1H), 10.34 (s, 1H); Mass (ESI): m/z 450 [M+H]$^+$.

Example 31

N-(4-Ethyl-3-oxo-3,4-dihydro-2H-benzo[b][1,4] oxazin-7-yl)-2-(4-(ethylsulfonyl)phenyl) acetamide The title compound was prepared analogous to the process described in example 26 by the reaction of 7-amino-4-ethyl-2H-benzo[b][1,4]oxazin-3(4H)-one with 2-(4-(ethylsulfonyl) phenyl)acetic acid.

$^1$H NMR (DMSO-d$_6$, 300 MHz): δ ppm 10.27 (s, 1H), 7.85 (d, J=8.1 Hz, 2H), 7.60 (d, J=8.1 Hz, 2H), 7.35 (d, J=2.1 Hz, 1H), 7.24 (d, J=8.7 Hz, 1H), 7.16 (d, J=9.0 Hz, 1H), 4.59 (s, 2H), 3.92 (q, J=6.9 & 7.2 Hz, 2H), 3.77 (s, 2H), 3.30 (q, J=7.5 & 7.2 Hz, 2H), 1.14 (t, J=7.5 & 7.2 Hz, 3H), 1.09 (t, J=7.5 & 7.2 Hz, 3H); Mass (ESI): m/z 403 [M+H]$^+$.

Example 32

2-(4-(Ethylsulfonyl)phenyl)-N-(4-(4-methoxybenzyl)-3-oxo-3,4-dihydro-2H-benzo[b][1,4]oxazin-7-yl)acetamide The title compound was prepared analogous to the process described in example 26 by the reaction of 7-amino-4-(4-methoxybenzyl)-2H-benzo[b][1,4]oxazin-3(4H)-one with 2-(4-(ethylsulfonyl)phenyl)acetic acid.

$^1$H NMR (DMSO-d$_6$, 300 MHz): δ ppm 10.23 (s, 1H), 7.83 (d, J=7.8 Hz, 2H), 7.58 (d, J=8.1 Hz, 2H), 7.35 (s, 1H), 7.21 (d, J=8.4 Hz, 2H), 7.10 (d, J=8.7 Hz, 1H), 7.02 (d, J=8.7 Hz, 1H), 6.88 (d, J=8.4 Hz, 2H), 5.04 (s, 2H), 4.73 (s, 2H), 3.74 (s, 2H), 3.70 (s, 3H), 3.29 (q, J=7.5 & 7.2 Hz, 2H), 1.10 (t, J=7.5 & 7.2 Hz, 3H); Mass (ESI): m/z 495 [M+H]$^+$.

Example 33

2-(4-(Ethylsulfonyl)phenyl)-N-(4-hydroxythiochroman-6-yl)acetamide

To a solution of 2-(4-(ethylsulfonyl)phenyl)-N-(4-oxothiochroman-6-yl)acetamide (Example 3, 100 mg, 0.257 mmol) in methanol (5 mL) was added sodium borohydride (14.57 mg, 0.385 mmol) at 0° C. and the reaction mixture was stirred for 2 hours. After completion of the reaction, the reaction mixture was quenched with water. The reaction mixture was evaporated and the residue obtained was dissolved in ethyl acetate and washed with water. The organic layer was dried over sodium sulphate and evaporated to obtain the crude material. The crude material obtained was purified by column chromatography (silica gel, hexane and ethyl acetate).

$^1$H NMR (DMSO-d$_6$, 300 MHz): δ ppm 10.19 (s, 1H), 7.84 (d, J=4.2 Hz, 2H), 7.61 (d, J=4.2 Hz, 2H), 7.57 (s, 1H), 7.42 (d, J=8.4 Hz, 1H), 6.98 (d, J=8.7 Hz, 1H), 5.39 (d, J=5.4 Hz, 1H), 4.52-4.50 (m, 1H), 3.75 (s, 2H), 3.30-3.22 (m, 2H), 3.10-3.08 (m, 1H), 2.89-2.72 (m, 1H), 2.00-1.98 (m, 2H), 1.1 (t, J=7.2 Hz, 3H); Mass (ESI): m/z 374 [M−18].

Example 34

2-(4-(Ethylsulfonyl)phenyl)-N-(4'-hydroxy-2-(trifluoromethyl)-2',3',4',5'-tetrahydro-[1,1'-biphenyl]-4-yl)acetamide To a stirred solution of 2-(4-(ethylsulfonyl)phenyl)-N-(4'-oxo-2-(trifluoromethyl)-2',3',4',5'-tetrahydro-[1,1'-biphenyl]-4-yl)acetamide (Example 24, 50 mg, 0.11 mmol) in methanol (2 mL) was added sodium borohydride (10 mg, 0.13 mmol) portion wise at 0° C. and the reaction mixture was stirred at RT for 1 hour. The reaction mixture was distilled off, acidified and extracted with ethyl acetate (10 mL). The organic layer was washed with brine (10 mL), dried over sodium sulphate, concentrated and purified by flash column chromatography (silica gel, hexane and ethyl acetate) to obtain the title compound.

Yield: 32 mg (64%); $^1$H NMR (DMSO-$d_6$, 300 MHz): δ ppm 1.07 (t, J=6.0 Hz, 3H), 1.49-1.57 (m, 1H), 1.75-1.97 (m, 3H), 2.22-2.29 (m, 2H), 3.26 (q, J=6.0 Hz, 2H), 3.71-3.76 (m, 1H), 3.80 (s, 2H), 4.69 (d, J=3.0 Hz, 1H), 5.36 (br s, 1H), 7.24 (d, J=9.0 Hz, 1H), 7.58 (d, J=9.0 Hz, 2H), 7.72 (d, J=9.0 Hz, 1H), 7.83 (d, J=9.0 Hz, 2H), 7.99 (s, 1H), 10.55 (s, 1H); Mass (ESI): m/z 465.7 [M–H]$^+$.

Example 35

N-(5-Cyclohexyl-5,6,7,8-tetrahydronaphthalen-2-yl)-2-(4-(ethylsulfonyl) phenyl)acetamide To a solution of N-(5-cyclohexylidene-5,6,7,8-tetrahydronaphthalen-2-yl)-2-(4-(ethylsulfonyl) phenyl)acetamide (Example 28, 0.06 g, 0.137 mmol) in ethanol (2 mL), ethyl acetate (2 mL) was added Pd—C (0.018 g, 0.169 mmol) under hydrogen atmosphere and the reaction mixture was stirred for 16 hours at room temperature. The reaction mixture was filtered through celite bed and the filtrate was concentrated to obtain the crude solid. The solid obtained was purified by precipitation method.

$^1$H NMR (DMSO-$d_6$, 300 MHz): δ ppm 1.10-1.08 (m, 1H), 1.15 (m, 3H), 1.157-1.68 (m, 15H), 2.59 (s, 2H), 3.33-3 (q, 2H), 3.74 (s, 2H), 7.08-7.06 (d, J=7.2 Hz, 1H), 7.28-7.25 (m, 2H), 7.59-7.57 (d, J=8.4 Hz, 2H), 7.84-7.82 (d, J=6.6 Hz, 2H), 10.09 (s, 1H); Mass (ESI): m/z 440 [M+H]$^+$.

Example 36

2-(4-(Ethylsulfonyl)phenyl)-N-(4-hydroxychroman-6-yl)acetamide

To a solution of 2-(4-(ethylsulfonyl)phenyl)-N-(4-oxochroman-6-yl)acetamide (Example 29, 500 mg, 1.339 mmol) in ethanol was added sodium borohydride (76 mg, 2.008 mmol) at 0° C. The reaction mixture was stirred for 1.5 hours, added water and the volatiles are removed. The reaction mixture was extracted with dichloromethane and the organic layer was dried over sodium sulphate, filtered and concentrated. The crude product obtained was purified by flash column chromatography (silica gel, hexane and ethyl acetate).

$^1$H NMR (DMSO-$d_6$, 300 MHz): δ ppm 10.08 (bs, 1H), 7.85 (d, J=8.1 Hz, 2H), 7.60 (d, J=8.4 Hz, 2H), 7.55 (d, J=2.1 Hz, 1H), 7.33 (dd, J=2.4 & 8.7 Hz 1H), 6.68 (d, J=8.7 Hz, 1H), 5.37 (d, J=5.7 Hz, 1H), 4.55 (t, J=4.8 & 4.8 Hz, 1H), 4.14 (t, J=6.0 & 4.5 Hz, 1H), 3.73 (s, 2H), 3.30 (q, J=7.5 & 7.2 Hz, 2H), 1.97 (m, 2H), 1.11 (t, J=7.2 & 7.5 Hz, 3H); Mass (ESI): m/z 358 [M–H$_2$O].

Example 37

N-(7,8-Dihydronaphthalen-2-yl)-2-(4-(ethylsulfonyl)phenyl)acetamide

The title compound was prepared analogous to the process described in the preparation of the compound of example 36 by reduction of 2-(4-(ethylsulfonyl)phenyl)-N-(5-oxo-5,6,7,8-tetrahydronaphthalen-2-yl)acetamide (Example 15) followed by dehydration.

$^1$H NMR (DMSO-$d_6$, 300 MHz): δ ppm 10.20 (s, 1H), 7.84 (d, J=8.1 Hz, 2H), 7.60 (d, J=8.1 Hz, 2H), 7.37 (m, 2H), 6.97 (d, J=8.7 Hz, 1H), 6.42 (d, J=9.6 Hz, 1H), 5.95-5.91 (m, 1H), 3.76 (s, 2H), 3.25 (q, J=7.2 Hz, 2H), 2.70 (t, J=8.4 Hz, 2H), 2.21 (m, 2H), 1.08 (t, J=7.5 Hz, 3H); Mass (ESI): m/z 356.6 [M+H]$^+$.

Example 38

2-(4-(Ethylsulfonyl)phenyl)-N-(5-hydroxy-5,6,7,8-tetrahydronaphthalen-2-yl)acetamide The title compound was prepared analogous to the process described in the preparation of the compound of example 36 by reduction of 2-(4-(ethylsulfonyl)phenyl)-N-(5-oxo-5,6,7,8-tetrahydronaphthalen-2-yl)acetamide (Example 15).

$^1$H NMR (DMSO-$d_6$, 300 MHz): δ ppm 10.12 (s, 1H), 7.84 (d, J=8.1 Hz, 2H), 7.60 (d, J=8.1 Hz, 2H), 7.30 (m, 3H), 5.00 (d, J=5.7 Hz, 1H), 4.49 (m, 1H), 3.76 (s, 2H), 3.25 (q, J=7.2 Hz, 2H), 2.60 (m, 2H), 1.83 (m, 2H), 1.64 (m, 2H), 1.08 (t, J=7.5 Hz, 3H); Mass (ESI): m/z 355.4 [M–OH].

Example 39

2-(4-(Ethylsulfonyl)phenyl)-N-(4-(1-hydroxy-1-phenylethyl)phenyl)acetamide

Step 1: N-(4-Benzoylphenyl)-2-(4-(ethylsulfonyl)phenyl)acetamide

This compound was prepared by the reaction of (4-aminophenyl)(phenyl)methanone (1 g, 5.07 mmol) with 2-(4-(ethylsulfonyl)phenyl)acetic acid (1.157 g, 5.07 mmol) using EDC.HCl (1.162 g, 6.08 mmol), HOBt (0.685 g, 5.07 mmol) in DCM (15 mL) as per the process described for the preparation of the compound of example 19.

Yield: 0.85 g (41%); $^1$H NMR (DMSO-$d_6$, 300 MHz): δ ppm 1.09 (t, J=6.0 Hz, 3H), 1.43-1.56 (m, 2H), 3.23-3.31 (m, 2H), 3.86 (s, 2H), 7.50-7.79 (m, 12H), 7.85 (d, J=9.0 Hz, 2H); Mass (ESI): m/z 408.9 [M+H]$^+$.

Step 2

N-(4-Benzoylphenyl)-2-(4-(ethylsulfonyl)phenyl)acetamide (0.100 g, 0.25 mmol), as obtained in step 1, was stirred in dry THF (5 mL) at 0° C. under nitrogen atmosphere. To this was added methyl magnesium bromide (0.12 g, 1.0 mmol) drop wise and the reaction mixture was stirred at RT for 12 hours. The reaction mixture was quenched with saturated ammonium chloride solution (2 mL), and extracted with ethyl acetate (10 mL). The organic layer was washed with brine (10 mL), dried over sodium sulphate, concentrated and purified by flash column chromatography (silica gel, ethyl acetate and hexane) to obtain the title compound.

Yield: 0.040 g (40%); $^1$H NMR (DMSO-$d_6$, 300 MHz): δ ppm 1.08 (t, J=6.0 Hz, 3H), 1.78 (s, 3H), 3.22-3.29 (m, 2H), 3.76 (s, 2H), 5.63 (s, 1H), 7.14 (t, J=6.0 Hz, 1H), 7.22-7.27 (m, 2H), 7.31-7.39 (m, 4H), 7.46 (d, J=9.0 Hz, 2H), 7.57 (d, J=9.0 Hz, 2H), 7.68 (s, 1H), 7.82 (d, J=9.0 Hz, 2H); Mass (ESI): m/z 424.5 [M+H]$^+$.

Example 40

N-(4-Ethyl-4-hydroxychroman-6-yl)-2-(4-(ethylsulfonyl)phenyl)acetamide

A solution of ethylmagnesium bromide (2.142 mL, 2.142 mmol) was slowly added to a solution of 2-(4-(ethylsulfonyl)phenyl)-N-(4-oxochroman-6-yl)acetamide (Example 29, 200 mg, 0.536 mmol) in dry THF (10 mL) under argon atmosphere at 0° C. The reaction mixture was stirred at 0° C. for further 30 minutes and then for 16 hours at room temperature. After completion of the reaction, the reaction mixture was quenched with aqueous ammonium chloride. The aqueous layer was extracted with ethyl acetate (3×25 mL). The combined organic layer was dried over anhydrous Na$_2$SO$_4$, concentrated and purified by flash column chromatography (silica gel, hexane and ethyl acetate).

$^1$H NMR (DMSO-$d_6$, 300 MHz): δ ppm 11.59 (br s, 1H), 10.26 (bs, 1H), 8.13 (s, 1H), 7.85 (d, J=7.8 Hz, 2H), 7.64 (s, 1H), 7.60 (d, J=8.4 Hz, 2H), 6.93 (d, J=9.0 Hz, 1H), 3.76 (s, 2H), 3.28 (q, J=7.2 & 7.5 Hz, 2H), 2.99 (t, J=7.2 & 7.2 Hz, 2H), 1.60 (t, J=7.2 & 7.2 Hz, 2H), 1.34 (q, J=7.2 & 7.5 Hz, 2H), 1.10 (t, J=7.2 & 7.5 Hz, 3H), 0.92 (t, J=7.2 & 7.2 Hz, 3H); Mass (ESI): m/z 404 [M+H]$^+$.

Example 41

N-(5-(tert-Butyl)-5-hydroxy-5,6,7,8-tetrahydronaphthalen-2-yl)-2-(4-(ethylsulfonyl)phenyl) acetamide To the stirred solution of 2-(4-(ethylsulfonyl)phenyl)-N-(5-oxo-5,6,7,8-tetrahydronaphthalen-2-yl)acetamide (Example 15, 0.250 g, 0.673 mmol) in dry THF (5 mL) under inert atmosphere, tert-butylmagnesium bromide (5.38 mL, 2.69 mmol) was added at 0° C. and the reaction mixture was stirred for 16 hours at room temperature. The reaction mixture was quenched with NH$_4$Cl solution, extracted with DCM. The organic layer was washed with water and brine, dried over sodium sulphate and the crude product obtained was purified by column chromatography (silica gel, methanol and DCM).

$^1$H NMR (DMSO-$d_6$, 300 MHz): δ ppm 10.13 (s, 1H), 7.84 (d, J=8.0 Hz, 2H), 7.60 (d, J=8.1 Hz, 2H), 7.46 (d, J=8.4 Hz, 1H), 7.30 (d, J=8.4 Hz, 2H), 4.70 (s, 1H), 3.75 (s, 2H), 3.25 (q, J=7.2 Hz, 2H), 1.08 (t, J=7.5 Hz, 3H), 0.83 (s, 9H); Mass (ESI): m/z 412 [M−OH].

Example 42

2-(4-(Ethylsulfonyl)phenyl)-N-(5-hydroxy-5-phenyl-5,6,7,8-tetrahydronaphthalen-2-yl) acetamide The title compound was prepared by the reaction of 2-(4-(ethylsulfonyl)phenyl)-N-(5-oxo-5,6,7,8-tetrahydronaphthalen-2-yl)acetamide (Example 15, 0.250 g, 0.673 mmol) with phenylmagnesium bromide (2.69 mL, 2.69 mmol) as per the process described for the preparation of the compound of example 41.

$^1$H NMR (DMSO-$d_6$, 300 MHz): δ ppm 10.17 (s, 1H), 7.85 (d, J=8.1 Hz, 2H), 7.60 (d, J=8.1 Hz, 2H), 7.41 (s, 1H), 7.26-7.15 (m, 6H), 6.89 (d, J=8.7 Hz, 1H), 5.47 (s, 1H), 4.00 (s, 2H), 3.25 (q, J=7.2 Hz, 2H), 2.75 (m, 2H), 1.98 (m, 3H), 1.57 (m, 1H), 1.08 (t, J=7.5 Hz, 3H); Mass (ESI): m/z 432.4 [M−OH].

Example 43

2-(4-(Ethylsulfonyl)phenyl)-N-(5-hydroxy-5-(4-methoxyphenyl)-5,6,7,8-tetrahydro naphthalen-2-yl) acetamide The title compound was prepared by the reaction of 2-(4-(ethylsulfonyl)phenyl)-N-(5-oxo-5,6,7,8-tetrahydronaphthalen-2-yl)acetamide (Example 15, 1.0 g, 2.69 mmol) with p-methoxyphenylmagnesium bromide (21.54 mL, 10.77 mmol) as per the process described for the preparation of the compound of example 41.

$^1$H NMR (DMSO-$d_6$, 300 MHz): δ ppm 10.16 (s, 1H), 7.85 (d, J=9.0 Hz, 2H), 7.60 (d, J=8.7 Hz, 2H), 7.39 (s, 1H), 7.24 (d, J=8.7 Hz, 1H), 7.09 (d, J=8.7 Hz, 2H), 6.93 (d, J=8.7 Hz, 1H), 6.80 (d, J=8.7 Hz, 2H), 5.37 (s, 1H), 3.76 (s, 2H), 3.69 (s, 3H), 3.25 (q, J=7.2 Hz, 2H), 2.73 (m, 2H), 1.91 (m, 3H), 1.57 (m, 1H), 1.08 (t, J=7.5 Hz, 3H); Mass (ESI): m/z 462.5 [M−OH].

Example 44

2-(4-(Ethylsulfonyl)phenyl)-N-(5-hydroxy-5-vinyl-5,6,7,8-tetrahydronaphthalen-2-yl)acetamide The title compound was prepared by the reaction of 2-(4-(ethylsulfonyl)phenyl)-N-(5-oxo-5,6,7,8-tetrahydronaphthalen-2-yl)acetamide (Example 15, 0.2 g, 0.538 mmol) and allylmagnesium bromide (4.31 mL, 2.15 mmol) as per the process described for the preparation of the compound of example 41.

$^1$H NMR (DMSO-$d_6$, 300 MHz): δ ppm 10.13 (s, 1H), 7.84 (d, J=8.1 Hz, 2H), 7.59 (d, J=8.1 Hz, 2H), 7.42 (d, J=8.1 Hz, 1H), 7.32 (d, J=8.7 Hz, 2H), 5.75-5.63 (m, 1H), 5.00-4.95 (m, 2H), 4.82 (s, 1H), 3.75 (s, 2H), 3.25 (q, J=7.2 Hz, 2H), 2.72 (m, 2H), 2.39 (m, 3H), 1.83-1.62 (m, 1H), 1.08 (t, J=7.5 Hz, 3H).

Example 45

2-(4-(Ethylsulfonamido)phenyl)-N-(4-(1,1,1,3,3,3-hexafluoro-2-hydroxypropan-2-yl) phenyl)acetamide Step 1: N-(4-(1,1,1,3,3,3-Hexafluoro-2-hydroxypropan-2-yl)phenyl)-2-(4-nitrophenyl) acetamide To a solution of 2-(4-aminophenyl)-1,1,1,3,3,3-hexafluoropropan-2-ol (2 g, 7.72 mmol), 2-(4-nitrophenyl)acetic acid (1.538 g, 8.49 mmol) in DMF under inert atmosphere was added HATU (3.52 g, 9.26 mmol), DIEA (2.022 mL, 11.58 mmol) and the reaction mixture was stirred for 24 hours. The reaction mixture was quenched with water, extracted with ethyl acetate. The organic layer was washed with water and brine, dried on sodium sulphate and concentrated to obtain the crude product. The crude product was purified by column chromatography (silica gel, hexane and ethyl acetate).

$^1$H NMR (DMSO-$d_6$, 300 MHz): δ ppm 3.85 (s, 2H), 7.59-7.61 (d, 4H), 7.69-7.72 (d, 2H), 8.18-8.21 (d, 2H), 8.62 (s, 1H), 10.5 (s, 1H); Mass (ESI): m/z 423 [M+H]$^+$.

Step 2: 2-(4-Aminophenyl)-N-(4-(1,1,1,3,3,3-hexafluoro-2-hydroxypropan-2-yl)phenyl) acetamide To a solution of N-(4-(1,1,1,3,3,3-hexafluoro-2-hydroxypropan-2-yl)phenyl)-2-(4-nitro phenyl)acetamide (0.4 g, 0.947 mmol), as obtained in step 1, in ethanol (6 mL):water (4 mL):THF (2 mL) was added iron powder (0.132 g, 2.368 mmol), ammonium chloride (0.127 g, 2.36 mmol) and the reaction mixture was heated to 70° C. for 5-6 hours. The reaction mixture was cooled to room temperature, filtered through celite bed, the filtrate was concentrated and the crude product obtained was purified by column chromatography (silica gel, hexane and ethyl acetate).
$^1$H NMR (DMSO-$d_6$, 300 MHz): δ ppm 3.32-3.42 (s, 2H), 4.93 (s, 2H), 6.50-6.48 (d, J=8.4 Hz, 2H), 6.97-6.74 (d, J=8.4 Hz, 2H), 7.59-7.46 (d, J=8.7 Hz, 2H), 7.71-7.68 (d, J=9.0 Hz, 2H), 8.58 (s, 1H), 10.23 (s, 1H); Mass (ESI): m/z 393 [M+H]$^+$.

Step 3: 2-(4-(Ethylsulfonamido)phenyl)-N-(4-(1,1,1,3,3,3-hexafluoro-2-hydroxypropan-2-yl)phenyl)acetamide To a stirred solution of 2-(4-aminophenyl)-N-(4-(1,1,1,3,3,3-hexafluoro-2-hydroxypropan-2-yl)phenyl)acetamide (0.1 g, 0.255 mmol), as obtained in step 2, in DCM (3 mL) was added ethanesulfonyl chloride (0.029 mL, 0.306 mmol), pyridine (0.103 mL, 1.275 mmol) at 0° C. and the reaction mixture was stirred for 16 hours at room temperature. The reaction mixture was evaporated and the crude product obtained was further purified by column chromatography (silica gel, hexane and ethyl acetate).
$^1$H NMR (DMSO-$d_6$, 300 MHz): δ ppm 1.16-1.19 (t, J=4.5 Hz, J=8.7 Hz, 3H) 3.02-3.07 (q, 2H), 3.60 (s, 2H), 7.15-7.17 (d, J=8.5 Hz, 2H), 7.28-7.27 (d, J=8 Hz, 2H), 7.60-7.27 (d, J=9 Hz, 2H), 7.71-7.70 (d, J=8.5 Hz, 2H), 8.65 (s, 1H), 9.73 (s, 1H), 10.38 (s, 1H); Mass (ESI): m/z 485 [M+H]$^+$.

Example 46

N-(4-(1,1,1,3,3,3-Hexafluoro-2-hydroxypropan-2-yl)phenyl)-2-(4-(4-(trifluoromethyl) phenylsulfonamido)phenyl)acetamide This compound was prepared by the reaction of 2-(4-aminophenyl)-N-(4-(1,1,1,3,3,3-hexafluoro-2-hydroxypropan-2-yl)phenyl)acetamide (0.08 g, 0.209 mmol) with 4-(trifluoro methyl)benzene-1-sulfonyl chloride (0.061 g, 0.251 mmol) using pyridine (0.081 mL, 1.045 mmol) analogous to the process described in step 3 of the preparation of the compound of example 45.
$^1$H NMR (DMSO-$d_6$, 300 MHz): δ ppm 3.56 (s, 2H), 7.04-7.06 (d, J=8 Hz, 2H), 7.21-7.19 (d, J=7.5 Hz, 2H), 7.59-7.57 (d, J=8.5 Hz, 2H), 7.68-7.67 (d, J=8.5 Hz, 2H), 7.95 (s, 4H), 8.61 (s, 1H), 10.33 (s, 1H), 10.49 (s, 1H); Mass (ESI): m/z 601 [M+H]$^+$.

Example 47

2-(4-(Ethylsulfonyl)phenyl)-N-(4-(perfluoropropan-2-yl)phenyl)acetamide

To the stirred solution of 2-(4-(ethylsulfonyl)phenyl)-N-(4-(1,1,1,3,3,3-hexafluoro-2-hydroxypropan-2-yl)phenyl)acetamide (0.063 g, 0.134 mmol) in dry THF (5 mL) was added Deoxo-fluorR (0.5 mL, 1.164 mmol) and reaction mixture was stirred overnight. Completion of reaction was monitored by TLC. Solvent was removed under reduced pressure, quenched with sodium bicarbonate and extracted with ethylacetate. Combined organic layer was washed with water and brine, dried over sodium sulphate. Solvent was removed under reduced pressure, crude residue was purified by column chromatography to afford pure product.
$^1$H NMR (500 MHz, DMSO-d6): δ 10.64 (s, 1H), 7.88-7.83 (m, 4H), 7.63-7.57 (m, 4H), 3.85 (s, 2H), 3.28 (q, J=7.5 Hz, 2H), 1.11 (t, J=7.2 Hz, 3H). Mass (ESI): m/z 472.3 [M+H]$^+$.

Example 48

N-(Cyclopropylmethyl)-2-(4-(ethylsulfonyl)phenyl)-N-(4-(1,1,1,3,3,3-hexafluoro-2-hydroxypropan-2-yl)phenyl)acetamide To a stirred solution of 2-(4-(ethylsulfonyl)phenyl)acetic acid (65 mg, 0.285 mmol) in dichloromethane (2.000 mL) was added DMF (0.01 mL). The reaction mixture was cooled to 0° C. followed by addition of oxalyl chloride (37.4 µL, 0.427 mmol) and stirred for 1 hour. TLC was monitored. The reaction mixture was evaporated and later dissolved in DCM (2 mL). 2-(4-((cyclopropylmethyl)amino)phenyl)-1,1,1,3,3,3-hexafluoropropan-2-ol (89 mg, 0.285 mmol) was taken in another flask and dissolved in dichloromethane (2.000 mL). The mixture was cooled to 0° C. and TEA (119 µL, 0.854 mmol) was added. Further, previously synthesized acid chloride was added drop-wise and stirred. TLC was monitored and work up was done by quenching reaction in water and extracted with DCM. The DCM layer was separated and dried over Sodium sulphate and latter evaporated to give crude mass, The crude mass was purified by column chromatography to give required compound.
$^1$H NMR (DMSO-$d_6$, 300 MHz) δ ppm: 8.87 (s, 1H), 7.80-7.72 (m, 4H), 7.47 (d, J=8.4 Hz, 2H), 7.30-7.28 (m, 2H), 3.56 (d, J=6.3 Hz, 4H), 3.26 (q, J=7.2 Hz, 2H), 1.07 (t, J=7.2 Hz, 3H), 0.90-0.87 (m, 1H), 0.38 (d, J=6.9 Hz, 2H), 0.03 (d, J=4.5 Hz, 2H); Mass (ESI): m/z 524.1 [M+H]$^+$.

Example 49

2-(4-(Ethylsulfonimidoyl)phenyl)-N-(3-(1,1,1,3,3,3-hexafluoro-2-hydroxypropan-2-yl)phenyl)acetamide Step 1:
To the stirred solution of 2-(4-(ethylsulfinyl)phenyl)acetic acid (0.120 g, 0.565 mmol) in dry DCM (10 mL), was added N1-((ethylimino)methylene)-N3,N3-dimethylpropane-1,3-diamine, HCl salt (0.108 g, 0.565 mmol), 2-(3-aminophenyl)-1,1,1,3,3,3-hexafluoropropan-2-ol (0.147 g, 0.565 mmol) and 1H-benzo[d][1,2,3]triazol-1-ol salt (0.087 g, 0.565 mmol) under inert atmosphere. The reaction continued overnight. TLC showed completion of the reaction. Solvent was evaporated and crude residue was used further.
Step 2:
To 110 mg of 2-(4-(ethylsulfinyl)phenyl)-N-(3-(1,1,1,3,3,3-hexafluoro-2-hydroxypropan-2-yl)phenyl)acetamide, was added chloroform and cooled to 0-5° C. Sodium azide (2.0 eqiv.) was added followed by addition of 2.0 eqiv. of sulphuric acid dropwise. The reaction mixture was stirred overnight. The chloroform layer was decanted. The reaction mass was neutralised with sodium bicarbonate and extracted with DCM, dried over sodium sulphate and solvent was removed under reduced pressure. Crude residue was further purified on column to afford pure desired product.

¹H NMR (300 MHz, DMSO-d6): δ 1.06 (t, 3H, J=6.0 Hz), 3.12 (q, 2H, J=7.2 Hz), 3.78 (s, 2H), 4.1 (s, 1H), 7.36-7.56 (m, 2H), 7.56 (d, 2H, J=9 Hz), 7.79 (d, 1H, J=9 Hz), 7.85 (d, 2H, J=9 Hz), 8.03 (s, 1H), 10.46 (s, 1H); Mass (ESI): m/z 469.1 [M+H]⁺.

The compounds of examples 50-81 were prepared analogous to the process described for the preparation of the compound of example 49.

Example 50

N-(4-(2-Cyano-1,1,1,3,3,3-hexafluoropropan-2-yl) phenyl)-2-(4-(ethylsulfonimidoyl) phenyl) acetamide ¹H NMR (300 MHz, DMSO-d6): δ 1.05 (t, 3H, J=6.0 Hz), 3.12 (q, 2H, J=9.0 Hz), 3.82 (s, 2H), 4.14 (s, 1H), 7.56 ((d, 2H, J=9 Hz), 7.74 (d, 2H, J=9 Hz), 7.82-7.90 (m, 4H), 10.68 (s, 1H); Mass (ESI): m/z 478.1 [M+H]⁺.

Example 51

2-(4-(Ethylsulfonimidoyl)phenyl)-N-(4-(1,1,1,3,3,3-hexafluoro-2-hydroxypropan-2-yl)-2-methylphenyl) acetamide ¹H NMR (300 MHz, DMSO-d6): 9.70 (s, 1H), 8.65 (s, 1H), 7.85 (d, J=9 Hz, 2H), 7.5-7.46 (m, 5H), 4.16 (s, 1H), 3.84 (s, 2H), 3.12 (m, 2H) 2.25 (s, 3H), 1.05 (t, J=7.2 HZ, 3H); Mass (ESI): m/z 483.1 [M+H]⁺.

Example 52

N-(4-(2-Ethoxy-1,1,1,3,3,3-hexafluoropropan-2-yl) phenyl)-2-(4(ethylsulfonimidoyl) phenyl)acetamide ¹H NMR (300 MHz, DMSO-d6): δ 1.07 (t, 3H, J=6.0 Hz), 1.29 (t, 3H, J=6.0 Hz), 3.11 (q, 2H, J=6.0 Hz), 3.57 (q, 2H, J=6.0 Hz), 3.80 (s, 2H), 4.14 (s, 1H), 7.48-7.56 (m, 4H), 7.77-7.85 (m, 4H), 10.55 (s, 1H); Mass (ESI): m/z 497.1 [M+H]⁺.

Example 53

N-(4-(2-Ethoxy-1,1,1,3,3,3-hexafluoropropan-2-yl) phenyl)-2-(4-(ethylsulfonyl)phenyl) acetamide ¹H NMR (DMSO-d₆, 500 MHz) δ ppm: 10.56 (s, 1H), 7.85 (d, J=10.0 Hz, 2H), 7.80 (d, J=10.0 Hz, 2H), 7.62 (d, J=10.0 Hz, 2H), 7.51 (d, J=10.0 Hz, 2H), 3.84 (s, 2H), 3.57 (q, J=10 Hz, 2H), 3.28 (q, J=10.0 Hz, 2H), 1.28 (t, J=10 Hz, 3H), 1.09 1.28 (t, J=10 Hz, 3H); Mass (ESI): m/z 499.7 [M+2H]⁺.

Example 54

2-(4-(Ethylsulfonyl)phenyl)-N-(4-(1,1,1,3,3,3-hexafluoro-2-isopropoxypropan-2-yl)phenyl) acetamide ¹H NMR (DMSO-d₆, 300 MHz) δ ppm: 10.55 (s, 1H), 7.85 (d, J=9.0 Hz, 2H), 7.78 (d, J=9.0 Hz, 2H), 7.61-7.56 (m, 4H), 3.90-3.88 (m, 1H), 3.82 (s, 2H), 3.25 (q, J=6 Hz, 2H), 1.21 (d, J=6.0 Hz, 6H), 1.08 (t, J=6.0 Hz, 3H); Mass (ESI): m/z 512.9 [M+H]⁺.

Example 55

2-(4-(Ethylsulfonyl)phenyl)-N-(4-(1,1,1,3,3,3-hexafluoro-2-propoxypropan-2-yl)phenyl) acetamide ¹H NMR (DMSO-d₆, 300 MHz) δ ppm: 10.57 (s, 1H), 7.86 (d, J=8.5 Hz, 2H), 7.80 (d, J=6 Hz 2H), 7.60 (d, J=8.5 Hz, 2H), 7.51 (d, J=8.5 Hz, 2H), 3.84 (s, 2H), 3.46 (q, J=6.5 Hz, 2H), 3.30 (q, J=7.0 Hz, 2H), 1.70 (q, J=5 Hz, 2H), 1.10 (t, J=7.0 Hz, 3H), 0.92 (t, J=7.5 Hz, 3H); Mass (ESI): m/z 512.1 [M+H]⁺.

Example 56

N-(4-(2-(Cyclopentylmethoxy)-1,1,1,3,3,3-hexafluoropropan-2-yl)phenyl)-2-(4-(ethyl sulfonyl)phenyl) acetamide ¹H NMR (DMSO-d₆, 300 MHz) δ ppm: 10.51 (s, 1H), 7.86 (d, J=8.0 Hz, 2H), 7.79 (d, J=8.5 Hz, 2H), 7.62 (d, J=8.0 Hz, 2H), 7.51 (d, J=8.5 Hz, 2H), 3.83 (s, 2H), 3.38 (q, J=7.0 Hz, 2H), 3.27 (q, J=7.5 Hz, 2H), 2.26-2.21 (m, 1H), 1.27-1.23 (m, 2H), 1.09 (t, J=10 Hz, 3H), Mass (ESI): m/z 552.4 [M+H]⁺.

Example 57

2-(4-(Ethylsulfonyl)phenyl)-N-(4-(1,1,1,3,3,3-hexafluoro-2-(prop-2-yn-1-yloxy)propan-2-yl)phenyl)acetamide ¹H NMR (DMSO-d₆, 300 MHz) δ ppm: 10.60 (s, 1H), 7.86-7.79 (m, 4H), 7.62 (d, J=6.0 Hz, 2H), 7.53 (d, J=8.1 Hz, 2H), 4.27 (s, 2H), 3.84 (s, 2H), 3.73 (s, 1H), 3.26 (q, J=7.2 Hz, 2H), 1.09 (t, J=7.5 Hz, 3H), Mass (ESI): m/z 508.2 [M+H]⁺,

Example 58

A) 2-(4-(Ethylsulfonyl)phenyl)-N-(4-(1,1,1,3,3,3-hexafluoro-2-(pyridin-2-ylmethoxy) propan-2-yl) phenyl)acetamide 1H NMR (DMSO-d6, 500 MHz) δ ppm: 10.59 (s, 1H), 8.61 (d, J=4.5 Hz, 1H), 7.91-7.86 (m, 1H), 7.84 (d, J=8.0 Hz, 2H), 7.82 (d, J=9.0 Hz, 2H), 7.66 (d, J=8.5 Hz, 2H), 7.62 (d, J=8.0 Hz, 2H), 7.58 (d, J=7.5 Hz, 1H), 7.57-7.42 (m, 1H), 4.65 (s, 2H), 3.84 (s, 2H), 3.27 (q, J=7.0 Hz, 2H), 1.09 (t, J=7.5 Hz, 3H); Mass (ESI): m/z 561.2 [M+H]⁺.

B) 2-(4-(Ethylsulfonyl)phenyl)-N-(4-(1,1,1,3,3,3-hexafluoro-2-(pyridin-2-ylmethoxy) propan-2-yl) phenyl)acetamide hydrochloride To the stirred solution of 2-(4-(ethylsulfonyl)phenyl)-N-(4-(1,1,1,3,3,3-hexafluoro-2-(pyridin-2-ylmethoxy)propan-2-yl)phenyl)acetamide (0.030 g, 0.054 mmol) in ethyl acetate (5 mL) under inert atmosphere, was added ethyl acetate.HCl (15 mL). The reaction mixture had turned turbid. To it, was added one drop of methanol to get a clear solution. The reaction mixture was stirred continuously for few more hours until the precipitation was observed. The stirring was continued overnight. The ethyl acetate layer was decanted and washed with pet ether twice and then concentrated under vacuum to afford desired compound.

¹H NMR (DMSO-d₆, 300 MHz) δ ppm: 10.66 (s, 1H), 8.64 (d, J=4.2 Hz, 1H), 7.99-7.96 (m, 1H), 7.83 (t, J=8.1 Hz, 5H), 7.62 (t, J=8.1 Hz, 5H), 7.50-7.48 (m, 1H), 4.68 (s, 2H), 3.84 (s, 2H), 3.28 (q, J=7.5 Hz, 2H), 1.09 (t, J=7.2 Hz, 3H); Mass (ESI): m/z 598.1 [M+H]$^+$.

Example 59

2-(4-(Ethylsulfonyl)phenyl)-N-(4-(1,1,1,3,3,3-hexafluoro-2-methoxypropan-D$_3$-2-yl)phenyl) acetamide $^1$H NMR (DMSO-d$_6$, 300 MHz) δ ppm: 10.58 (s, 1H), 7.86 (d, J=7.8 Hz, 2H), 7.81 (d, J=8.7 Hz, 2H), 7.62 (d, J=7.8 Hz, 2H), 7.52 (d, J=7.8 Hz, 2H), 3.84 (s, 2H), 3.26 (q, J=7.2 Hz, 2H), 1.09 (t, J=7.5 Hz, 3H); Mass (ESI): m/z 487.1 [M+H]$^+$.

Example 60

2-(4-(Ethylsulfonyl)phenyl)-N-(4-(1,1,1,3,3,3-hexafluoro-2-(2-methoxyethoxy)propan-2-yl)phenyl) acetamide $^1$H NMR (DMSO-d$_6$, 300 MHz) δ ppm: 10.56 (s, 1H), 7.85 (d, J=8.1 Hz, 2H), 7.77 (d, J=9.0 Hz, 2H), 7.61-7.54 (m, 4H), 3.82 (s, 2H), 3.62-3.60 (m, 4H), 3.29 (s, 3H), 3.26 (q, J=7.2 Hz, 2H), 1.08 (t, J=7.5 Hz, 3H); Mass (ESI): m/z 528.1 [M+H]$^+$.

Example 61

N-(4-(2-(Cyclopropylmethoxy)-1,1,1,3,3,3-hexafluoropropan-2-yl)phenyl)-2-(4-(ethylsulfonyl)phenyl) acetamide $^1$H NMR (DMSO-d$_6$, 300 MHz) δ ppm: 10.57 (s, 1H), 7.85 (d, J=8.1 Hz, 2H), 7.78 (d, J=8.7 Hz, 2H), 7.61 (d, J=8.4 Hz, 2H), 7.52 (d, J=8.4 Hz, 2H), 3.82 (s, 2H), 3.33-3.24 (m, 4H), 1.40-1.10 (m, 1H), 1.08 (t, J=7.5 Hz, 3H), 0.57 (d, J=6.9 Hz, 2H), 0.26 (d, J=5.1 Hz, 2H); Mass (ESI): m/z 524.1 [M+H]$^+$.

Example 62

2-(4-(Ethylsulfonyl)phenyl)-N-(4-(1,1,1,3,3,3-hexafluoro-2-isobutoxypropan-2-yl)phenyl) acetamide $^1$H NMR (DMSO-d$_6$, 500 MHz) δ ppm: 10.57 (s, 1H), 7.86 (d, J=8.0 Hz, 2H), 7.79 (d, J=8.5 Hz, 2H), 7.62 (d, J=8.0 Hz, 2H), 7.50 (d, J=8.5 Hz, 2H), 4.04 (s, 2H), 3.29-3.25 (m, 4H), 1.99-1.95 (m, 1H), 1.08 (t, J=7.0 Hz, 3H), 0.57 (d, J=3.54 Hz, 6H); Mass (ESI): m/z 526.1 [M+H]$^+$.

Example 63

Methyl 2-((2-(4-(2-(4-(ethylsulfonyl)phenyl)acetamido)phenyl)-1,1,1,3,3,3-hexafluoro propan-2-yl) oxy)acetate $^1$H NMR (DMSO-d$_6$, 300 MHz) δ ppm: 10.60 (s, 1H), 7.86 (d, J=8.1 Hz, 2H), 7.80 (d, J=8.7 Hz, 2H), 7.62 (d, J=8.1 Hz, 2H), 7.55 (d, J=8.4 Hz, 2H), 4.22 (s, 2H), 3.83 (s, 2H), 3.70 (s, 3H 1.08 (t, J=7.2 Hz, 3H); Mass (ESI): m/z 542.1 [M+H]$^+$.

Example 64

N-(4-(2-(Cyclobutylmethoxy)-1,1,1,3,3,3-hexafluoropropan-2-yl)phenyl)-2-(4-(ethylsulfonyl) phenyl) acetamide $^1$H NMR (DMSO-d$_6$, 500 MHz) δ ppm: 10.58 (s, 1H), 7.86 (d, J=8.0 Hz, 2H), 7.80 (d, J=8.5 Hz, 2H), 7.62 (d, J=8.5 Hz, 2H), 7.50 (d, J=8.5 Hz, 2H), 3.84 (s, 2H), 3.48 (d, J=6.5 Hz, 2H), 3.27 (d, J=6.5 Hz, 2H), 2.66-2.64 (m, 1H), 2.05-2.03 (m, 2H), 1.87-1.74 (m, 3H), 1.08 (t, J=7.5 Hz, 3H); Mass (ESI): m/z 538.1 [M+H]$^+$.

Example 65

2-(4-(Ethylsulfonyl)phenyl)-N-(4-(1,1,1,3,3,3-hexafluoro-2-(1H-pyrazol-1-yl)propan-2-yl)phenyl) acetamide $^1$H NMR (DMSO-d$_6$, 500 MHz) δ ppm: 10.61 (s, 1H), 7.86 (d, J=8.0 Hz, 2H), 7.83 (s, 1H), 7.78 (d, J=8.5 Hz, 2H), 7.71 (s, 1H), 7.62 (d, J=8.0 Hz, 2H), 7.33 (d, J=8.5 Hz, 2H), 6.54 (s, 1H), 3.84 (s, 2H), 3.27 (q, J=7.5 Hz, 2H), 1.08 (t, J=7.2 Hz, 3H); Mass (ESI): m/z 520.1 [M+H]$^+$.

Example 66

N-(4-(1,1,1,3,3,3-Hexafluoro-2-hydroxypropan-2-yl) phenyl)-2-(4-(methylsulfonyl)phenyl) acetamide $^1$H NMR (DMSO-d$_6$, 300 MHz) δ ppm: 10.48 (s, 1H), 8.62 (s, 1H), 7.90 (d, J=8.1 Hz, 2H), 7.73 (d, J=9.0 Hz, 2H), 7.61 (d, J=8.4 Hz, 4H), 3.82 (s, 2H) 3.20 (s, 3H); Mass (ESI): m/z 456.0 [M+H]$^+$.

Example 67

2-(4-(N,N-Dimethylsulfamoyl)phenyl)-N-(4-(1,1,1,3,3,3-hexafluoro-2-(pyridin-2-ylmethoxy)propan-2-yl)phenyl)acetamide $^1$H NMR (DMSO-d$_6$, 300 MHz) δ ppm: 10.61 (s, 1H), 8.61 (d, J=4.5 Hz, 1H), 7.93-7.88 (m, 1H), 7.83 (d, J=8.7 Hz, 2H), 7.73 (d, J=8.1 Hz, 2H), 7.66-7.56 (m, 5H), 7.43-7.39 (m, 1H), 4.46 (s, 2H), 3.83 (s, 2H), 2.69 (s, 6H); Mass (ESI): m/z 576.1 [M+H]$^+$.

Example 68

N-Ethyl-2-(4-(ethylsulfonyl)phenyl)-N-(4-(1,1,1,3,3,3-hexafluoro-3-hexa 2-hydroxypropan-2-yl)phenyl) acetamide $^1$H NMR (DMSO-d$_6$, 300 MHz) δ ppm: 8.90 (s, 1H), 7.74-7.72 (m, 4H), 7.47 (d, J=8.1 Hz, 2H), 7.26 (br s, 2H), 7.50-7.48 (m, 1H), 3.73-3.68 (m, 2H), 4.60-3.58 (m, 2H), 3.26 (q, J=7.5 Hz, 2H), 1.10-1.00 (m, 6H); Mass (ESI): m/z 498.1 [M+H]$^+$.

Example 69

2-(4-(Ethylsulfonyl)phenyl)-N-(4-(1,1,1,3,3,3-hexafluoro-2-hydroxypropan-2-yl)phenyl)-N-isopropylacetamide $^1$H NMR (DMSO-d$_6$, 300 MHz) δ ppm: 8.90 (s, 1H), 7.76-7.70 (m, 4H), 7.40 (d, J=8.1 Hz, 2H), 7.24 (d, J=7.8 Hz, 2H), 4.90-4.81 (m, 1H), 3.36 (s, 2H), 3.26 (q, J=7.2 Hz, 2H), 1.07 (t, J=7.5 Hz, 3H), 1.01 (d, J=6.6 Hz, 6H); Mass (ESI): m/z 512.1 [M+H]$^+$.

Example 70

2-(4-(N,N-Dimethylsulfamoyl)phenyl)-N-ethyl-N-(4-(1,1,1,3,3,3-hexafluoro-2-hydroxypropan-2-yl)phenyl)acetamide $^1$H NMR (DMSO-d$_6$, 300 MHz) δ ppm: 8.88 (s, 1H), 7.74 (d, J=8.4 Hz, 2H), 7.59 (d, J=7.5 Hz, 2H), 7.54-7.50 (m, 1H), 7.46 (d, J=8.4 Hz, 2H), 7.30-7.24 (m, 1H), 3.71 (d, J=6.9 Hz, 2H), 3.60-3.53 (m, 2H), 2.73 (s, 6H), 1.02 (t, J=7.2 Hz, 3H); Mass (ESI): m/z 513.1 [M+H]$^+$.

Example 71

2-(4-(Ethylsulfonyl)phenyl)-N-isobutyl-N-(4-(perfluoropropan-2-yl)phenyl)acetamide $^1$H NMR (DMSO-d$_6$, 300 MHz) δ ppm: 7.73-7.71 (m, 4H), 7.62 (d, J=8.4 Hz, 2H), 7.30-7.28 (m, 2H), 3.63-3.57 (m, 4H), 3.26 (q, J=7.2 Hz, 2H), 1.63-1.59 (m, 1H), 1.07 (t, J=7.2 Hz, 3H), 0.85 (d, J=6.9 Hz, 6H); Mass (ESI): m/z 528.1 [M+H]$^+$.

Example 72

2-(4-(Ethylsulfonyl)phenyl)-N-(4-(1,1,1,3,3,3-hexafluoropropan-2-yl)phenyl)acetamide $^1$H NMR (DMSO-d$_6$, 300 MHz) δ ppm: 8.16 (br s, 1H), 7.84 (d, J=8.1 Hz, 2H), 7.60 (d, J=8.1 Hz, 3H), 7.40 (d, J=8.1 Hz, 2H), 6.76 (d, J=5.4 Hz, 1H), 5.10-5.06 (m, 1H), 3.79 (s, 2H), 3.27 (q, J=7.2 Hz, 2H), 1.07 (t, J=7.5 Hz, 3H); Mass (ESI): m/z 454.1 [M+H]$^+$.

Example 73

Methyl 2-(4-(2-(4-(ethylsulfonyl)phenyl)acetamido)phenyl)-3,3,3-trifluoro-2-hydroxypropanoate $^1$H NMR (DMSO-d$_6$, 300 MHz) δ ppm: 10.43 (s, 1H), 7.85 (d, J=8.7 Hz, 3H), 7.66 (d, J=8.7 Hz, 2H), 7.61 (d, J=8.1 Hz, 2H), 7.48 (d, J=8.1 Hz, 2H), 3.81 (s, 2H), 3.78 (s, 3H), 3.26 (q, J=7.2 Hz, 2H), 1.07 (t, J=7.5 Hz, 3H); Mass (ESI): m/z 460.1 [M+H]$^+$.

Example 74

N-(4-(2-Amino-1,1,1,3,3,3-hexafluoropropan-2-yl)phenyl)-2-(4-(ethylsulfonyl)phenyl)acetamide $^1$H NMR (DMSO-d$_6$, 300 MHz) δ ppm: 10.47 (s, 1H), 7.86 (d, J=8.1 Hz, 2H), 7.67 (s, 4H), 7.62 (d, J=8.1 Hz, 2H), 3.82 (s, 2H), 3.37 (s, 2H), 3.26 (q, J=7.2 Hz, 2H), 1.07 (t, J=7.5 Hz, 3H); Mass (ESI): m/z 469.1 [M+H]$^+$.

Example 75

2-(4-(Ethylsulfonyl)phenyl)-N-(4-(1,1,1,3,3,3-hexafluoro-2-(1H-imidazol-1-yl)propan-2-yl)phenyl)acetamide $^1$H NMR (DMSO-d$_6$, 300 MHz) δ ppm: 10.64 (s, 1H), 7.86-7.78 (m, 5H), 7.62 (d, J=8.4 Hz, 2H), 7.39 (d, J=8.1 Hz, 2H), 7.23 (s, 1H), 7.15 (s, 1H), 3.84 (s, 2H), 3.26 (q, J=7.2 Hz, 2H), 1.07 (t, J=7.5 Hz, 3H); Mass (ESI): m/z 520.1 [M+H]$^+$.

Example 76

2-(4-(Ethylsulfonyl)phenyl)-N-(4-(1,1,1,3,3,3-hexafluoro-2-hydroxypropan-2-yl)cyclohexyl)acetamide $^1$H NMR (DMSO-d$_6$, 300 MHz) δ ppm: 8.12 (d, J=7.8 Hz, 1H), 7.82 (d, J=7.8 Hz, 2H), 7.66 (s, 1H), 7.52 (d, J=8.1 Hz, 2H), 3.51 (s, 2H), 3.50-3.46 (m, 1H), 3.28 (q, J=7.2 Hz, 2H), 1.97-1.88 (m, 5H), 1.31-1.16 (m, 4H), 1.09 (t, J=7.5 Hz, 3H); Mass (ESI): m/z 476.2 [M+H]$^+$.

Example 77

2-(4-(Ethylsulfonyl)phenyl)-N-(4-(1,1,1,3,3,3-hexafluoro-2-(1H-tetrazol-5-yl)propan-2-yl)phenyl)acetamide $^1$H NMR (DMSO-d$_6$, 300 MHz) δ ppm: 10.45 (s, 1H), 7.85 (d, J=8.1 Hz, 3H), 7.61 (d, J=7.8 Hz, 4H), 7.07 (d, J=8.4 Hz, 2H), 3.81 (s, 2H), 3.28 (q, J=7.2 Hz, 2H), 1.09 (t, J=7.5 Hz, 3H); Mass (ESI): m/z 522.1 [M+H]$^+$.

Example 78

2-(4-(Ethylsulfonyl)phenyl)-N-(4-(1,1,1,3,3,3-hexafluoro-2-(2-morpholinoethoxy)propan-2-yl)phenyl)acetamide $^1$H NMR (DMSO-d$_6$, 300 MHz) δ ppm: 10.57 (s, 1H), 7.86 (d, J=4.8 Hz, 2H), 7.79 (d, J=5.4 Hz, 2H), 7.64-7.60 (m, 4H), 3.84 (s, 2H), 3.70-3.80 (m, 6H), 3.28 (q, J=7.2 Hz, 2H), 2.70-2.63 (m, 2H), 2.39-2.41 (m, 4H), 1.09 (t, J=7.5 Hz, 3H); Mass (ESI): m/z 583.2 [M+H]$^+$.

Example 79

2-(1,1-Dioxidothiochroman-6-yl)-N-(4-(1,1,1,3,3,3-hexafluoro-2-hydroxypropan-2-yl)phenyl)acetamide $^1$H NMR (DMSO-d$_6$, 300 MHz) δ ppm: 10.45 (s, 1H), 8.62 (s, 1H), 7.75 (s, 1H), 7.72 (d, J=9.3 Hz, 2H), 7.61 (d, J=8.4 Hz, 2H), 7.41 (d, J=8.4 Hz, 1H), 7.30 (s, 1H), 3.73 (s, 2H), 3.50-3.46 (m, 2H), 3.01 (m, 2H), 3.30 (m, 2H); Mass (ESI): m/z 482.1 [M+H]$^+$.

Example 80

N-(4-(1,1,1,3,3,3-Hexafluoro-2-hydroxypropan-2-yl)phenyl)-2-(4-(oxetan-3-ylsulfonyl)phenyl)acetamide $^1$H NMR (DMSO-d$_6$, 300 MHz) δ ppm: 10.50 (s, 1H), 8.63 (s, 1H), 7.89 (d, J=8.4 Hz, 2H), 7.72 (d, J=9.3 Hz, 2H), 7.63-7.58 (m, 4H), 4.89-4.68 (m, 5H), 3.82 (s, 2H); Mass (ESI): m/z 498.1 [M+H]$^+$.

Example 81

N-(4-(Ethylsulfonyl)benzyl)-4-(1,1,1,3,3,3-hexafluoro-2-hydroxypropan-2-yl)benzamide $^1$H NMR (DMSO-d$_6$, 300 MHz) δ ppm: 9.31 (s, 1H), 8.93 (s, 1H), 8.04 (d, J=8.4 Hz, 2H), 7.86 (d, J=6.3 Hz, 2H), 7.83 (d, J=8.7 Hz, 2H), 7.60 (d, J=8.1 Hz, 2H), 4.61 (d, J=5.4 Hz, 2H), 3.28 (q, J=8.4 Hz, 2H), 1.09 (t, J=7.5 Hz, 3H); Mass (ESI): m/z 470.1 [M+H]$^+$.

The compounds of examples 82-88 were prepared analogous to the process described below:

Step 1:

To the stirred solution of 2-(4-(ethylsulfonyl) phenyl)-N-(4-(1,1,1,3,3,3-hexafluoro-2-hydroxypropan-2-yl)phenyl) acetamide (1 equiv.) in dry THF, was added methanesulfonyl chloride (1 equiv.) followed by triethyl amine (2 equiv.) at 0° C. The resulting reaction mixture was stirred for another 3-4 hours. Completion of reaction was monitored by TLC and solvent was removed under vacuum. The residue was diluted with water and extracted with ethylacetate several times. The combined organic layer was washed with brine dried over anhydrous Na$_2$SO$_4$ and solvent was evaporated under vacuum. Crude residue was used without further purification.

Step 2:

To the stirred solution of 2-(4-(2-(4-(ethylsulfonyl)phenyl)acetamido)phenyl)-1,1,1,3,3,3-hexafluoropropan-2-yl methanesulfonate (0.100 g, 0.183 mmol) in acetonitrile (dry) under inert atmosphere, was added potassium carbonate (0.050 g, 0.365 mmol), followed by respective nucleophiles (0.183 mmol). The reaction mixture was then heated to reflux for 3 hours. Completion of the reaction was monitored by TLC. Excess solvent was removed and diluted with DCM. The organic layer was washed with water and brine and purified by column chromatography to afford pure product.

Example 82

2-(4-(Ethylsulfonyl)phenyl)-N-(4-(1,1,1,3,3,3-hexafluoro-2-(oxetan-3-yloxy)propan-2-yl) phenyl) acetamide $^1$H NMR (DMSO-d$_6$, 300 MHz) δ ppm: 10.59 (s, 1H), 7.86 (d, J=8.0 Hz, 2H), 7.80 (d, J=8.7 Hz, 2H), 7.62 (d, J=8.4 Hz, 2H), 7.41 (d, J=8.7 Hz, 2H), 4.66-4-57 (m, 4H), 3.83 (s, 2H), 3.29 (q, J=7.2 Hz, 2H), 1.08 (t, J=7.2 Hz, 3H); Mass (ESI): m/z 526.1 [M+H]$^+$.

Example 83

2-(4-(Ethylsulfonyl)phenyl)-N-(4-(1,1,1,3,3,3-hexafluoro-2-morpholinopropan-2-yl)phenyl) acetamide $^1$H NMR (DMSO-d$_6$, 300 MHz) δ ppm: 10.50 (s, 1H), 7.86 (d, J=8.1 Hz, 2H), 7.74 (d, J=9.0 Hz, 2H), 7.60-7.59 (m, 4H), 3.82 (s, 2H), 3.60-3.64 (m, 4H), 3.28 (q, J=7.2 Hz, 2H), 2.80-2.75 (m, 4H), 1.09 (t, J=7.5 Hz, 3H); Mass (ESI): m/z 539.1 [M+H]$^+$.

Example 84

2-(4-(Ethylsulfonyl)phenyl)-N-(4-(1,1,1,3,3,3-hexafluoro-2-(3-methylpiperidin-1-yl)propan-2-yl) phenyl)acetamide $^1$H NMR (DMSO-d$_6$, 300 MHz) δ ppm: 10.50 (s, 1H), 7.86 (d, J=8.1 Hz, 2H), 7.73 (d, J=9.0 Hz, 2H), 7.62 (d, J=7.8 Hz, 4H), 3.82 (s, 2H), 3.28 (q, J=7.5 Hz, 2H), 2.70-2.83 (m, 2H), 2.20-2.10 (m, 1H), 1.80-1.58 (m, 5H), 1.08 (t, J=7.5 Hz, 3H), 0.79 (d, J=6.3 Hz, 4H); Mass (ESI): m/z 551.2 [M+H]$^+$.

Example 85

2-(4-(Ethylsulfonyl)phenyl)-N-(4-(1,1,1,3,3,3-hexafluoro-2-(4-(4-methoxyphenyl) piperazin-1-yl) propan-2-yl)phenyl)acetamide $^1$H NMR (DMSO-d$_6$, 300 MHz) δ ppm: 10.51 (s, 1H), 7.86 (d, J=8.1 Hz, 2H), 7.75 (d, J=9.0 Hz, 2H), 7.67-7.59 (m, 4H), 6.91 (d, J=9.0 Hz, 2H), 6.83 (d, J=8.1 Hz, 2H), 3.82 (s, 2H), 3.68 (s, 3H), 3.26 (q, J=7.2 Hz, 2H), 3.2-3.07 (m, 4H), 3.04-2.92 (m, 4H), 1.09 (t, J=4.5 Hz, 3H); Mass (ESI): m/z 644.2 [M+H]$^+$.

Example 86

2-(4-(Ethylsulfonyl)phenyl)-N-(4-(1,1,1,3,3,3-hexafluoro-2-(4-(4-fluorophenyl)piperazin-1-yl)propan-2-yl)phenyl)acetamide $^1$H NMR (DMSO-d$_6$, 300 MHz) δ ppm: 10.52 (s, 1H), 7.86 (d, J=8.1 Hz, 2H), 7.75 (d, J=8.7 Hz, 2H), 7.67-7.60 (m, 4H), 7.09-7.06 (m, 2H), 6.97-6.93 (m, 2H), 3.82 (s, 2H), 3.26 (q, J=7.5 Hz, 2H), 3.2-3.1 (m, 4H), 3.04-2.91 (m, 4H), 1.09 (t, J=7.2 Hz, 3H); Mass (ESI): m/z 632.2 [M+H]$^+$.

Example 87

N-(4-(2-Cyano-1,1,1,3,3,3-hexafluoropropan-2-yl) phenyl)-2-(4-(ethylsulfonyl)phenyl) acetamide $^1$H NMR (DMSO-d$_6$, 300 MHz) δ ppm: 10.70 (s, 1H), 7.90-7.87 (m, 4H), 7.74 (d, J=8.4 Hz, 2H), 7.63 (d, J=7.8 Hz, 2H), 3.86 (s, 2H), 3.26 (q, J=7.5 Hz, 2H), 1.09 (t, J=7.2 Hz, 3H); Mass (ESI): m/z 479.0 [M+H]$^+$.

Example 88

2-(4-(Ethylsulfonyl)phenyl)-N-(4-(1,1,1,3,3,3-hexafluoro-2-methylpropan-2-yl)phenyl) acetamide $^1$H NMR (DMSO-d$_6$, 300 MHz) δ ppm: 10.73 (s, 1H), 7.91 (d, J=9.0 Hz, 2H), 7.86 (d, J=8.1 Hz, 2H), 7.75 (d, J=8.7 Hz, 2H), 7.63 (d, J=8.1 Hz, 2H), 3.86 (s, 2H), 3.26 (q, J=7.5 Hz, 2H), 2.09 (s, 3H), 1.09 (t, J=7.2 Hz, 3H); Mass (ESI): m/z 468.1 [M+H]$^+$.

Example 89

2-(4-(Ethylsulfonyl)phenyl)-N-(4-(2,2,2-trifluoro-1-hydroxy-1-phenylethyl)phenyl) acetamide Step-1:

To a stirred solution of 4-nitrobenzoyl chloride (1.0 g, 5.39 mmol) and phenylboronic acid in THF (0.657 g, 5.39 mmol) in toluene, was added K$_2$CO$_3$ (1.862 g, 13.47 mmol) followed by Pd(Ph$_3$P)$_4$ (0.016 g, 0.054 mmol). The reaction mixture was heated to reflux for 16 hours and brought to room temperature. The solvent was evaporated under pressure and crude compound was purified on column chromatography.

Step-2:

To a stirred solution of (4-nitrophenyl)(phenyl)methanone (1.0 g, 4.40 mmol) and trimethyl(trifluoromethyl)silane (0.782 mL, 5.28 mmol) in DMF was added $K_2CO_3$ (0.061 g, 0.440 mmol) and stirred at RT for 3 hours the reaction mixture was quenched with water, solvent was removed under vacuum. The residue was diluted with water and extracted with ethylacetate. Combined organic layer was dried over $Na_2SO_4$ and solvent was evaporated. Crude product was further purified on column chromatography.

Step-3:

To a stirred solution of trimethyl(2,2,2-trifluoro-1-(4-nitrophenyl)-1-phenylethoxy)silane (1.0 g, 2.71 mmol) in ethanol (10 mL) and water (5 mL), was added ammonium chloride 0.3 g and Iron 1 g, and the reaction mixture was refluxed for 2 hours. It was then filtered through celite and solvent was evaporated. Crude residue was further purified on column chromatography.

Step-4:

To a stirred solution of 4-(2,2,2-trifluoro-1-phenyl-1-((trimethylsilyl)oxy)ethyl)aniline (200 mg, 0.589 mmol) and 2-(4-(ethylsulfonyl)phenyl)acetic acid (134 mg, 0.589 mmol) in DCM (4 mL)' was added EDC (113 mg, 0.589 mmol) followed by HOBT (90 mg, 0.589 mmol). The reaction mixture was stirred overnight at room temperature. The solvent was removed under vacuum and crude product was purified on column chromatography.

Step-5:

To a stirred solution of 2-(4-(ethylsulfonyl)phenyl)-N-(4-(2,2,2-trifluoro-1-phenyl-1-((trimethylsilyl)oxy)ethyl)phenyl)acetamide (1.0 g, 1.819 mmol) in THF (3 mL), was added TBAF (0.951 g, 3.64 mmol) at 0° C. The reaction mixture was stirred overnight at room temperature. The reaction mixture was quenched with water, extracted further with DCM. The combined organic layer was dried over $Na_2SO_4$ and solvent was removed. The crude residue was purified on column chromatography to afford pure 2-(4-(ethylsulfonyl)phenyl)-N-(4-(2,2,2-trifluoro-1-hydroxy-1-phenylethyl)phenyl)acetamide.

$^1$H NMR (DMSO-$d_6$, 300 MHz) δ ppm: 10.37 (s, 1H), 7.85 (d, J=8.1 Hz, 2H), 7.60-7.57 (m, 4H), 7.40-7.29 (m, 8H), 3.79 (s, 2H), 3.29 (q, J=7.2 Hz, 2H), 1.09 (t, J=7.2 Hz, 3H); Mass (ESI): m/z 478.1 [M+H]$^+$.

The compounds of examples 90-100 were prepared analogous to the process described for the preparation of the compound of example 89.

Example 90

2-(4-(Ethylsulfonyl)phenyl)-N-(4-(2,2,2-trifluoro-1-hydroxy-1-(2-(trifluoromethoxy) phenyl) ethyl)phenyl)acetamide $^1$H NMR (DMSO-$d_6$, 300 MHz) δ ppm: 10.33 (s, 1H), 7.85 (d, J=8.1 Hz, 3H), 7.61-7.57 (m, 4H), 7.49 (d, J=7.5 Hz, 1H), 7.40 (s, 1H), 7.29-7.21 (m, 3H), 3.79 (s, 2H), 3.29 (q, J=7.2 Hz, 2H), 1.09 (t, J=7.2 Hz, 3H); Mass (ESI): m/z 562.1 [M+H]$^+$.

Example 91

2-(4-(Ethylsulfonyl)phenyl)-N-(4-(2,2,2-trifluoro-1-hydroxy-1-(4-methoxyphenyl)ethyl) phenyl)acetamide $^1$H NMR (DMSO-$d_6$, 300 MHz) δ ppm: 10.35 (s, 1H), 7.85 (d, J=8.1 Hz, 2H), 7.61-7.56 (m, 4H), 7.35-7.28 (m, 4H), 7.15 (s, 1H), 6.93 (d, J=9.0 Hz, 2H), 3.86 (s, 2H), 3.74 (s, 3H), 3.26 (q, J=7.5 Hz, 2H), 1.09 (t, J=7.2 Hz, 3H); Mass (ESI): m/z 508.1 [M+H]$^+$.

Example 92

N-(4-(1-Ethoxy-2,2,2-trifluoro-1-)phenylethyl)phenyl)-2-(4-(ethylsulfonyl) phenyl)acetamide $^1$H NMR (DMSO-$d_6$, 300 MHz) δ ppm: 10.43 (s, 1H), 7.85 (d, J=8.1 Hz, 2H), 7.65-7.59 (m, 4H), 7.41-7.31 (m, 5H), 7.27 (d, J=8.7 Hz, 2H), 3.80 (s, 2H), 3.39-3.23 (m, 4H), 3.19 (t, J=6.9 Hz, 3H), 1.09 (t, J=7.5 Hz, 3H); Mass (ESI): m/z 506.1 [M+H]$^+$.

Example 93

2-(4-(Ethylsulfonyl)phenyl)-N-(4-(2,2,2-trifluoro-1-isobutoxy-1-phenylethyl)phenyl) acetamide $^1$H NMR (DMSO-$d_6$, 300 MHz) δ ppm: 10.43 (s, 1H), 7.85 (d, J=7.5 Hz, 2H), 7.64-7.59 (m, 4H), 7.39-7.32 (m, 5H), 7.26 (d, J=8.7 Hz, 2H), 3.80 (s, 2H), 3.26 (q, J=6.3 Hz, 2H), 3.10 (d, J=6.9 Hz, 2H), 1.87-1.82 (m, 1H), 1.09 (t, J=7.5 Hz, 3H), 0.90 (d, J=6.6 Hz, 6H); Mass (ESI): m/z 534.2 [M+H]$^+$.

Example 94

2-(4-(Ethylsulfonyl)phenyl)-N-(4-(2,2,2-trifluoro-1-methoxy-1-phenylethyl)phenyl) acetamide $^1$H NMR (DMSO-$d_6$, 300 MHz) δ ppm: 10.44 (s, 1H), 7.85 (d, J=7.8 Hz, 2H), 7.63 (dd, J=8.1, 20.1 Hz, 4H), 7.42-7.41 (m, 3H), 7.32-7.24 (m, 4H), 3.80 (s, 2H), 3.26 (q, J=7.5 Hz, 2H), 3.21 (s, 3H), 1.09 (t, J=7.2 Hz, 3H); Mass (ESI): m/z 492.1 [M+H]$^+$.

Example 95

2-(4-(Ethylsulfonyl)phenyl)-N-(4-(1,2,2,2-tetrafluoro-1-phenylethyl)phenyl)acetamide $^1$H NMR (DMSO-$d_6$, 300 MHz) δ ppm: 10.51 (s, 1H), 7.85 (d, J=8.1 Hz, 2H), 7.72 (d, J=8.7 Hz, 2H), 7.61 (d, J=8.1 Hz, 2H), 7.51-7.39 (m, 7H), 3.82 (s, 2H), 3.26 (q, J=7.5 Hz, 2H), 1.09 (t, J=7.5 Hz, 3H), Mass (ESI): m/z 480.1 [M+H]$^+$.

Example 96

N-(4-(1-Cyano-2,2,2-trifluoro-1-phenylethyl)phenyl)-2-(4-(ethylsulfonyl)phenyl) acetamide $^1$H NMR (DMSO-$d_6$, 300 MHz) δ ppm: 10.55 (s, 1H), 7.86 (d, J=8.1 Hz, 2H), 7.65 (d, J=8.4 Hz, 2H), 7.61-7.46 (m, 5H), 7.42-7.39 (m, 4H), 3.82 (s, 2H), 3.26 (q, J=7.6 Hz, 2H), 1.09 (t, J=7.5 Hz, 3H), Mass (ESI): m/z 487.1 [M+H]$^+$.

Example 97

2-(4-(Ethylsulfonyl)phenyl)-N-(4-(2,2,2-trifluoro-1-morpholino-1-phenylethyl)phenyl) acetamide $^1$H NMR (DMSO-$d_6$, 300 MHz) δ ppm: 10.38 (s, 1H), 7.85 (d, J=8.1 Hz, 2H), 7.66 (dd, J=2.1, 8.7 Hz, 4H), 7.41-7.33 (m, 7H), 3.78 (s, 2H), 3.70-3.59 (m, 4H), 3.26 (q, J=7.5 Hz, 2H), 2.70-2.55 (m, 4H), 1.09 (t, J=7.5 Hz, 3H), Mass (ESI): m/z 547.2 [M+H]⁺.

Example 98

2-(4-(Ethylsulfonyl)phenyl)-N-(4-(2,2,2-trifluoro-1-phenyl-1-(pyrrolidin-1-yl)ethyl) phenyl) acetamide ¹H NMR (DMSO-d₆, 300 MHz) δ ppm: 10.39 (s, 1H), 7.86 (d, J=8.4 Hz, 2H), 7.6 (d, J=8.7 Hz, 4H), 7.40-7.24 (m, 7H), 3.80 (s, 2H), 3.26 (q, J=7.5 Hz, 2H), 2.70-2.55 (m, 4H), 1.70-1.68 (m, 4H), 1.09 (t, J=7.5 Hz, 3H), Mass (ESI): m/z 531.2 [M+H]⁺.

Example 99

2-(4-(Oxetan-3-ylsulfonyl)phenyl)-N-(4-(2,2,2-trifluoro-1-hydroxy-1-(2-methoxyphenyl) ethyl)phenyl) acetamide ¹H NMR (DMSO-d₆, 300 MHz) δ ppm: 10.30 (s, 1H), 7.89 (d, J=8.1 Hz, 2H), 7.63 (d, J=8.1 Hz, 2H), 7.53 (d, J=8.1 Hz, 2H), 7.41-7.35 (m, 1H), 7.23 (d, J=8.7 Hz, 2H), 7.06-6.98 (m, 2H), 6.69 (s, 1H), 4.87 (q, J=7.5 Hz, 1H), 4.77-4.69 (m, 4H), 3.79 (s, 2H), 3.35 (s, 3H); Mass (ESI): m/z 536.1 [M+H]⁺.

Example 100

2-(4-(Ethylsulfonyl)phenyl)-N-(4-(2,2,2-trifluoro-1-hydroxy-1-(1-methyl-1H-imidazol-4-yl) ethyl)phenyl)acetamide ¹H NMR (DMSO-d₆, 300 MHz) δ ppm 10.38 (s, 1H), 7.85 (d, J=7.8 Hz, 2H), 7.64 (s, 1H), 7.61 (d, J=7.8 Hz, 4H), 7.19 (d, J=10.2 Hz, 3H), 6.90 (s, 1H), 3.79 (s, 2H), 3.26 (q, J=7.5 Hz, 2H), 3.18 (s, 3H), 1.09 (t, J=7.5 Hz, 3H); Mass (ESI): m/z 482.1 [M+H]⁺.

Biological Assays

Representative compounds of formula I of the present invention were tested for their RORgamma inhibitory activity using the assays and the methods described below. The representative compounds are referred to as the test compounds.

CHO-K1 cells stably transfected with RORγt are maintained in MEM-EBS with 5% FBS, 1% penicillin streptomycin solution and 1 mg/mL G418. The cells are seeded at a density of 200000 cells/mL in white 96 well flat bottom plate. Post 16-18 hours incubation, the cells are transiently transfected with pFR Luc (50 ng/well DNA) for four hours. The cells are then treated with different doses of the test compounds in MEM EBS media with 10% FBS and 1% penicillin streptomycin. DMSO is used as vehicle control. After 18-20 hours treatment, the cells are lysed with lysis buffer (40 mM HEPES, 20 mM EGTA, 50 mM β-glycero-phosphate, 10% glycerol and 1% Triton X-100 in distilled water) for 0.5 hour and luminescence is read using Tecan Safire reader at 1000 milli second integration time.

The IC₅₀ (nM) values of the test compounds are presented in Table 1 wherein "+" refers to an IC₅₀ value in range of 0.01 nM to 50.00 nM, "++" refers to IC₅₀ value in range of 50.01 nM to 100.0 nM.

TABLE 1

| Compound of Example No | IC₅₀ (nM) |
|---|---|
| *In-vitro IC₅₀ value* | |
| 1 | + |
| 13 | + |
| 23 | ++ |
| 24 | + |
| 25 | + |
| 34 | + |
| 43 | + |

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:
1. A compound of formula I,

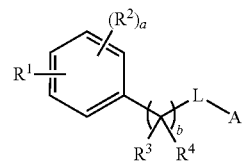

Formula I wherein:
R¹ is —S(O)ₘRᵃ, —S(O)ᵣNRᵇRᶜ, —S(O)ᵣ(NRᵇ)Rᵃ,
Rᵃ is (C₁-C₈)-alkyl, (C₃-C₁₂)-cycloalkyl, (C₆-C₁₀)-aryl or heterocyclyl;
Rᵇ and Rᶜ at each occurrence are independently selected from the group consisting of hydrogen, (C₁-C₈)-alkyl, (C₃-C₁₂)-cycloalkyl, (C₆-C₁₀)-aryl and heterocyclyl; or
Rᵇ and Rᶜ can combine to form a saturated or unsaturated 5- or 6-membered ring, optionally containing 1 or 2 additional heteroatoms selected from the group consisting of N, S and O;
wherein the ring can be unsubstituted or substituted with one or more groups independently selected from the group consisting of halogen, hydroxy, cyano, oxo, (C₁-C₈)-alkyl, (C₁-C₈)-alkoxy and halo (C₁-C₈)-alkyl;
m is 0, 1 or 2;
r is 1 or 2;
R² at each occurrence is independently selected from the group consisting of hydrogen, halogen, hydroxy, cyano, (C₁-C₈)-alkyl, (C₁-C₈)-alkoxy, (C₃-C₁₂)-cycloalkyl, halo(C₁-C₈)-alkyl, halo(C₁-C₈)-alkoxy, NRᵃ¹Rᵃ², CORᵃ³, COORᵃ³ and CONRᵃ¹Rᵃ²; or
R¹ and R² when present on adjacent carbon atoms of the phenyl can combine to form a saturated 5- or 6-membered ring containing S or SO₂; which ring can be unsubstituted or substituted with one or more groups independently selected from the group consisting of halogen, cyano, oxo, (C₁-C₈)-alkyl, (C₂-C₈)-alkenyl, (C₂-C₈)-alkynyl, (C₁-C₈)-alkoxy and halo(C₁-C₈)-alkyl;
R³ and R⁴ are independently selected from the group consisting of hydrogen or (C₁-C₈)-alkyl;

a is 1 or 2;
b is 1;
L is —CO—;
A is

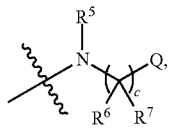
A-1

$R^5$ is hydrogen, $(C_1-C_8)$-alkyl, halo$(C_1-C_8)$alkyl or $(C_3-C_{12})$-cycloalkyl;

$R^6$ and $R^7$ are independently selected from the group consisting of hydrogen, halogen, hydroxy, cyano, $(C_1-C_8)$-alkyl, $(C_2-C_8)$-alkenyl, $(C_1-C_8)$-alkoxy, halo$(C_1-C_8)$alkyl, $(C_3-C_{12})$-cycloalkyl, $(C_6-C_{10})$-aryl, CONR$^{a1}$R$^{a2}$, COR$^{a3}$ and COOR$^3$; or $R^6$ and $R^7$ can combine to form saturated or unsaturated 3-6 membered cyclic ring optionally containing 1 or 2 heteroatoms selected from the group consisting of O, N and S; wherein the ring can be unsubstituted or substituted with one or more groups independently selected from the group consisting of oxo, hydroxy, cyano, halogen, $(C_1-C_8)$-alkyl, halo$(C_1-C_8)$-alkyl, COR$^{a3}$, COOR$^{a3}$, CONR$^{a2}$R$^{a3}$, $(C_1-C_8)$alkoxy and halo$(C_1-C_8)$-alkoxy;

c is 0;
Q is

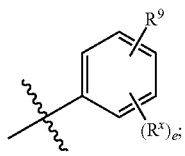
Q-1

$R^9$ is $(CR^jR^j)_fR^b$, $(CR^jR^j)_fOR^k$, $(CR^jR^j)_fN(R^k)_2$, $(CR^jR^j)_f$CN, $(CR^jR^j)_f$-halogen, W—$(C_3-C_{12})$-cycloalkyl, W—$(C_5-C_{10})$-cycloalkenyl, $W^1$—$(C_6-C_{10})$-aryl, $W^1$-heterocyclyl or $W^1$-heteroaryl;

$R^k$ is hydrogen, $(C_1-C_8)$-alkyl, $(C_3-C_{12})$-cycloalkyl, $(C_5-C_{10})$-cycloalkenyl, -$(C_1-C_8)$-alkylene-$(C_3-C_{12})$-cycloalkyl, -$(C_1-C_8)$-alkylene-$(C_5-C_{10})$-cycloalkenyl, $(C_6-C_{10})$-aryl, -$(C_1-C_8)$-alkylene-$(C_6-C_{10})$-aryl, heteroaryl, heterocyclyl, -$(C_1-C_8)$-alkylene-heteroaryl or -$(C_1-C_8)$-alkylene-heterocyclyl;

$R^x$ at each occurrence are independently selected from the group consisting of hydrogen, halogen, hydroxy, cyano, oxo, $(C_1-C_8)$-alkyl, $(C_1-C_8)$-alkoxy, $(C_3-C_{12})$-cycloalkyl, halo$(C_1-C_8)$-alkyl, halo$(C_1-C_8)$-alkoxy, NR$^{a1}$R$^{a2}$, COR$^{a3}$, COOR$^{a3}$ and CONR$^{a1}$R$^{a2}$;

W is a bond, —O—, CO, NH, $(CR^jR^g)_f$, $(CR^jR^g)_f$—C≡C— or $(C_5-C_{10})$-cycloalkenyl;

$W^1$ is $(CR^jR^j)_f$, $(CR^jR^g)_f$—C≡C— or $(C_5-C_{10})$-cycloalkenyl;

$R^j$ is $(C_1-C_8)$alkyl, $(C_1-C_8)$alkoxy, halo$(C_1-C_8)$alkyl, COOR$^{a3}$ or heterocyclyl;

$R^j$ is selected from the group consisting of halogen, cyano, hydroxy, and halo$(C_1-C_8)$alkyl;

$R^g$ is selected from the group consisting of hydrogen, halogen, cyano, hydroxy, $(C_1-C_8)$alkyl and halo$(C_1-C_8)$alkyl;

e is 1 or 2;
f is 1, 2, 3 or 4;
wherein:
each of the $(C_1-C_8)$-alkyl, $(C_1-C_8)$-alkylene, $(C_2-C_8)$-alkenyl and $(C_1-C_8)$-alkoxy can be unsubstituted or substituted with one or more groups independently selected from the group consisting of halogen, hydroxy, oxo, cyano, $(C_1-C_8)$-alkynyl, $(C_1-C_8)$-alkoxy, $(C_3-C_{12})$-cycloalkyl, $(C_6-C_{10})$-aryl, heterocyclyl, heteroaryl, halo$(C_1-C_8)$alkoxy, C(O)R$^h$, OC(O)R$^h$, COOR$^h$, C(O)NR$^h$R$^i$, O—R$^i$, OC(O)NR$^h$R$^i$, NR$^h$R$^i$, NR$^h$C(O)R$^i$, NR$^h$C(O)NR$^h$R$^i$, S(O)$_q$$(C_1-C_8)$-alkyl, S(O)$_r$NR$^h$R$^i$ and NR$^h$S(O)$_q$R$^i$;

each of the $(C_3-C_{12})$-cycloalkyl, $(C_5-C_{10})$-cycloalkenyl and $(C_6-C_{10})$-aryl can be unsubstituted or substituted with one or more groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, C(O)R$^h$, COOR$^h$, C(O)NR$^h$R$^i$, O—R$^i$, OC(O)R$^h$, OC(O)NR$^h$R$^i$, NR$^h$R$^i$, NR$^h$C(O)R$^i$, NR$^h$C(O)NR$^h$R$^i$, S(O)$_q$$(C_1-C_8)$-alkyl, S(O)$_r$NR$^h$R$^i$ and NR$^h$S(O)$_q$R$^i$;

heterocyclyl is a 3- to 10-membered ring containing 1, 2, 3 or 4 heteroatoms independently selected from the group consisting of N, S and O, wherein said heterocyclyl is unsubstituted or substituted with one or more groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, C(O)R$^h$, COOR$^h$, C(O)NR$^h$R$^i$, O—R$^i$, OC(O)R$^h$, OC(O)NR$^h$R$^i$, NR$^h$R$^i$, NR$^h$C(O)R$^i$, NR$^h$C(O)NR$^h$R$^i$, S(O)$_q$$(C_1-C_8)$-alkyl, S(O)$_r$NR$^h$R$^i$ and NR$^h$S(O)$_q$R$^i$;

heteroaryl is a 5- to 10-membered ring containing 1, 2, 3 or 4 heteroatoms independently selected from the group consisting of N, S and O, wherein said heteroaryl is unsubstituted or substituted with one or more groups independently selected from the group consisting of halogen, hydroxy, oxo, cyano, $(C_1-C_8)$-alkyl, $(C_1-C_8)$-alkoxy, $(C_3-C_{12})$-cycloalkyl, $(C_6-C_{10})$-aryl, heterocyclyl, heteroaryl, halo$(C_1-C_8)$alkyl, halo$(C_1-C_8)$alkoxy, C(O)R$^h$, COOR$^h$, C(O)NR$^h$R$^i$, O—R$^i$, OC(O)R$^h$, OC(O)NR$^h$R$^i$, NR$^h$R$^i$, NR$^h$C(O)R$^i$, NR$^h$C(O)NR$^h$R$^i$, S(O)$_q$$(C_1-C_8)$-alkyl, S(O)$_r$NR$^h$R$^i$ and NR$^h$S(O)$_q$R$^i$; and $R^h$ and $R^i$ are independently selected from the group consisting of hydrogen, $(C_1-C_8)$-alkyl, $(C_2-C_8)$-alkenyl, halo$(C_1-C_8)$alkyl, $(C_3-C_{12})$-cycloalkyl, $(C_6-C_{10})$-aryl, $(C_6-C_{10})$-aryl-$(C_1-C_8)$-alkyl, heteroaryl and heterocyclyl;

provided that,
(i) when $R^1$ is —S(O)$_r$NR$^b$R$^c$, wherein $R^b$ and $R^c$ can combine to form a saturated or unsaturated 5- or 6-membered ring, then Q is

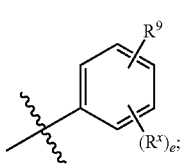
Q-1 or an isotopic form, a stereoisomer or tautomer thereof; or a pharmaceutically acceptable salt, S oxide or N-oxide thereof.

2. The compound according to claim 1, wherein:
$R^1$ is —S(O)$_m$R$^a$, —S(O)$_r$NR$^b$R$^c$ or —S(O)$_r$(NR$^b$)R$^a$;
provided that,
when $R^1$ is —S(O)$_r$NR$^b$R$^c$, wherein $R^b$ and $R^c$ can combine to form a saturated or unsaturated 5- or 6-membered ring, then Q is

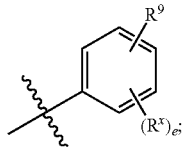

Q-1 or an isotopic form, a stereoisomer, a tautomer, a pharmaceutically acceptable salt, N oxide or S-oxide thereof.

3. The compound according to claim 1, wherein:
$R^1$ is —S(O)$_m$R$^a$;
$R^a$ is (C$_1$-C$_8$)-alkyl, (C$_3$-C$_{12}$)-cycloalkyl, (C$_6$-C$_{10}$)-aryl or heterocyclyl;
m is 0, 1 or 2; and
$R^2$ is hydrogen;
or an isotopic form, a stereoisomer, a tautomer, a pharmaceutically acceptable salt, N oxide or S-oxide thereof.

4. The compound according to claim 1, wherein:
A is

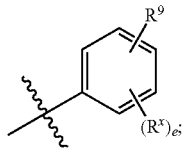

A-1 c is 0; and
$R^5$, $R^6$, are $R^7$ as defined in claim 1;
or an isotopic form, a stereoisomer, a tautomer, a pharmaceutically acceptable salt, N oxide or S-oxide thereof.

5. The compound according to claim 1, wherein:
Q is

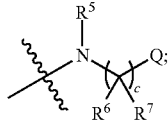

Q-1

$R^9$ is (CR$^f$R$^j$)$_b$R$^b$;
$R^f$ is cyano;
$R^j$ is (C$_1$-C$_8$)alkyl, (C$_1$-C$_8$)alkoxy, halo(C$_1$-C$_8$)alkyl, COOR$^{a3}$ or heterocyclyl;

$R^b$ is hydrogen, (C$_1$-C$_8$)-alkyl, (C$_3$-C$_{12}$)-cycloalkyl, (C$_6$-C$_{10}$)-aryl and heterocyclyl; and
b, f are 1;
or an isotopic form, a stereoisomer, a tautomer, a pharmaceutically acceptable salt, N oxide or S-oxide thereof.

6. The compound according to claim 1, wherein:
A is

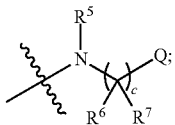

A-1

Q is

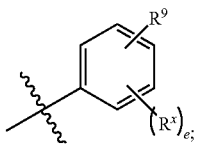

Q-1

$R^9$ is (CR$^f$R$^j$)$_b$R$^b$ and is attached at position 4 in Q-1 ring;
$R^f$ is cyano;
b, f are 1;
c is 0;
$R^a$, $R^b$, $R^1$, $R^2$, $R^3$, $R^4$, $R^5$, $R^6$, $R^7$, $R^j$, $R^x$, a, e, m, and n are as defined in claim 1;
wherein $R^b$ and $R^c$, $R^1$ and $R^2$, $R^3$ and $R^4$, $R^6$ and $R^7$, do not combine to form a ring;
or an isotopic form, a stereoisomer, a tautomer, a pharmaceutically acceptable salt, N oxide or S-oxide thereof.

7. The compound according to claim 1 selected from:
2-(4-(Ethylsulfonyl)phenyl)-N-(4-(1,1,1,3,3,3-hexafluoro-2-methoxypropan-2-yl)phenyl) acetamide;
N-(4-Cyclohexyl-2-(1,1,1,3,3,3-hexafluoro-2-hydroxy-propan-2-yl)phenyl)-2-(4-(ethyl sulfonyl)phenyl)acetamide;
N-(4-(1-Cyanocyclopropyl)phenyl)-2-(4-(ethylsulfonyl) phenyl)acetamide;
2-(4-(Ethylsulfonyl)phenyl)-N-(4-(1,1,1,3,3,3-hexafluoro-2-(4-phenylbutoxy)propan-2-yl)phenyl)acetamide;
2-(4-(Ethylsulfonyl)phenyl)-N-(4-(1,1,1,3,3,3-hexafluoro-2-hydroxypropan-2-yl)-2-methylphenyl) acetamide;
2-(4-(Ethylsulfonyl)phenyl)-N-(3-(1,1,1,3,3,3-hexafluoro-2-hydroxypropan-2-yl)phenyl) acetamide;
2-(4-(Ethylsulfonyl)phenyl)-N-(4-(1,1,1-trifluoro-2-hydroxypropan-2-yl)phenyl) acetamide;
2-(4-(Ethylsulfonyl)phenyl)-N-(4-(2,2,2-trifluoro-1-hydroxyethyl)phenyl)acetamide;
N-(4-(2-(2-Cyclohexylethoxy)-1,1,1,3,3,3-hexafluoro-propan-2-yl)phenyl)-2-(4-(ethyl sulfonyl)phenyl)acetamide;
2-(4-(Ethylsulfonyl)phenyl)-N-(4-(1,1,1,3,3,3-hexafluoro-2-(2-(piperidin-1-yl)ethoxy) propan-2-yl) phenyl)acetamide;

2-(4-(Ethylsulfonyl)phenyl)-N-(4-(1,1,1,3,3,3-hexafluoro-2-hydroxypropan-2-yl) phenyl)acetamide;
N-(4-(2-Cyanopropan-2-yl)phenyl)-2-(4-(ethyl sulfonyl) phenyl)acetamide;
2-(4-(Ethyl sulfonyl)phenyl)-N-(4-phenylcyclohexyl)acetamide;
N-(4-(Cyclohexyloxy)-3-(trifluoromethyl)phenyl)-2-(4-(ethylsulfonyl)phenyl) acetamide;
2-(4-(Ethylsulfonyl)phenyl)-N-(4'-oxo-2-(trifluoromethyl)-2',3',4',5'-tetrahydro-[1,1'-biphenyl]-4-yl)acetamide;
N-(4-Cyclohexylphenyl)-2-(4-(ethyl sulfonyl)phenyl)acetamide;
N-(4-(1,1,1,3,3,3-Hexafluoro-2-hydroxypropan-2-yl) phenyl)-2-(4-(morpholinosulfonyl) phenyl)acetamide;
2-(4-(Ethylsulfonyl)phenyl)-N-(4-(1-hydroxy-1-phenylethyl)phenyl)acetamide;
2-(4-(Ethylsulfonamido)phenyl)-N-(4-(1,1,1,3,3,3-hexafluoro-2-hydroxypropan-2-yl) phenyl)acetamide;
2-(4-(Ethyl sulfonyl)phenyl)-N-(4-(perfluoropropan-2-yl)phenyl)acetamide;
N-(Cyclopropylmethyl)-2-(4-(ethylsulfonyl)phenyl)-N-(4-(1,1,1,3,3,3-hexafluoro-2-hydroxypropan-2-yl)phenyl)acetamide;
2-(4-(Ethylsulfonimidoyl)phenyl)-N-(3-(1,1,1,3,3,3-hexafluoro-2-hydroxypropan-2-yl)phenyl)acetamide
N-(4-(2-Cyano-1,1,1,3,3,3-hexafluoropropan-2-yl)phenyl)-2-(4-(ethylsulfonimidoyl) phenyl)acetamide;
2-(4-(Ethylsulfonimidoyl)phenyl)-N-(4-(1,1,1,3,3,3-hexafluoro-2-hydroxypropan-2-yl)-2-methylphenyl) acetamide;
N-(4-(2-Ethoxy-1,1,1,3,3,3-hexafluoropropan-2-yl)phenyl)-2-(4 ethylsulfonimidoyl) phenyl)acetamide;
N-(4-(2-Ethoxy-1,1,1,3,3,3-hexafluoropropan-2-yl)phenyl)-2-(4-(ethylsulfonyl) phenyl)acetamide;
2-(4-(Ethylsulfonyl)phenyl)-N-(4-(1,1,1,3,3,3-hexafluoro-2-isopropoxypropan-2-yl)phenyl)acetamide;
2-(4-(Ethylsulfonyl)phenyl)-N-(4-(1,1,1,3,3,3-hexafluoro-2-propoxypropan-2-yl)phenyl)acetamide;
2-(4-(Ethylsulfonyl)phenyl)-N-(4-(1,1,1,3,3,3-hexafluoro-2-(prop-2-yn-1-yloxy) propan-2-yl)phenyl)acetamide;
2-(4-(Ethylsulfonyl)phenyl)-N-(4-(1,1,1,3,3,3-hexafluoro-2-(pyridin-2-ylmethoxy) propan-2-yl)phenyl)acetamide;
2-(4-(Ethylsulfonyl)phenyl)-N-(4-(1,1,1,3,3,3-hexafluoro-2-(pyridin-2-ylmethoxy) propan-2-yl)phenyl)acetamide hydrochloride;
2-(4-(Ethylsulfonyl)phenyl)-N-(4-(1,1,1,3,3,3-hexafluoro-2-methoxypropan-D3-2-yl)phenyl) acetamide;
2-(4-(Ethylsulfonyl)phenyl)-N-(4-(1,1,1,3,3,3-hexafluoro-2-(2-methoxyethoxy) propan-2-yl)phenyl) acetamide;
N-(4-(2-(Cyclopropylmethoxy)-1,1,1,3,3,3-hexafluoropropan-2-yl)phenyl)-2-(4-(ethylsulfonyl)phenyl)acetamide;
2-(4-(Ethylsulfonyl)phenyl)-N-(4-(1,1,1,3,3,3-hexafluoro-2-isobutoxypropan-2-yl)phenyl)acetamide;
Methyl 2-((2-(4-(2-(4-(ethylsulfonyl)phenyl)acetamido)phenyl)-1,1,1,3,3,3-hexafluoro propan-2-yl)oxy)acetate;
N-(4-(2-(Cyclobutylmethoxy)-1,1,1,3,3,3-hexafluoropropan-2-yl)phenyl)-2-(4-(ethylsulfonyl)phenyl)acetamide;
2-(4-(Ethylsulfonyl)phenyl)-N-(4-(1,1,1,3,3,3-hexafluoro-2-(1H-pyrazol-1-yl)propan-2-yl)phenyl)acetamide;
N-(4-(1,1,1,3,3,3-Hexafluoro-2-hydroxypropan-2-yl) phenyl)-2-(4-(methylsulfonyl) phenyl)acetamide;
2-(4-(N,N-Dimethylsulfamoyl)phenyl)-N-(4-(1,1,1,3,3,3-hexafluoro-2-(pyridin-2-ylmethoxy)propan-2-yl)phenyl)acetamide;
N-Ethyl-2-(4-(ethylsulfonyl)phenyl)-N-(4-(1,1,1,3,3,3-hexafluoro-2-hydroxypropan-2-yl)phenyl)acetamide;
2-(4-(Ethylsulfonyl)phenyl)-N-(4-(1,1,1,3,3,3-hexafluoro-2-hydroxypropan-2-yl)phenyl)-N-isopropylacetamide;
2-(4-(N,N-Dimethylsulfamoyl)phenyl)-N-ethyl-N-(4-(1,1,1,3,3,3-hexafluoro-2-hydroxypropan-2-yl)phenyl)acetamide;
2-(4-(Ethylsulfonyl)phenyl)-N-isobutyl-N-(4-(perfluoropropan-2-yl)phenyl) acetamide;
2-(4-(Ethylsulfonyl)phenyl)-N-(4-(1,1,1,3,3,3-hexafluoropropan-2-yl)phenyl) acetamide;
Methyl 2-(4-(2-(4-(ethylsulfonyl)phenyl)acetamido)phenyl)-3,3,3-trifluoro-2-hydroxypropanoate;
N-(4-(2-Amino-1,1,1,3,3,3-hexafluoropropan-2-yl)phenyl)-2-(4-(ethylsulfonyl) phenyl)acetamide;
2-(4-(Ethylsulfonyl)phenyl)-N-(4-(1,1,1,3,3,3-hexafluoro-2-(1H-imidazol-1-yl)propan-2-yl)phenyl) acetamide;
2-(4-(Ethylsulfonyl)phenyl)-N-(4-(1,1,1,3,3,3-hexafluoro-2-(1H-tetrazol-5-yl)propan-2-yl)phenyl)acetamide;
2-(4-(Ethylsulfonyl)phenyl)-N-(4-(1,1,1,3,3,3-hexafluoro-2-(2-morpholinoethoxy) propan-2-yl)phenyl)acetamide;
N-(4-(1,1,1,3,3,3-Hexafluoro-2-hydroxypropan-2-yl) phenyl)-2-(4-(oxetan-3-ylsulfonyl)phenyl)acetamide;
2-(4-(Ethylsulfonyl)phenyl)-N-(4-(1,1,1,3,3,3-hexafluoro-2-(oxetan-3-yloxy)propan-2-yl) phenyl)acetamide;
2-(4-(Ethylsulfonyl)phenyl)-N-(4-(1,1,1,3,3,3-hexafluoro-2-morpholinopropan-2-yl)phenyl)acetamide;
2-(4-(Ethylsulfonyl)phenyl)-N-(4-(1,1,1,3,3,3-hexafluoro-2-(3-methylpiperidin-1-yl)propan-2-yl) phenyl)acetamide;
2-(4-(Ethylsulfonyl)phenyl)-N-(4-(1,1,1,3,3,3-hexafluoro-2-(4-(4-methoxyphenyl) piperazin-1-yl) propan-2-yl)phenyl)acetamide;
2-(4-(Ethylsulfonyl)phenyl)-N-(4-(1,1,1,3,3,3-hexafluoro-2-(4-(4-fluorophenyl) piperazin-1-yl)propan-2-yl)phenyl)acetamide;
N-(4-(2-Cyano-1,1,1,3,3,3-hexafluoropropan-2-yl)phenyl)-2-(4-(ethylsulfonyl)phenyl) acetamide;
2-(4-(Ethylsulfonyl)phenyl)-N-(4-(1,1,1,3,3,3-hexafluoro-2-methylpropan-2-yl)phenyl)acetamide;
2-(4-(Ethylsulfonyl)phenyl)-N-(4-(2,2,2-trifluoro-1-hydroxy-1-phenylethyl)phenyl) acetamide;
2-(4-(Ethylsulfonyl)phenyl)-N-(4-(2,2,2-trifluoro-1-hydroxy-1-(2-(trifluoromethoxy) phenyl)ethyl)phenyl)acetamide;
2-(4-(Ethylsulfonyl)phenyl)-N-(4-(2,2,2-trifluoro-1-hydroxy-1-(4-methoxyphenyl) ethyl)phenyl)acetamide;
N-(4-(1-Ethoxy-2,2,2-trifluoro-1-phenylethyl)phenyl)-2-(4-(ethylsulfonyl) phenyl)acetamide;
2-(4-(Ethylsulfonyl)phenyl)-N-(4-(2,2,2-trifluoro-1-isobutoxy-1-phenylethyl)phenyl) acetamide;
2-(4-(Ethylsulfonyl)phenyl)-N-(4-(2,2,2-trifluoro-1-methoxy-1-phenylethyl)phenyl) acetamide;

2-(4-(Ethylsulfonyl)phenyl)-N-(4-(1,2,2,2-tetrafluoro-1-phenylethyl) phenyl)acetamide;

N-(4-(1-Cyano-2,2,2-trifluoro-1-phenylethyl)phenyl)-2-(4-(ethylsulfonyl) phenyl)acetamide;

2-(4-(Ethylsulfonyl)phenyl)-N-(4-(2,2,2-trifluoro-1-morpholino-1-phenylethyl) phenyl)acetamide;

2-(4-(Ethylsulfonyl)phenyl)-N-(4-(2,2,2-trifluoro-1-phenyl-1-(pyrrolidin-1-yl)ethyl)phenyl)acetamide;

2-(4-(Oxetan-3-ylsulfonyl)phenyl)-N-(4-(2,2,2-trifluoro-1-hydroxy-1-(2-methoxyphenyl)ethyl)phenyl)acetamide;

2-(4-(Ethylsulfonyl)phenyl)-N-(4-(2,2,2-trifluoro-1-hydroxy-1-(1-methyl-1H-imidazol-4-yl)ethyl)phenyl)acetamide;

or a stereoisomer, a tautomer or a pharmaceutically acceptable salt thereof.

8. A pharmaceutical composition comprising a therapeutically effective amount of a compound of formula I of claim 1, or an isotopic form, a stereoisomer, a tautomer or a pharmaceutically acceptable salt thereof; and at least one pharmaceutically acceptable excipient.

9. A method for the treatment of diseases or disorders mediated by RORgamma comprising administering to a subject in need thereof, a therapeutically effective amount of compound of formula I of claim 1, or an isotopic form, a stereoisomer, a tautomer or a pharmaceutically acceptable salt thereof.

10. The method according to claim 9, wherein the disease or disorder is an autoimmune disorder or an inflammatory disorder.

11. The method according to claim 9, wherein the compound of formula I is selected from:

N-(4-(2-cyano-1,1,1,3,3,3-hexafluoropropan-2-yl)phenyl)-2-(4-(ethylsulfonimidoyl) phenyl)acetamide;

2-(4-(Ethylsulfonyl)phenyl)-N-(4-(1,1,1-trifluoro-2-hydroxypropan-2-yl)phenyl) acetamide;

N-(4-(2-Ethoxy-1,1,1,3,3,3-hexafluoropropan-2-yl)phenyl)-2-(4-(ethylsulfonyl) phenyl) acetamide;

2-(4-(Ethylsulfonyl)phenyl)-N-(4-(1,1,1,3,3,3-hexafluoro-2-(2-methoxyethoxy)propan-2-yl)phenyl)acetamide;

2-(4-(Ethylsulfonyl)phenyl)-N-(4-(1,1,1,3,3,3-hexafluoro-2-(1H-pyrazol-1-yl)propan-2-yl)phenyl)acetamide;

N-(4-(2-Cyano-1,1,1,3,3,3-hexafluoropropan-2-yl)phenyl)-2-(4-(ethylsulfonyl)phenyl) acetamide;

2-(4-(Ethylsulfonyl)phenyl)-N-(4-(2,2,2-trifluoro-1-methoxy-1-phenylethyl)phenyl) acetamide;

or a stereoisomer, a tautomer or a pharmaceutically acceptable salt thereof.

12. The method according to claim 10, wherein the compound of formula I is selected from:

N-(4-(2-cyano-1,1,1,3,3,3-hexafluoropropan-2-yl)phenyl)-2-(4-(ethylsulfonimidoyl) phenyl)acetamide;

2-(4-(Ethylsulfonyl)phenyl)-N-(4-(1,1,1-trifluoro-2-hydroxypropan-2-yl)phenyl) acetamide;

N-(4-(2-Ethoxy-1,1,1,3,3,3-hexafluoropropan-2-yl)phenyl)-2-(4-(ethylsulfonyl) phenyl) acetamide;

2-(4-(Ethylsulfonyl)phenyl)-N-(4-(1,1,1,3,3,3-hexafluoro-2-(2-methoxyethoxy)propan-2-yl)phenyl)acetamide;

2-(4-(Ethylsulfonyl)phenyl)-N-(4-(1,1,1,3,3,3-hexafluoro-2-(1H-pyrazol-1-yl)propan-2-yl)phenyl)acetamide;

N-(4-(2-Cyano-1,1,1,3,3,3-hexafluoropropan-2-yl)phenyl)-2-(4-(ethylsulfonyl)phenyl) acetamide;

2-(4-(Ethylsulfonyl)phenyl)-N-(4-(2,2,2-trifluoro-1-methoxy-1-phenylethyl)phenyl) acetamide;

or a stereoisomer, a tautomer or a pharmaceutically acceptable salt thereof.

13. The method according to claim 9, wherein the compound of formula I is N-(4-(2-cyano-1,1,1,3,3,3-hexafluoropropan-2-yl)phenyl)-2-(4-(ethyl sulfonimidoyl) phenyl) acetamide;

or a stereoisomer, a tautomer or a pharmaceutically acceptable salt thereof.

14. The method according to claim 10, wherein the compound of formula I is N-(4-(2-cyano-1,1,1,3,3,3-hexafluoropropan-2-yl)phenyl)-2-(4-(ethyl sulfonimidoyl) phenyl)acetamide;

or a stereoisomer, a tautomer or a pharmaceutically acceptable salt thereof.

15. The compound of claim 1, wherein the compound of formula I is selected from:

N-(4-(2-cyano-1,1,1,3,3,3-hexafluoropropan-2-yl)phenyl)-2-(4-(ethylsulfonimidoyl) phenyl)acetamide;

2-(4-(Ethylsulfonyl)phenyl)-N-(4-(1,1,1-trifluoro-2-hydroxypropan-2-yl)phenyl) acetamide;

N-(4-(2-Ethoxy-1,1,1,3,3,3-hexafluoropropan-2-yl)phenyl)-2-(4-(ethylsulfonyl) phenyl) acetamide;

2-(4-(Ethylsulfonyl)phenyl)-N-(4-(1,1,1,3,3,3-hexafluoro-2-(2-methoxyethoxy)propan-2-yl)phenyl)acetamide;

2-(4-(Ethylsulfonyl)phenyl)-N-(4-(1,1,1,3,3,3-hexafluoro-2-(1H-pyrazol-1-yl)propan-2-yl)phenyl)acetamide;

N-(4-(2-Cyano-1,1,1,3,3,3-hexafluoropropan-2-yl)phenyl)-2-(4-(ethylsulfonyl)phenyl) acetamide;

2-(4-(Ethylsulfonyl)phenyl)-N-(4-(2,2,2-trifluoro-1-methoxy-1-phenylethyl)phenyl) acetamide;

or a stereoisomer, a tautomer or a pharmaceutically acceptable salt thereof.

16. A pharmaceutical composition comprising a therapeutically effective amount of a compound of claim 15, or an isotopic form, a stereoisomer, a tautomer or a pharmaceutically acceptable salt thereof; and at least one pharmaceutically acceptable excipient.

17. The compound of claim 1, wherein the compound is N-(4-(2-cyano-1,1,1,3,3,3-hexafluoropropan-2-yl)phenyl)-2-(4-(ethylsulfonimidoyl) phenyl)acetamide; or a stereoisomer, a tautomer or a pharmaceutically acceptable salt thereof.

18. A pharmaceutical composition comprising a therapeutically effective amount of a compound of claim 17, or an isotopic form, a stereoisomer, a tautomer or a pharmaceutically acceptable salt thereof; and at least one pharmaceutically acceptable excipient.

* * * * *